(12) United States Patent
Nazzaro et al.

(10) Patent No.: US 10,661,012 B2
(45) Date of Patent: May 26, 2020

(54) FILLING ASSIST MECHANISMS AND KEYED INTERFACES FOR DRUG DELIVERY DEVICES

(71) Applicant: INSULET CORPORATION, Acton, MA (US)

(72) Inventors: David Nazzaro, Groveland, MA (US); Maureen McCaffrey, Boston, MA (US); Robert F. Rioux, Ashland, MA (US); Michael Philip Graffeo, Millbury, MA (US); Ian McLaughlin, Boxboro, MA (US); Nicholas Jansky, North Billerica, MA (US); Sam Rosenblum, Medford, MA (US); David Clare, Georgetown, MA (US); Robert D. Schaefer, Wakefield, MA (US); Daniel P. Allis, Boxford, MA (US); Bryan Dillon, Jefferson, MA (US); Steven Barletta, Tewksbury, MA (US); Bryan Choate, Salem, MA (US); Raymond Dobry, Methuen, MA (US); John LeFavour, Chelmsford, MA (US)

(73) Assignee: Insulet Corporation, Acton, MA (US)

(*) Notice: Subject to any disclaimer, the term of this patent is extended or adjusted under 35 U.S.C. 154(b) by 623 days.

(21) Appl. No.: 15/398,657

(22) Filed: Jan. 4, 2017

(65) Prior Publication Data

US 2017/0189270 A1    Jul. 6, 2017

Related U.S. Application Data

(60) Provisional application No. 62/274,445, filed on Jan. 4, 2016, provisional application No. 62/276,020, filed
(Continued)

(51) Int. Cl.
*A61M 5/00* (2006.01)
*A61M 5/178* (2006.01)
(Continued)

(52) U.S. Cl.
CPC ........... *A61M 5/1782* (2013.01); *A61M 5/321* (2013.01); *A61M 2005/3109* (2013.01); *A61M 2005/3267* (2013.01); *A61M 2205/6045* (2013.01)

(58) Field of Classification Search
CPC .... A61M 5/178; A61M 5/1782; A61M 5/321; A61M 2005/3109; A61M 2005/3267; A61M 2205/6045; A61J 1/2096
See application file for complete search history.

(56) References Cited

U.S. PATENT DOCUMENTS

| 5,213,483 A | 5/1993 | Flaherty et al. |
| 5,575,770 A | 11/1996 | Melsky et al. |

(Continued)

FOREIGN PATENT DOCUMENTS

| WO | 2009070731 A1 | 6/2009 |
| WO | 2014154777 A1 | 10/2014 |
| WO | 2015061690 A1 | 4/2015 |
| WO | 2016162755 A2 | 10/2016 |

OTHER PUBLICATIONS

International Search Report; PCT/US17/12207; dated May 26, 2017.
(Continued)

*Primary Examiner* — Philip R Wiest

(57) ABSTRACT

Systems, components, and methods are disclosed for withdrawing drug from a liquid drug container and transferring drug to a medical device. One or more components may have keying features so that only the correct liquid drug container and medical device are accessed, making sure the medical device is filled with the correct drug. A syringe
(Continued)

needle hub may have keying features corresponding to keying features on a cap on the liquid drug container and on the medical device. An alignment device facilitates easy-to-operate filling of a medical device. The alignment device aligns a liquid drug container over a fill port of the medical device and can include components for moving the liquid drug container into engagement with the medical device and for automatically initiating drug transfer to the medical device. A retractable skirt or needle cover protects the needle and is unlocked only when the skirt or needle cover is close to or touching the medical device.

13 Claims, 85 Drawing Sheets

Related U.S. Application Data on Jan. 7, 2016, provisional application No. 62/276,045, filed on Jan. 7, 2016, provisional application No. 62/275,965, filed on Jan. 7, 2016, provisional application No. 62/374,311, filed on Aug. 12, 2016, provisional application No. 62/378,264, filed on Aug. 23, 2016, provisional application No. 62/395,498, filed on Sep. 16, 2016, provisional application No. 62/407,113, filed on Oct. 12, 2016.

(51) Int. Cl.
*A61M 5/32* (2006.01)
*A61M 5/31* (2006.01)

(56) References Cited

U.S. PATENT DOCUMENTS

| | | |
|---|---|---|
| 5,814,020 A | 9/1998 | Gross |
| 6,045,533 A | 4/2000 | Kriesel et al. |
| 6,152,898 A | 11/2000 | Olsen |
| 6,206,850 B1 | 3/2001 | O'Neil |
| 6,666,852 B2 | 12/2003 | Niedospial |
| 7,220,245 B2 | 5/2007 | Kriesel |
| 8,613,724 B2 | 12/2013 | Lanier |
| 2002/0066715 A1 | 6/2002 | Niedospial et al. |
| 2003/0139774 A1 | 7/2003 | Epstein et al. |
| 2007/0025811 A1 | 2/2007 | Wilhelm |
| 2007/0112332 A1 | 5/2007 | Harding et al. |
| 2008/0001737 A1 | 1/2008 | Metry |
| 2008/0051765 A1 | 2/2008 | Mounce |
| 2008/0065000 A1 | 3/2008 | Bidinger et al. |
| 2008/0119790 A1 | 5/2008 | Hawkins et al. |
| 2008/0249508 A1 | 10/2008 | Lopez et al. |
| 2011/0130742 A1 | 6/2011 | Hawkins et al. |
| 2011/0231204 A1 | 9/2011 | De La Huerga |
| 2012/0056000 A1 | 3/2012 | Shores |
| 2016/0008536 A1* | 1/2016 | Gravesen ............... F16L 29/02 604/151 |
| 2016/0144105 A1* | 5/2016 | Hooven ............... A61M 5/152 604/132 |

OTHER PUBLICATIONS

International Search Report and Written Opinion for the International Patent Application No. PCT/US2019/042408, dated Mar. 27, 2020, 18 pages.

* cited by examiner

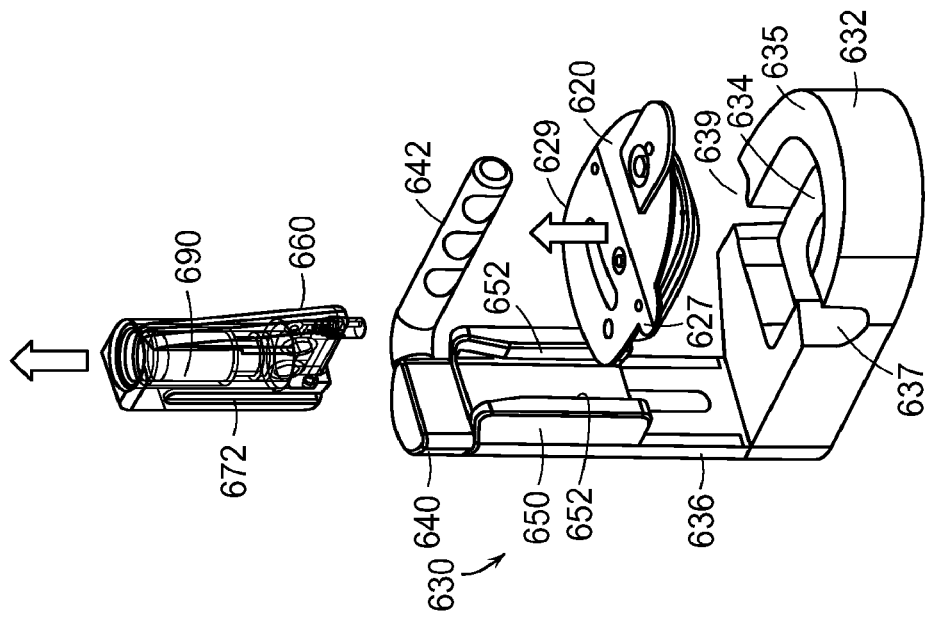
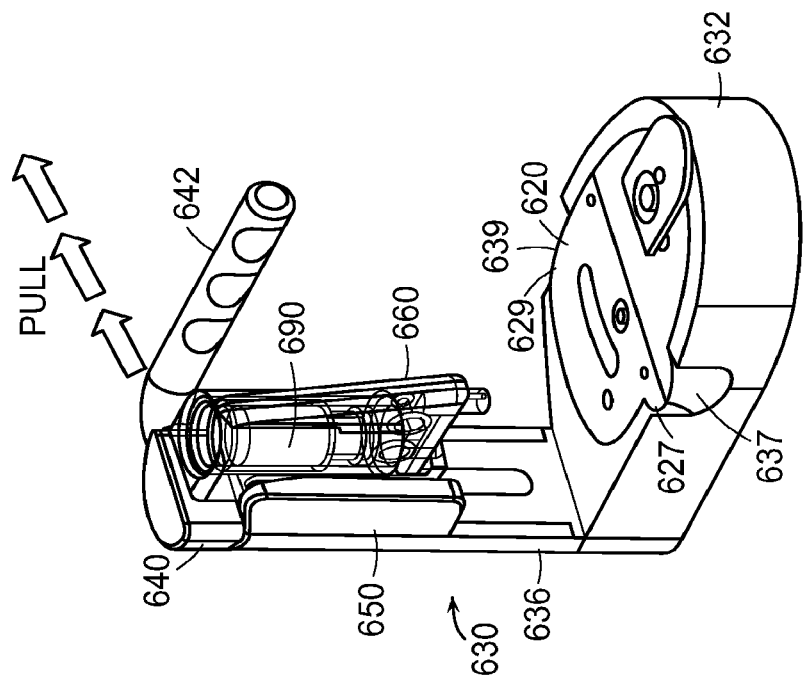

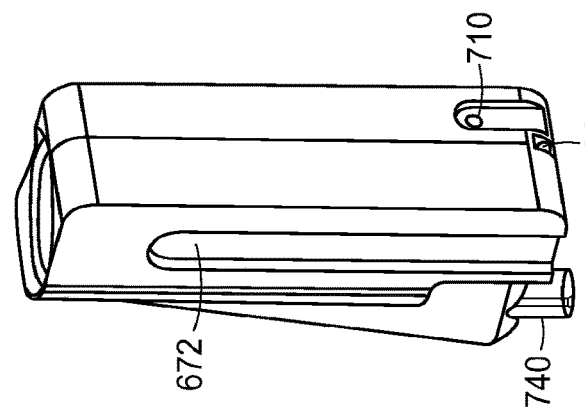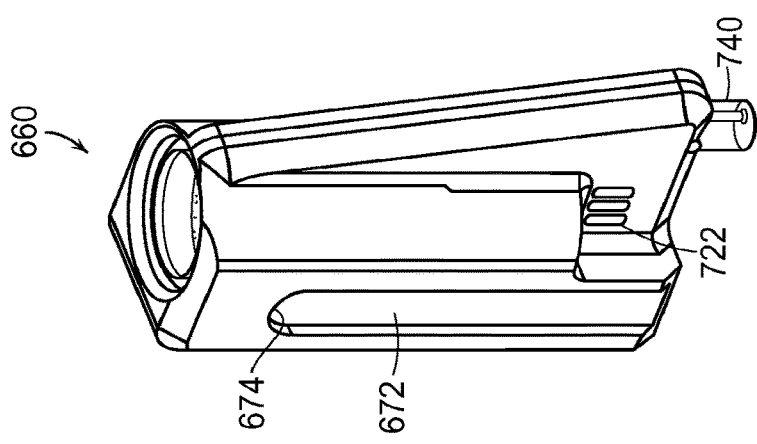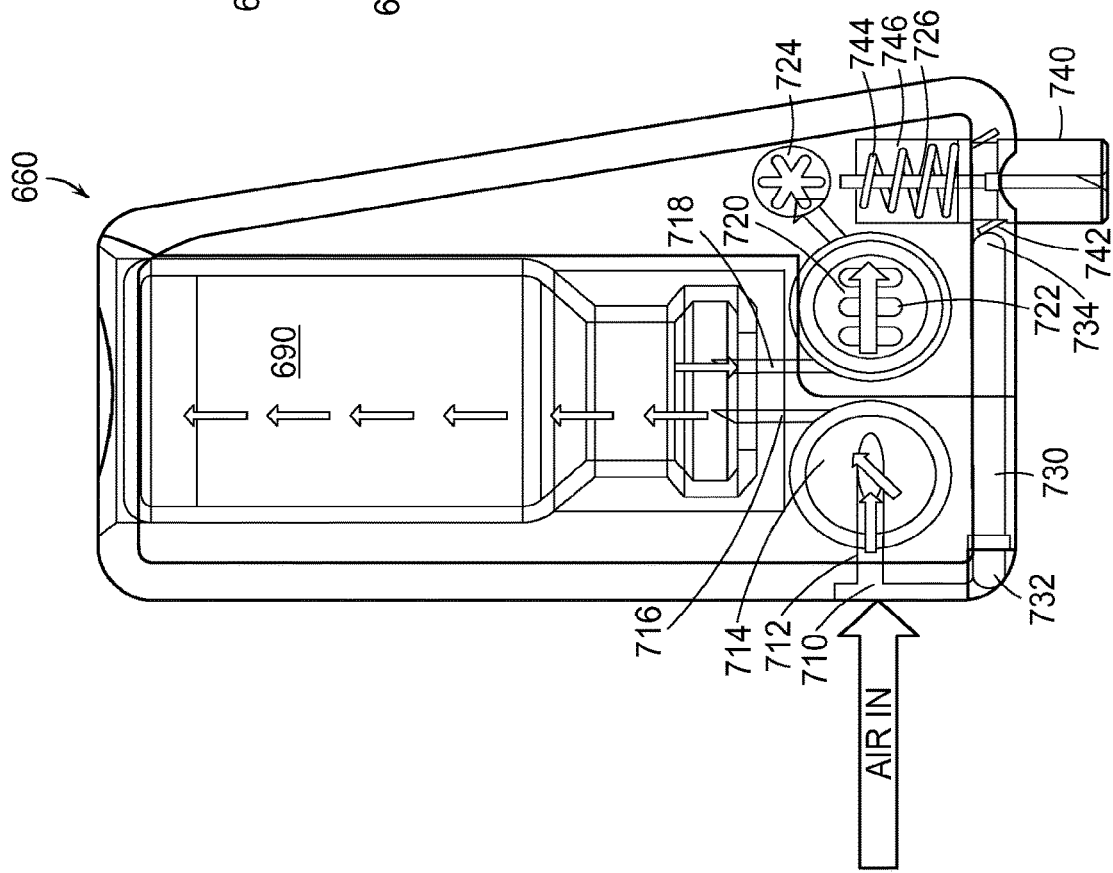

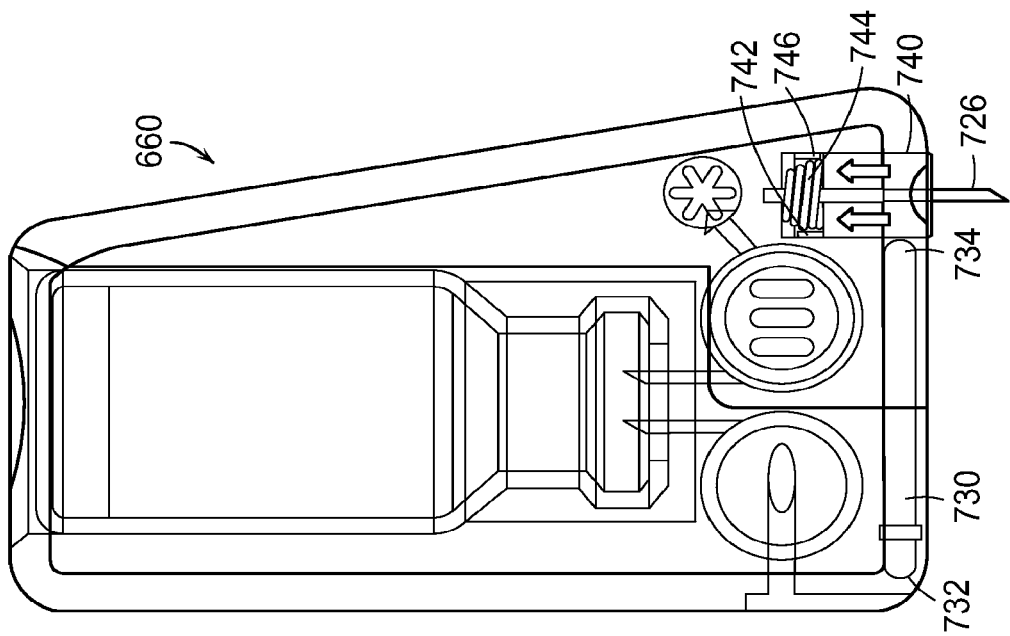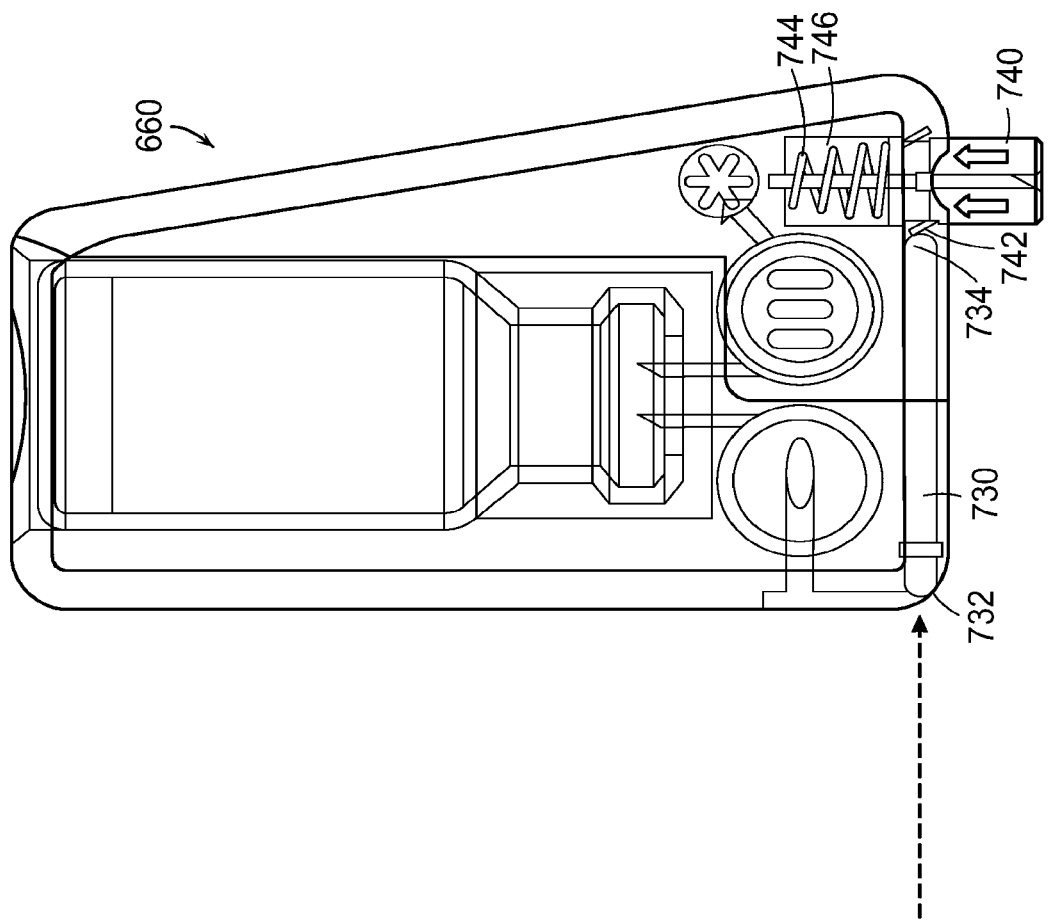

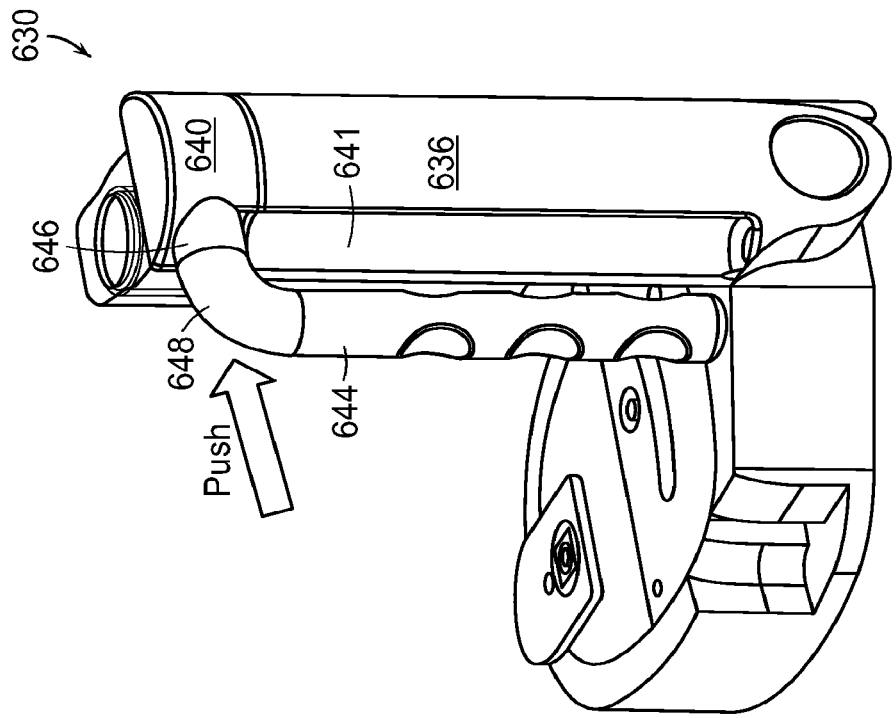
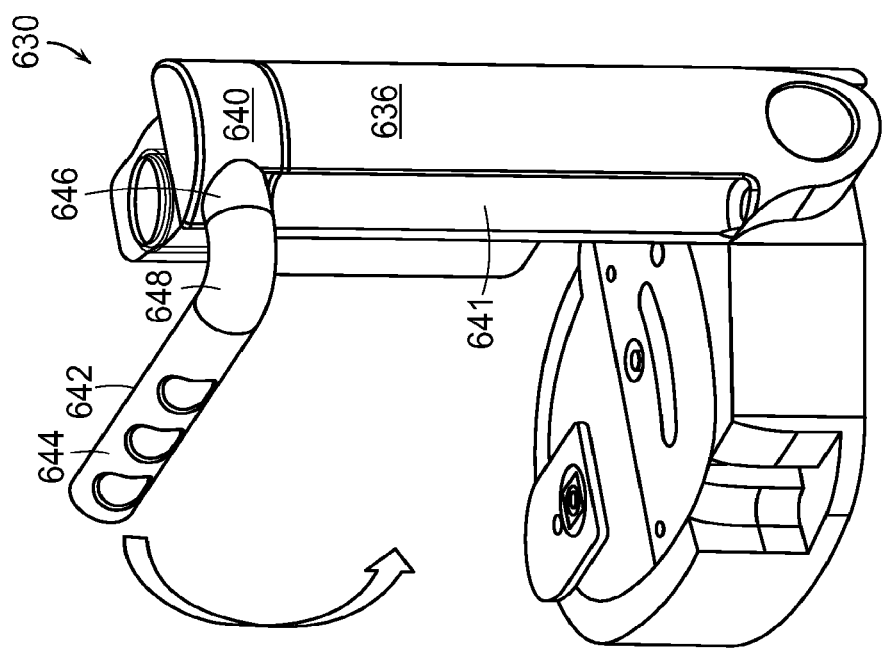

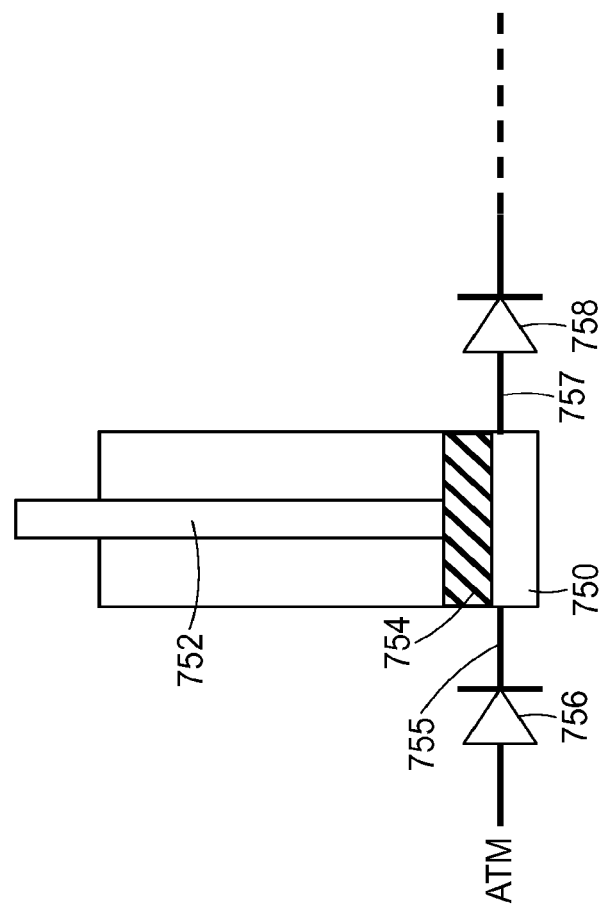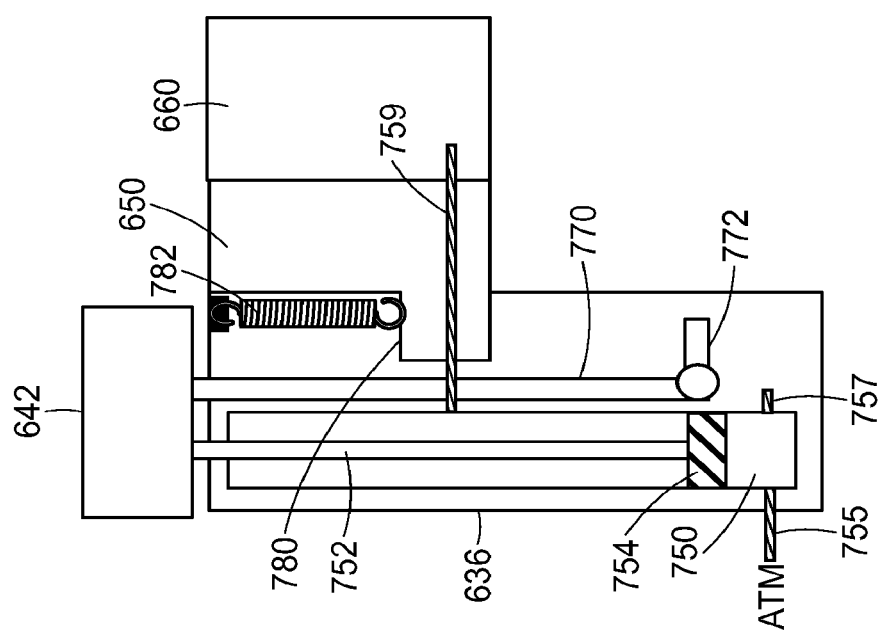
FIG. 7B
FIG. 7A

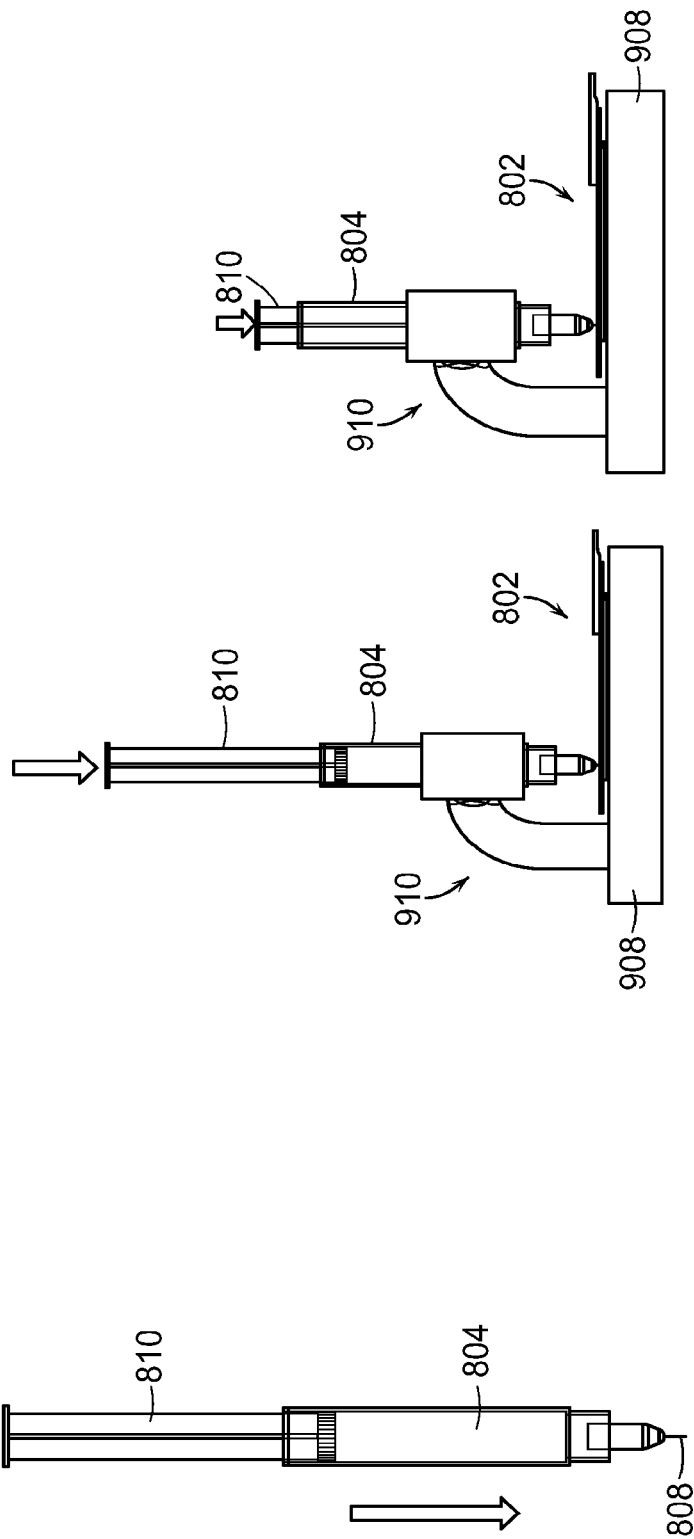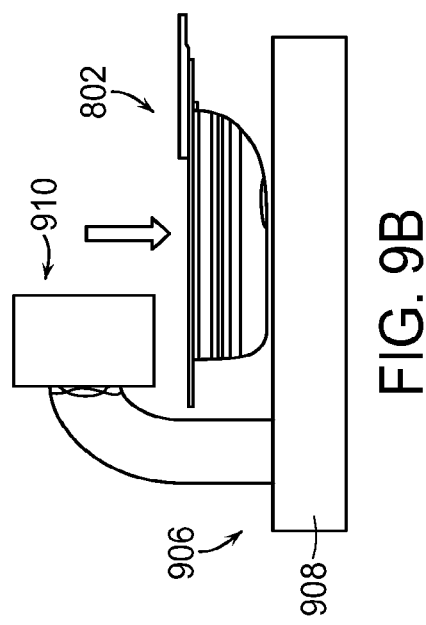

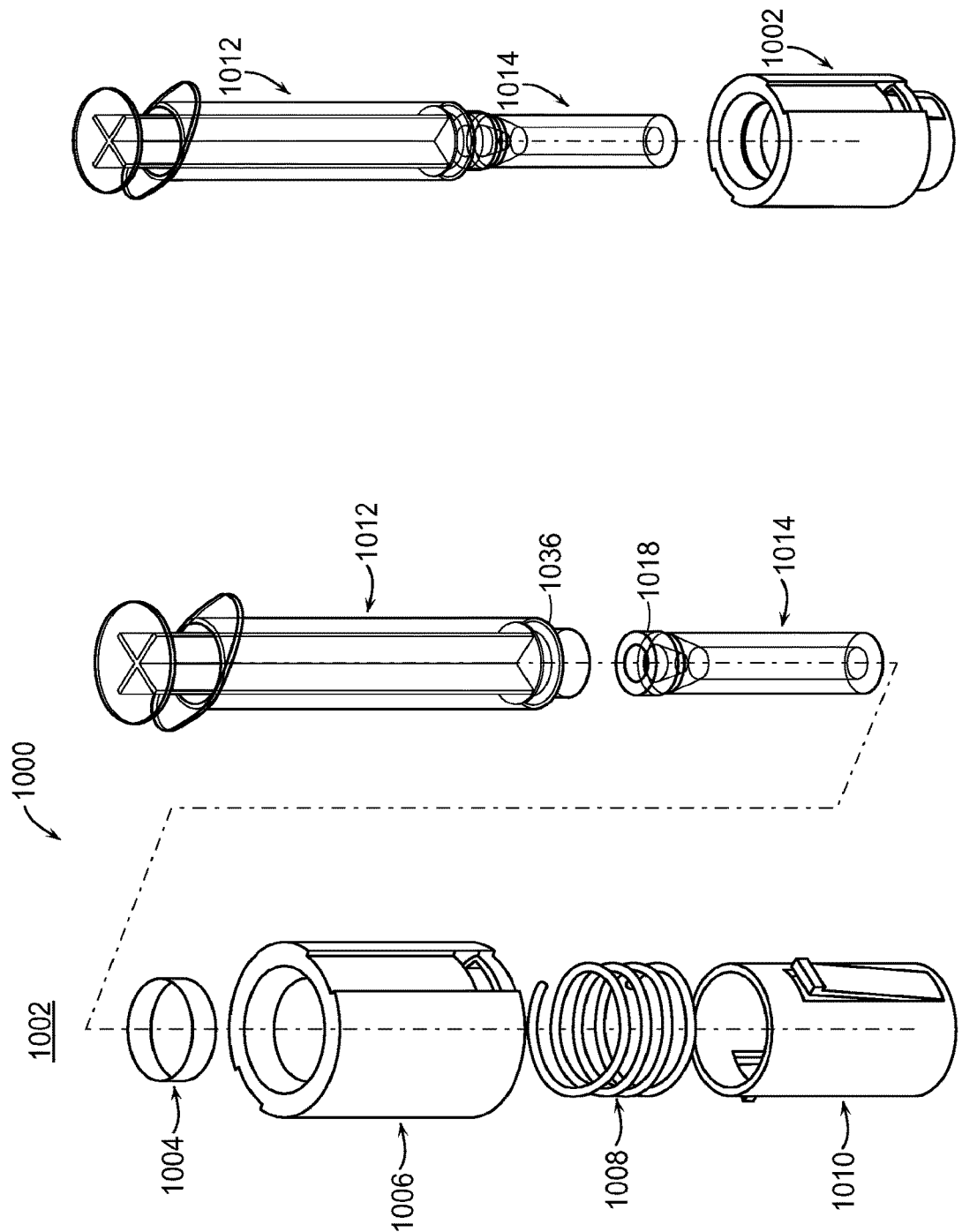

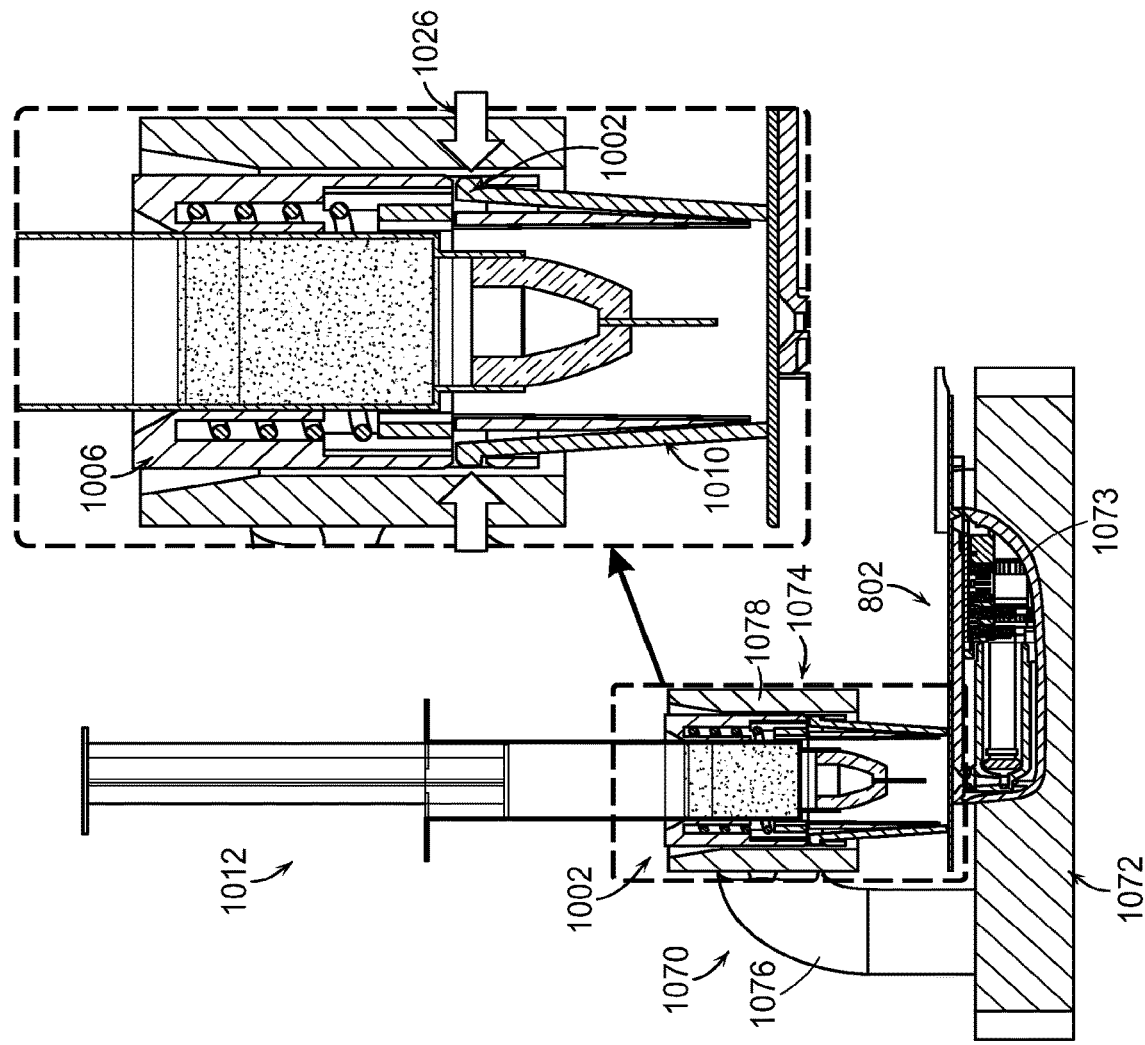
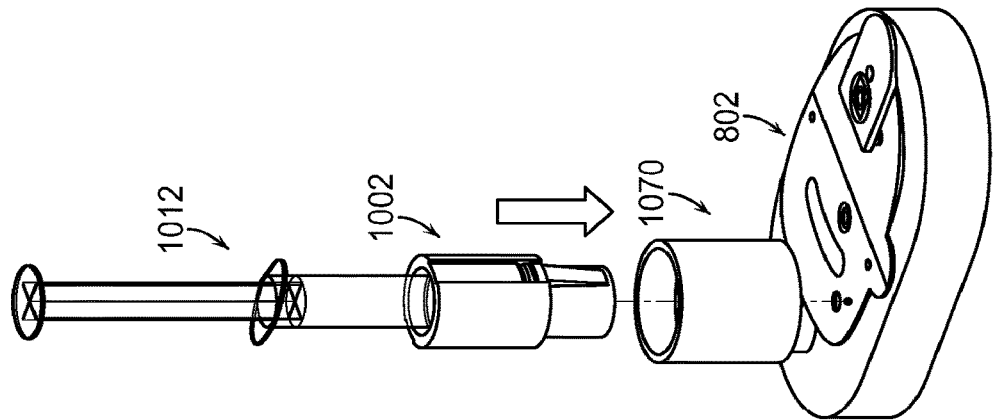
FIG. 10J
FIG. 10I

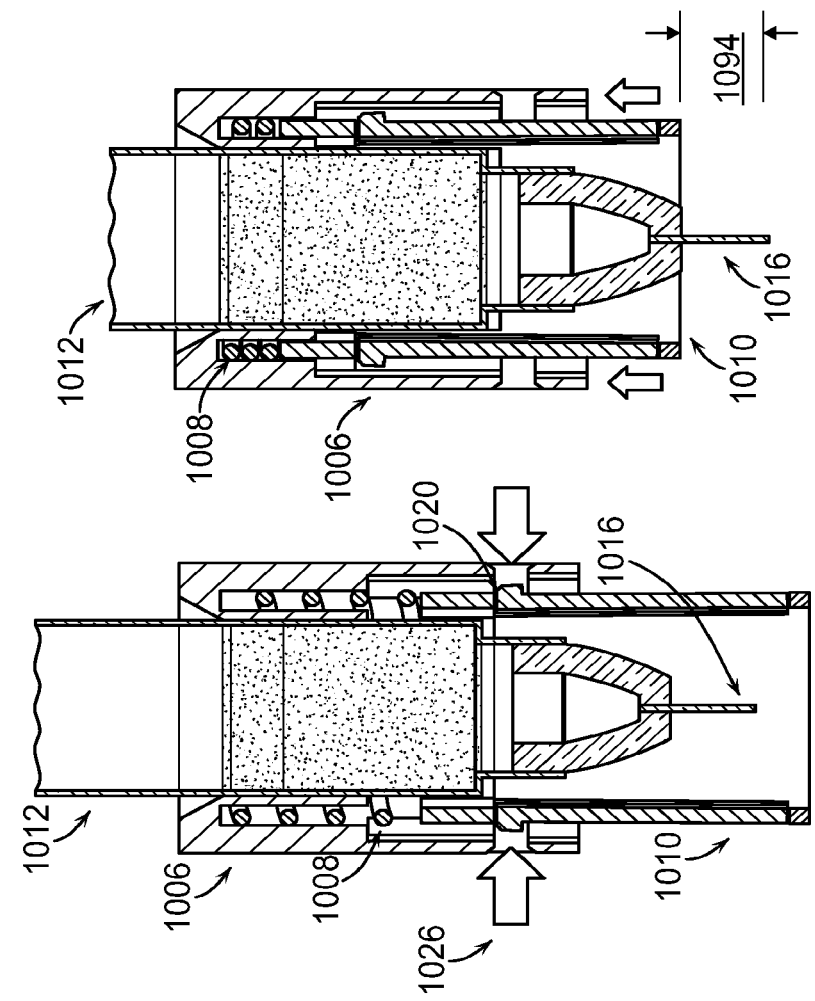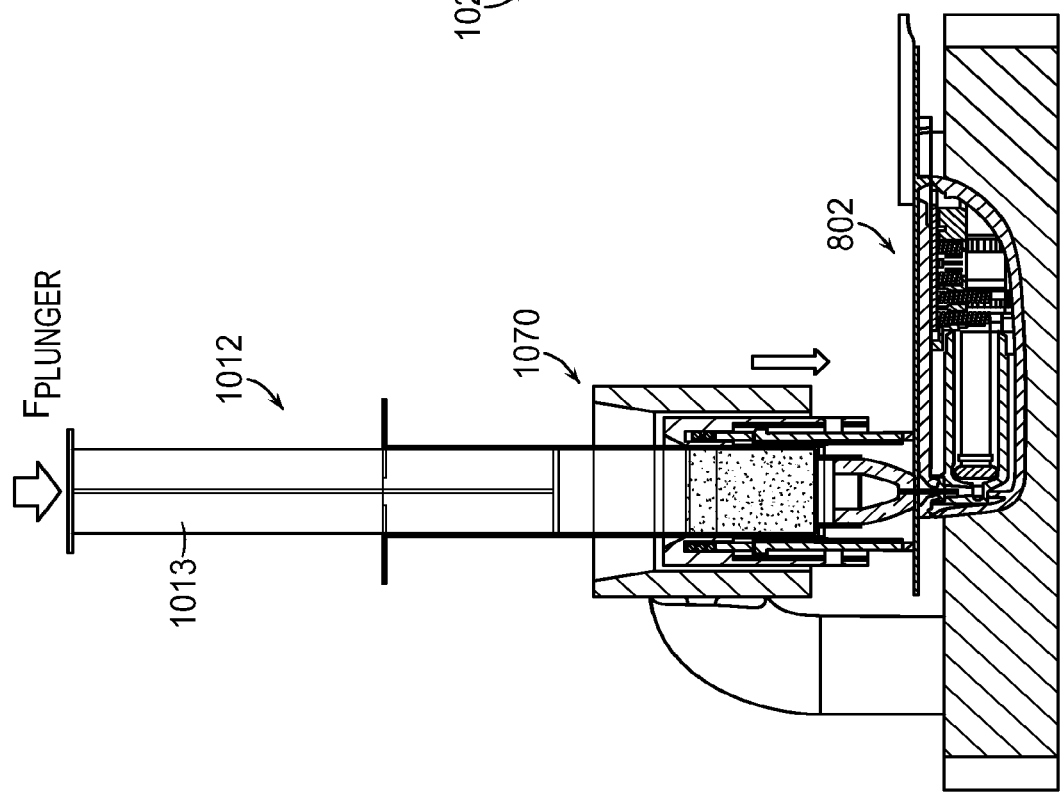

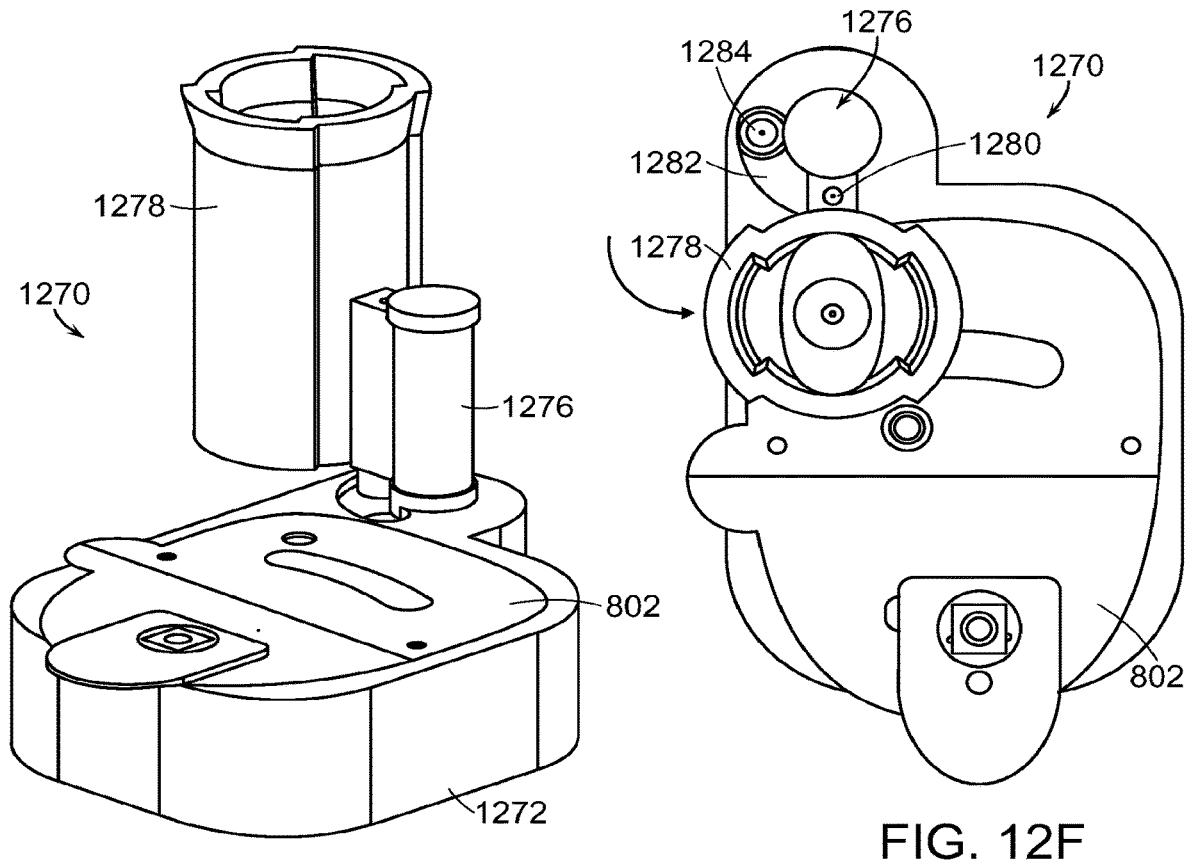
FIG. 12D
FIG. 12F
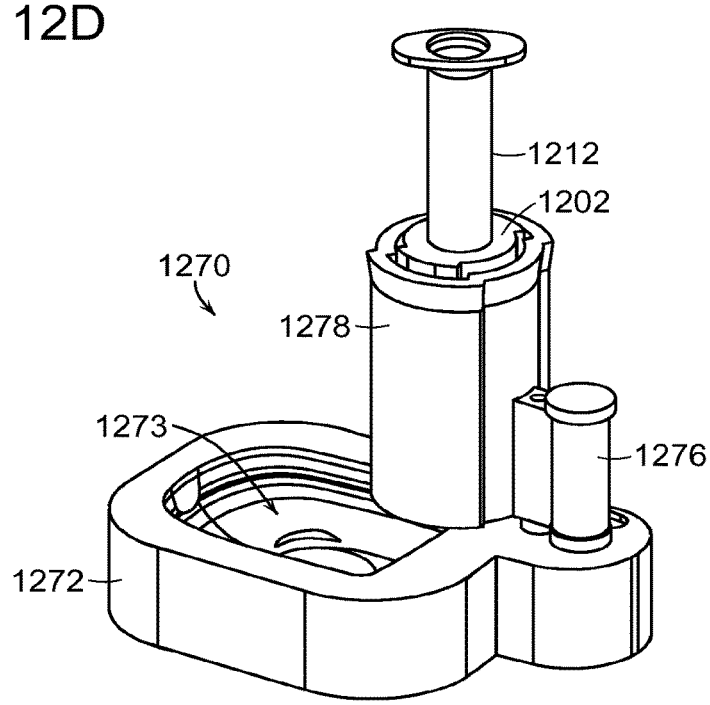
FIG. 12E

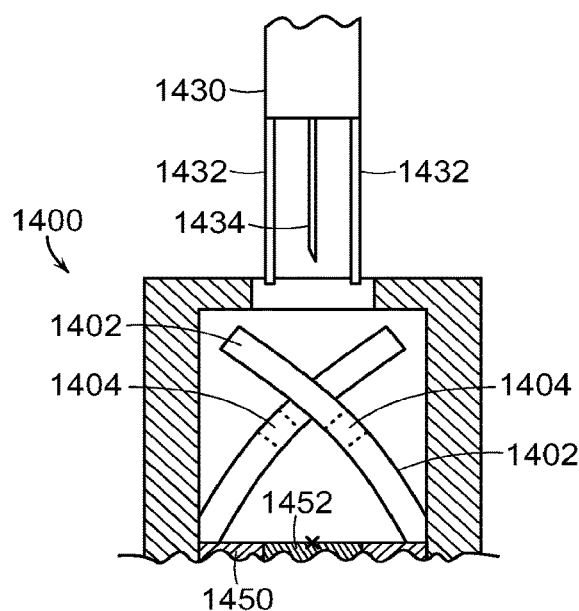
FIG. 14A
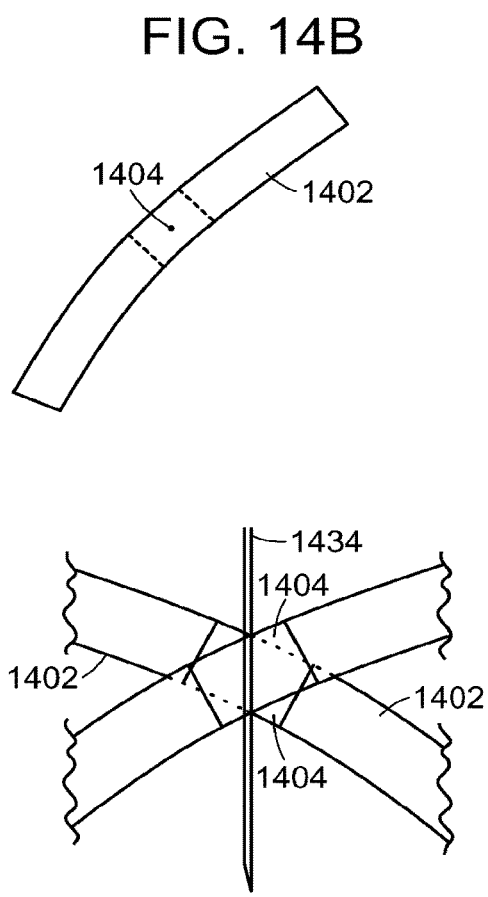
FIG. 14B
FIG. 14C

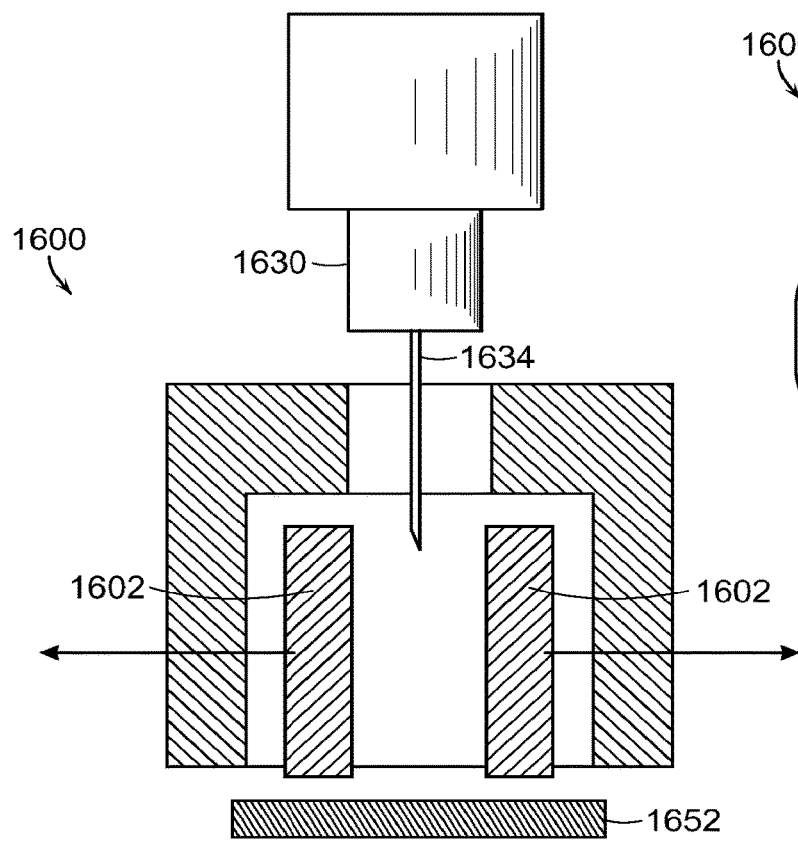
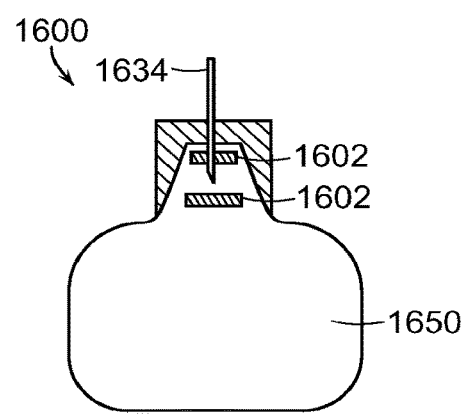
FIG. 16B
FIG. 16A

FIG. 17F
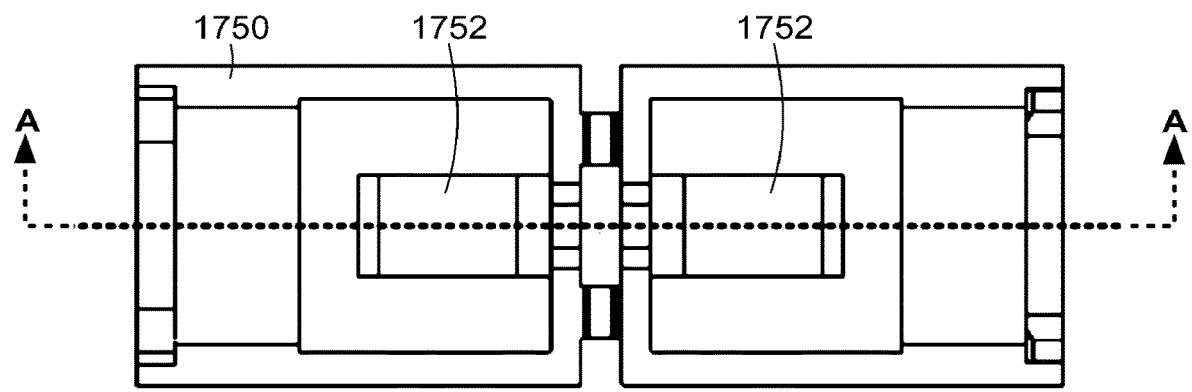
SECTION A-A
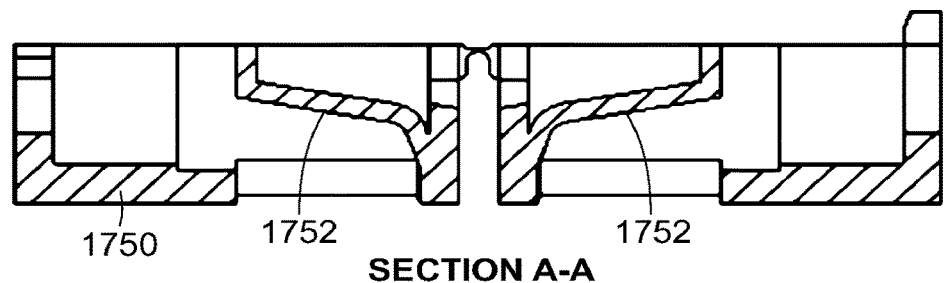
FIG. 17G

SECTION

FILLING ASSIST MECHANISMS AND KEYED INTERFACES FOR DRUG DELIVERY DEVICES

CROSS-REFERENCE TO RELATED APPLICATIONS

This application claims the benefit of U.S. Provisional Application No. 62/274,445, filed Jan. 4, 2016, U.S. Provisional Application No. 62/276,020, filed Jan. 7, 2016, U.S. Provisional Application No. 62/276,045, filed Jan. 7, 2016, U.S. Provisional Application No. 62/374,311, filed Aug. 12, 2016, U.S. Provisional Application No. 62/378,264, filed Aug. 23, 2016, U.S. Provisional Application No. 62/395,498, filed Sep. 16, 2016, and U.S. Provisional Application No. 62/407,113, filed Oct. 12, 2016, each of which is incorporated herein by reference in its entirety.

BACKGROUND

A medical device may be worn on or embedded in a body of a person to deliver medication to the person using a needle, cannula, etc., to dispense the medication from a reservoir in the medical device into the body of the person using a pump, such as a mechanical or electric pump. The medical device may be a single-use device; once the reservoir is empty, the medical device is discarded. Other medical devices may be refillable. Refillable medical devices may be more cost effective than single-use devices and may provide other benefits.

Filling single-use medical devices and/or refilling refillable medical devices, however, may present challenges. A user may need to transfer liquid drug from a liquid drug container or vial to the medical device. This may present challenges such as ensuring that the medication remains sterile before, during, and after filling. This may also present challenges such as ensuring that the correct type and/or dosage of medication is used to fill the medical device. A need therefore exists for a reliable mechanism for filling a medical device while ensuring that the correct type and/or dosage of medication is used to fill the medical device.

In addition, transferring the drug to the medical device can be a challenging task for a user as it may require precise handling of the drug in its container or vial and the medical device. In many instances, a user may be required to use a transfer device such as a syringe to withdraw the drug from its container or vial and to transfer that drug to the medical device. This may require the user to align a needle tip of a syringe with a liquid drug container or vial to withdraw the drug into the syringe and/or to align a needle tip of a syringe containing the drug with a fill port of the medical device. Properly aligning the syringe needle tip with a liquid drug container or vial and/or the fill port of a medical device can be difficult, particularly for users that may have compromised motors skills. Generally, the needle tip of the syringe must be precisely aligned in order to ensure proper transfer of the drug without spillage or waste. A need therefore exists for a more convenient and reliable mechanism for aligning a syringe needle tip with a liquid drug container or vial and/or with the fill port of a drug delivery medical device.

Further, many users of drug delivery medical devices may have limited or impaired motor skills. Such users may be at risk for being hurt by a needle that may be exposed during the drug transfer process. Accordingly, a need therefore also exists for an easy-to-use filling system that reduces the likelihood of being hurt by an exposed needle.

There is therefore a need for improved filling or refilling devices and techniques that may be used in conjunction with drug delivery medical devices.

BRIEF DESCRIPTION OF THE DRAWINGS

FIGS. 7A through 7L schematically illustrate steps in a method of using the system of FIGS. 6A through 6U.

FIGS. 9B through 9D illustrate a fluid transfer process using the alignment device of FIG. 9A.

FIGS. 10A through 10M illustrate a system including a skirt assembly and alignment device to assist in filling a medical device.

FIGS. 12A through 12H illustrate another system including a skirt assembly and alignment device to assist in filling a medical device.

FIGS. 14A through 14C show a cap for a liquid drug container or medical device and a corresponding needle hub, wherein the cap has one or more bendable features or doors.

FIGS. 16A and 16B show another embodiment of a cap for a liquid drug container or medical device and a corresponding needle hub, wherein the cap has one or more moveable magnetic features.

FIGS. 17A through 17H illustrate a system comprising a syringe, needle hub, and container or vial adapter or cap in accordance with another embodiment.

DETAILED DESCRIPTION

Figure 1A:
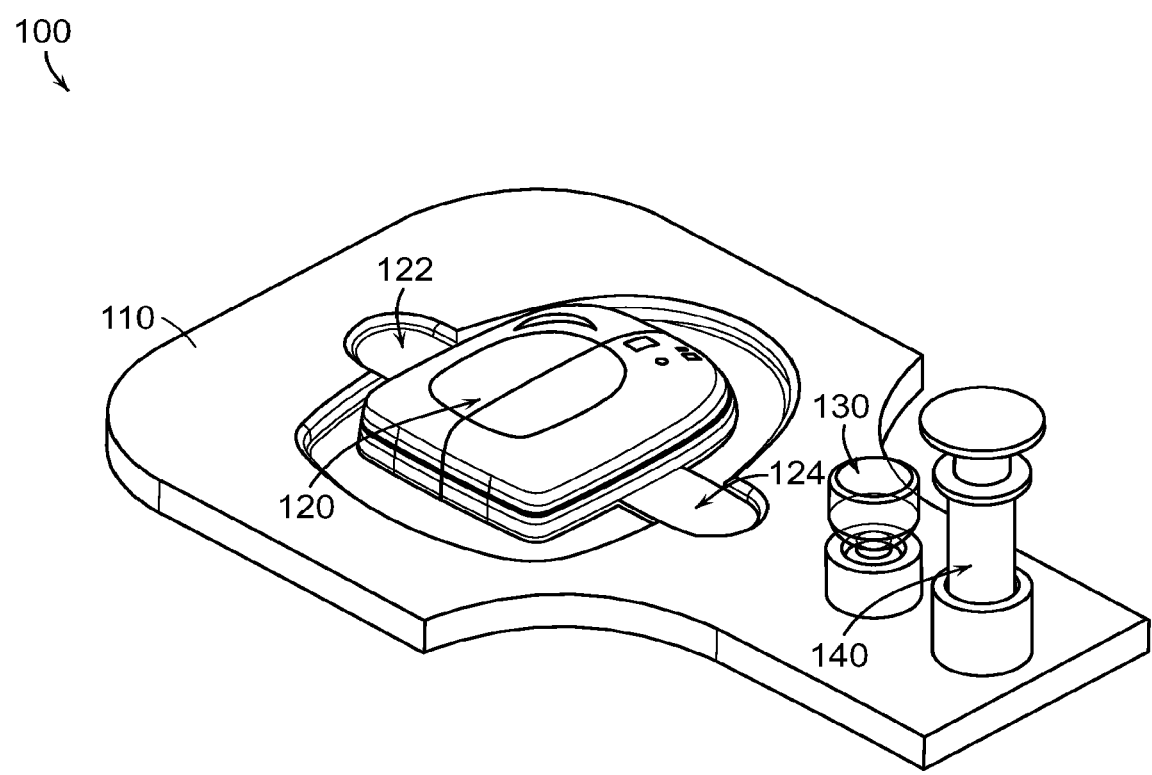
FIG. 1A shows a system for filling a drug delivery device comprising a baseplate and a pumping mechanism.

This disclosure presents various systems, components, and methods for filling a medical device with a drug. Each of the systems, components, and methods disclosed herein provides one or more advantages over conventional systems, components, and methods.

Various systems, components, and methods disclosed herein provide for filling a drug delivery medical device with a fluid drug in a more precise and efficient manner. Various embodiments enable users with compromised motor skills to more easily align a needle tip of a syringe with a fill port of the drug delivery medical device, thereby reducing the likelihood of damaging the needle tip and/or not transferring a proper amount of fluid (e.g., a desired drug dosage) from the syringe to the drug delivery medical device.

Various systems, components, and methods disclosed herein provide a safety device that can minimize exposure of a needle during use of a syringe to fill a drug delivery medical device. The safety device can be a skirt assembly that couples to a syringe. The skirt assembly can provide a shield around a needle when the syringe is filled with a drug and when the drug is transferred to the drug delivery medical device. As a result, the likelihood a user is hurt by the needle during the drug transfer process is significantly reduced.

Certain medical devices and fluid transfer systems, such as infusion pumps and syringes, are specific to a particular type of drug. Various systems, components, and methods disclosed herein help ensure that the correct drug is used with the correct medical device or system. For example, one medical device may be supplied for use with U200 insulin, while another medical device may be supplied for use with U100 insulin. If a medical device for U100 insulin were to be filled with a different drug, such as U200 insulin, the labeling would be incorrect and there would be a risk of the incorrect number of doses being administered. In various systems, components, and methods disclosed herein, a needle hub is designed with one or more keying features or structure to mate with one or more corresponding keying features or structure associated with the liquid drug container from which drug is supplies and/or with the medical device to which drug is to be transferred. The one or more corresponding keying features or structure may be in a cap that attaches to or is integrated with the liquid drug container and/or the medical device. This would greatly reduce the risk of filling a medical device with the incorrect drug.

In various systems, components, and methods disclosed herein, a cap that attaches to or is integrated with the liquid drug container and/or the medical device may include one or more features that cover the septum or other entryway into the liquid drug container and/or the medical device. When a needle hub with the proper mating keying features or structure is inserted into the cap, it engages the one or more features to uncover the septum or entryway, thereby permitting access to the medication.

The keying features and/or structures of the needle hub and corresponding liquid drug container cap and/or medical device cap may include a size and/or shape of the component, one or more protrusions, projections, posts, ridges, tabs, proud features, prongs, keys, electrical contacts and/or circuits, slots, cutouts, recesses, reliefs, holes, and/or keyholes, and/or specific orientations thereof. A needle hub of the wrong type is not permitted to enter the liquid drug container cap and/or medical device cap. With the correct needle hub, a person may mate the syringe with the liquid container, withdrawn medication therefrom, and thereafter mate the syringe with the medical device and dispense the medication thereto, thereby filling the medical device. Thus, a drug may be transferred from a liquid drug container (e.g., a vial) to a medical device (e.g., a drug delivery medical device) while preventing access to and transfer of the incorrect drug. The person conducting the transfer does not have the ability to access the drug in the liquid drug container with an incorrect needle hub or the ability to fill the medical device using an incorrect needle hub. This minimizes error as well as tampering.

Various embodiments disclosed herein include systems, components, and methods for refilling a medical device while ensuring that the correct medication (i.e., a specific medication prescribed by a physician and/or other intended medication) is used. FIG. 1A illustrates a system 100 that includes a baseplate 110, a medical device ("pod") 120, a liquid drug container 130 filled with a liquid drug, and an active pumping mechanism 140. The pumping mechanism 140 may be a suitable pump such as an infusion pump, and the liquid drug container 130 (and other liquid drug containers disclosed herein) may be any suitable drug container, vial, cartridge, auto injector, pen, or syringe (pre-filled or empty). The medical device 120 may be a drug delivery device to be worn on or embedded in a body of a person to deliver medication to the person using a needle, cannula, etc., to dispense the medication from a reservoir in the medical device 120 into the body of the person using a pump, such as a mechanical or electric pump. An example medical device 120 is the medical device of the OmniPod® System (Insulet Corporation, Billerica, Mass.). The medical device 120 can be a drug delivery device such as those described in U.S. Pat. Nos. 7,303,549, 7,137,964, or U.S. Pat. No. 6,740,059, each of which is incorporated herein by reference in its entirety.

As described in greater detail below, a user may mate the liquid drug container 130 with the baseplate 110, mate the medical device 120 with the baseplate 110, and then fill (including refill) the reservoir of the medical device 120 by operating the pumping mechanism 140 to thereby transfer medication from the liquid drug container 130 into the medical device 120. One or more features of the baseplate 110 in the areas at which the medical device 120 and liquid drug container 130 mate with the baseplate 110—referred to herein as "keying features" "keying structure" or "nests"—may allow the medical device 120 and liquid drug container 130 to mate while preventing other types of medical devices and/or liquid drug containers from mating. For example, in FIG. 1A, the medical device 120 features two keying features 122, 124 on either side that mate with corresponding keying features 112, 114 in the baseplate 110. Each keying feature of the baseplate 110 may be a positive keying feature (i.e., it nests into a keying feature of the medical devicer 120 or liquid drug container 130) or a negative keying feature (i.e., a keying feature of the medical device 120 or liquid drug container 130 nests into a keying feature of the base plate) that allows positive engagement to the baseplate only if keyed properly.

In some embodiments, the keying features on the medical device 120 and/or liquid drug container 130 are integrated with the medical device 120 and/or liquid drug container 130 and are created as the medical device 120 and/or liquid drug container 130 is created or manufactured. For example, the medical device 120 and/or liquid drug container 130 may include an injection-molded housing that includes the keying features. In other embodiments, the keying features on the medical device 120 and/or liquid drug container 130 are not integrated with the medical device 120 and/or liquid drug container 130; in these embodiments, a cap or other attachment includes the keying features and is attached to the medical device 120 and/or liquid drug container 130 using an adhesive, mechanical means such as screw threads or a snap-on mechanism, or any other suitable means. The cap may not be able to be removed from the medical device 120 and/or liquid drug container 130 without destroying or disabling the medical device 120 and/or liquid drug container 130.

In some embodiments, the keying features of the medical device 120 visually resemble those of the liquid drug container 130 to aid in user selection of the medical device 120 and liquid drug container 130, particularly in cases in which the user selects the medical device 120 and/or liquid drug container 130 from a plurality of different types of medical devices 120 and/or liquid drug containers 130. The resemblance of the keying features may be based on a similar number of keying features, a similar placement of keying features, a similar color of keying features, a similar size of keying features, a similar shape of keying features, or any other suitable similarity. For example, each of the medical device 120 and liquid drug container 130 may have three keying features, such as posts, disposed at 0 degrees, 120 degrees, and 240 degrees around a surface that mates with the baseplate 110. Other types of medical devices 120 and/or liquid drug containers 130 may have two or fewer or four or more keying features and/or keying features disposed in different positions, allowing the user to distinguish between types.

Figure 1B:
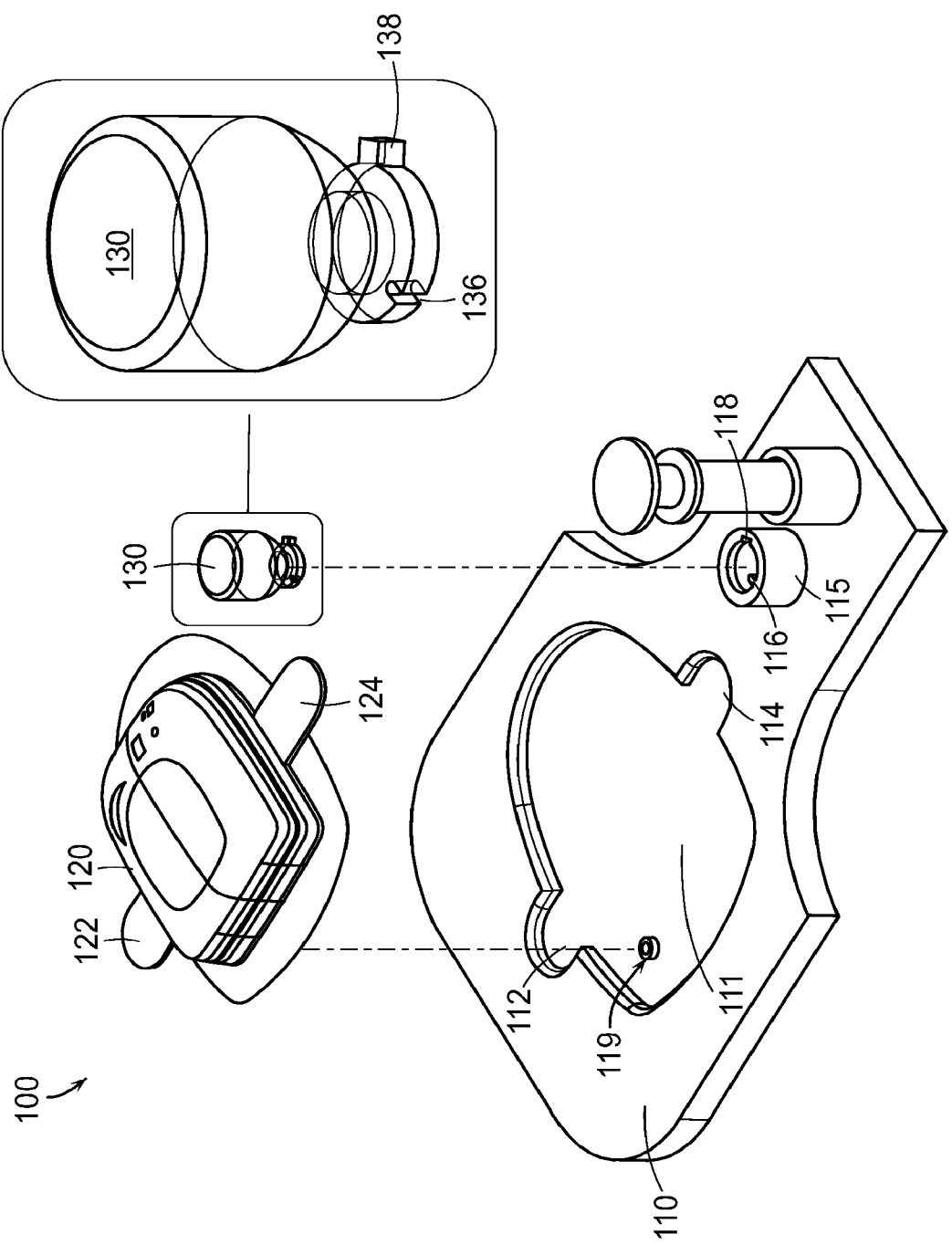
FIG. 1B shows the system of FIG. 1A showing a keying arrangement for mating a drug container or vial to the baseplate.

FIG. 1B illustrates another view of the system 100 in which the medical device 120 and liquid drug container 130 are separated from the baseplate 110. In this embodiment, keying features 112, 114 in the form of keying recesses or keying reliefs are shown on the baseplate 110; corresponding keying features 122, 124 in the form of keying tabs on the medical device 120 mate with the keying features 112, 114, i.e., the keying tabs 122, 124 fit into the keying recesses 112, 114. The positioning and sizes of the keying features on the medical device 120 and the baseplate 110 are such that the medical device 120 must be in the correct position relative to the baseplate 110 so that the keying tab 122 fits into the keying recess 112 while the keying tab 124 fits into the keying recess 114, allowing the user to move the medical device 120 into a fully seated condition in the medical device nest 111 in baseplate 110 in which drug may be dispensed into the reservoir of the medical device 120.

The liquid drug container 130 also includes keying features; as shown in FIG. 1B, the keying geometry of the liquid drug container 130 comprises keying features 136, 138 that mate with corresponding keying features 116, 118 in the medication nest 115 in the baseplate 110. In this illustrated embodiment 100, the keying geometry of the liquid drug container 130 comprises keying features 136, 138 in the form of a keying recess 136 and a keying tab 138 that mate with corresponding keying features 116, 118 in the form of a keying tab 116 and a keying recess 118 in the medication nest or liquid drug container nest 115 in the baseplate 110. The keying tab 116 fits in the keying recess 136, while the keying tab 138 fits in the keying recess 118. The positioning and sizes of the keying features on the liquid drug container 130 and the baseplate 110 are such that the liquid drug container 130 must be rotated into the correct position relative to the baseplate 110 so that the keying tab 116 fits into the keying recess 136 while the keying tab 138 fits in the keying recess 118, allowing the user to move the liquid drug container 130 into a fully seated condition on the baseplate 110 in which drug may be dispensed from the liquid drug container 130.

Figure 1C:
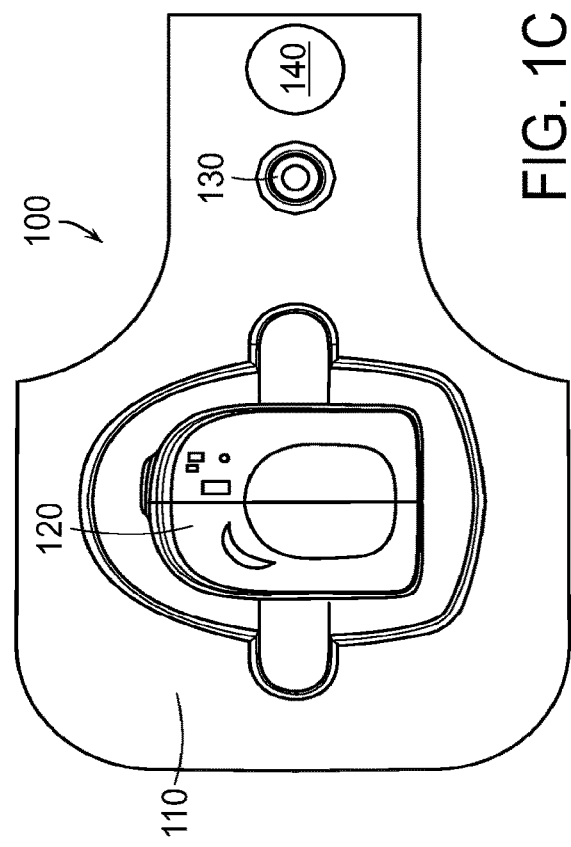
FIG. 1C shows a top view of the system of FIG. 1A.
Figure 1D:
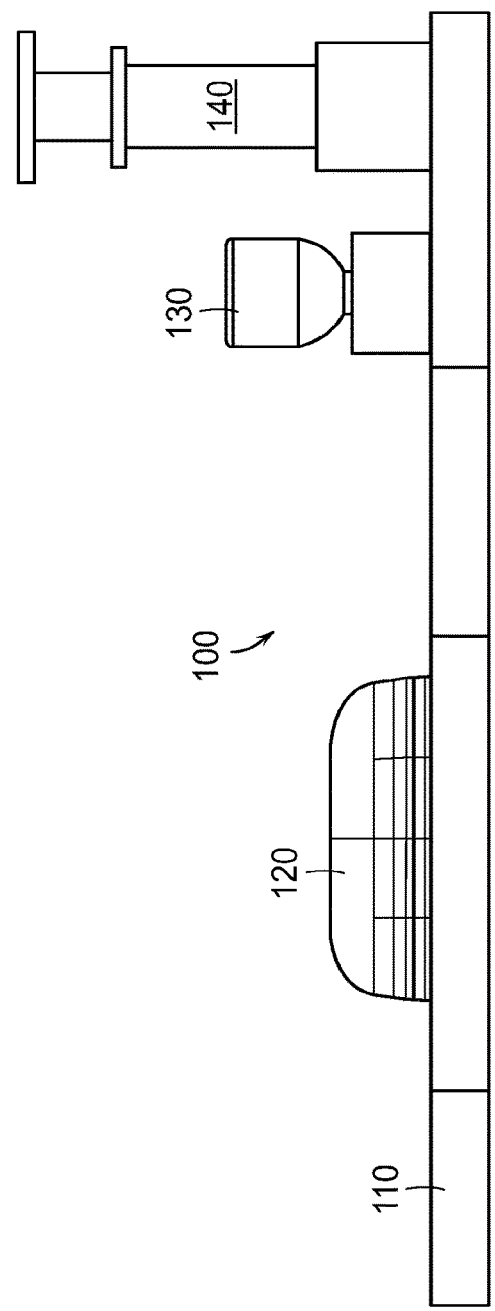
FIG. 1D shows a side view of the system of FIG. 1A.

FIG. 1B also illustrates a fill port 119 on the baseplate 110 that mates with a corresponding fill port on the medical device 120. FIGS. 1C and 1D illustrate top and side views, respectively, of the system 100.

Figure 2:
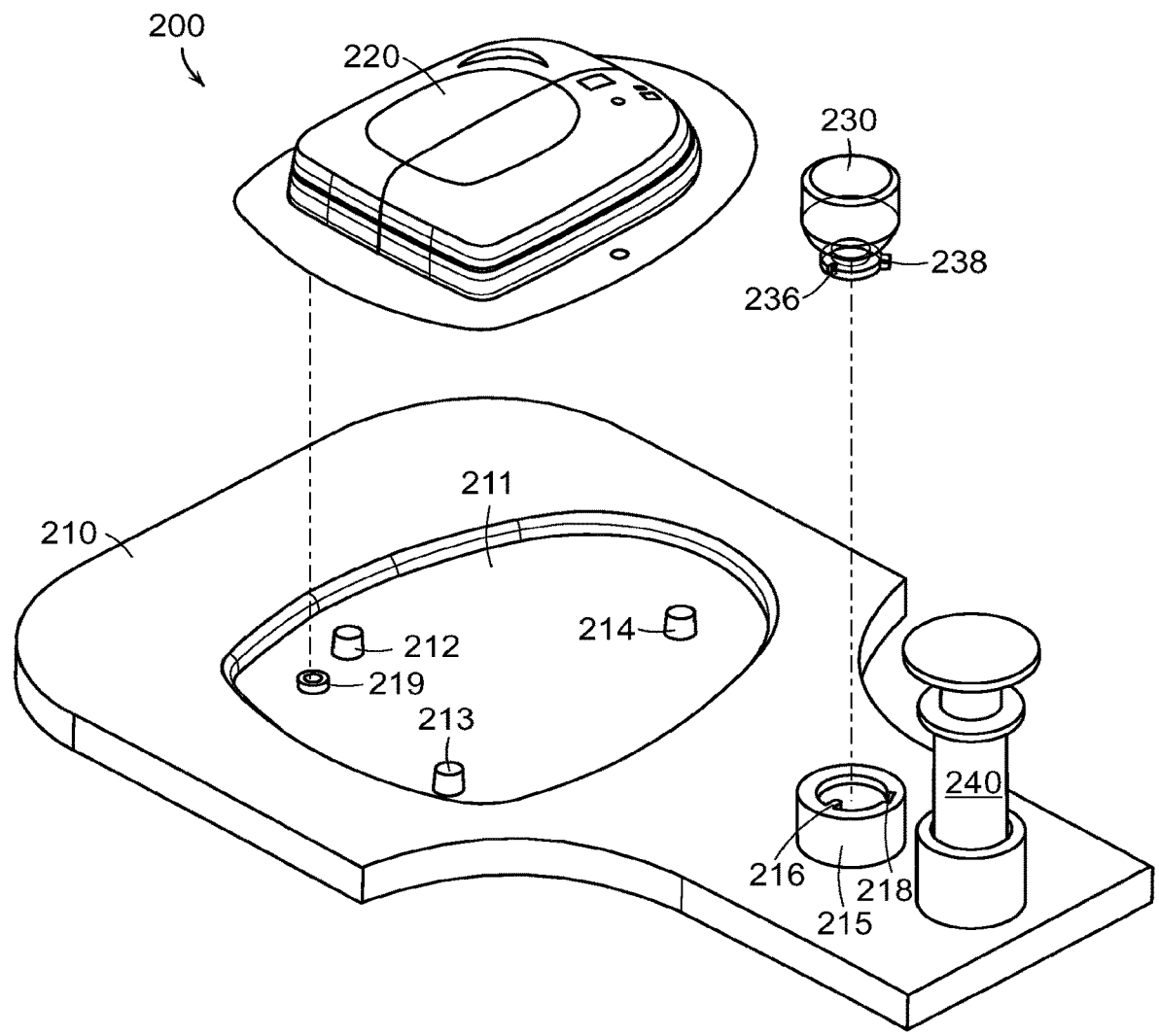
FIG. 2 shows another embodiment of a system for filling a drug delivery device comprising a baseplate and a pumping mechanism.

FIG. 2 illustrates an embodiment in the form of a system 200 in which the baseplate 210 includes one or more keying features 212, 213, 214 in the form of proud features or prongs in the medical device nest 211. The medical device 220 may include corresponding keying features in the form of keying recesses or keying reliefs in the same number and orientation as the keying features 212, 213, 214 such that the medical device 220 may be placed on the baseplate 210 to thereby mate with it. If a user attempts to seat a medical device that does not have corresponding reliefs for the keying features 212, 213, 214 of the baseplate 210, that medical device may not be able to be placed on the baseplate 210, in which case the fill port 219 will not connect to that medical device.

Different patterns or placements of the keying features on the medical device nest 211 and the liquid container nest 215 may be used for different types of medication, different instances of medication, different doses of medication, or any other difference. For example, if a patient is prescribed a medication having a particular strength of effect, that medication at that strength may be distributed using a first container type that includes a first set of physical keying features. Another medication of the same type as the first but having a different strength of effect may be distributed using a second container type that includes a second set of physical keying features different from that of the first. A baseplate may accept containers of the first type but not the second because it includes corresponding features in its medication or liquid container nest that mate with the first container type but not the second.

In some embodiments, the medical device is a single use or single-refill device. In these embodiments, the baseplate includes a one-way feature to hold a liquid drug container after insertion. Upon the attempt to remove the liquid drug container, the manifold is functionally compromised.

Figure 3:
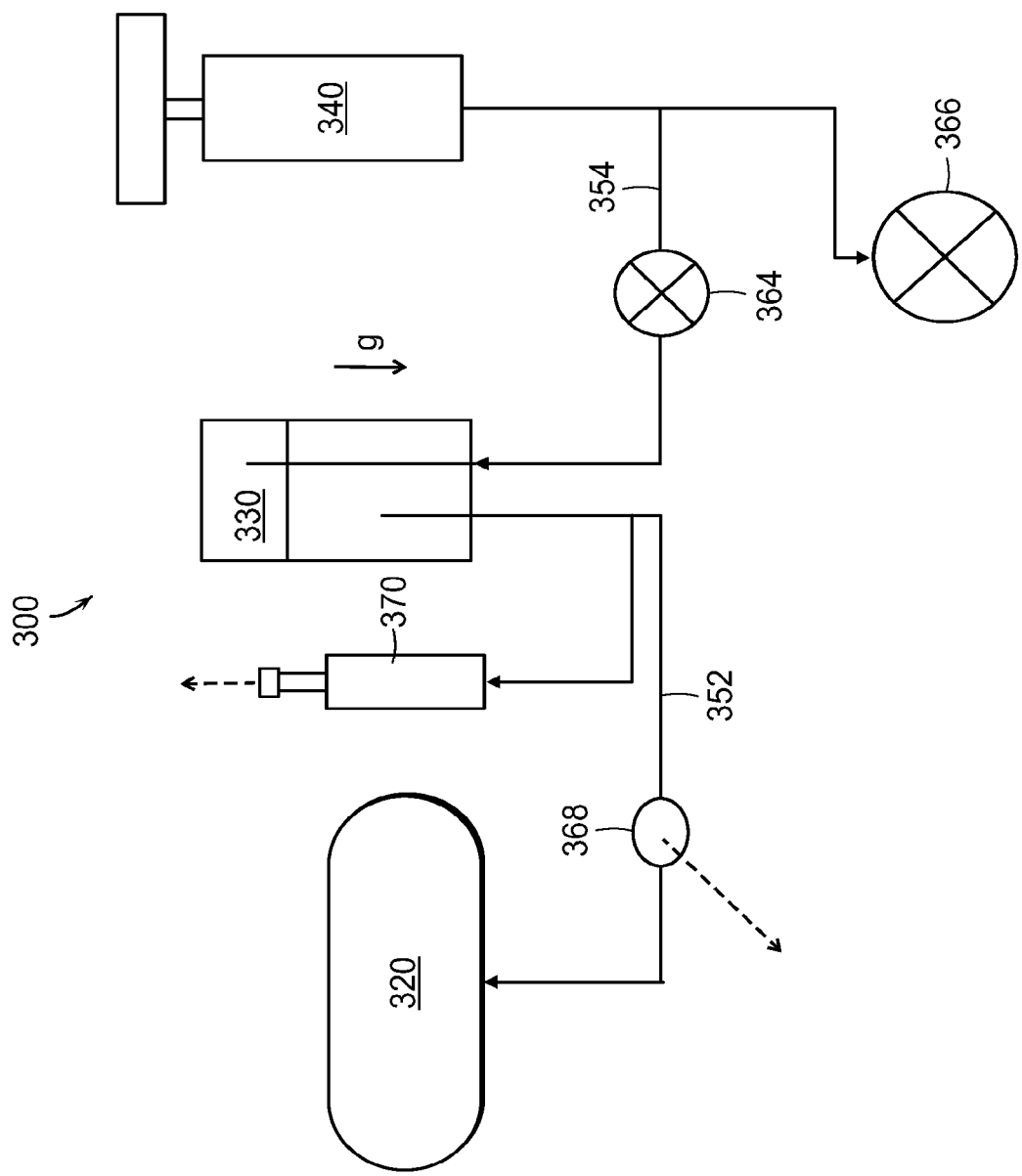
FIG. 3 shows a schematic version of a mechanism usable with a system such as that shown in FIGS. 1A through 1C or FIG. 2.

FIG. 3 illustrates a system 300 for refilling a reservoir of a medical device 320 in accordance with embodiments disclosed herein. A drug reservoir or vial or liquid drug container 330 (e.g., one of the liquid drug containers 130, 230 described above) includes a quantity of medication. Once the liquid drug container 330 is mated to the baseplate (e.g., one of the baseplates 110, 210 described above), it may be in fluid communication with the reservoir in the medical device 230 via a first fluid channel 352 and in fluid communication with a pumping mechanism 340 via a second fluid channel 354. Both the first fluid channel 352 and the second fluid channel 354 may be sterile; in these embodiments, the fluid pumped into the liquid drug container 330 may be in contact with the medication. The medication may move through the first fluid channel 352 into the medical device 320. The fluid in the second fluid channel 354 may be any gas or liquid.

In various embodiments, including the systems 100, 200, 300 the patient may activate the pumping mechanism 140, 240, 340, which may comprise a mechanical, electrical, gas-driven, or any other suitable type of pump. The pump enables variable fill (e.g., air filled and graduated). The pump may pump fluid into the liquid drug container 130, 230, 330 to thereby increase the pressure inside the liquid drug container 130, 230, 330 and force the medication from the liquid drug container 130, 230, 330 to the medical device 120, 220, 320. A check valve 364 may be used to prevent backflow from the liquid drug container 130, 230, 330 to the pumping mechanism 140, 240, 340. Another check valve 366 may be used to prevent over-pressure in the system; in one embodiment, this check valve 366 cracks at approximately 30 PSI. A hydrophobic vent 368 may be placed in the first fluid path or channel 352 between the liquid drug container 330 and the medical device 320 to allow air or other gas (but not the liquid drug) to exit the first fluid path or channel 352. Such a vent may be made of Tyvek or other suitable material.

Optionally, the system may include a visual indicator 370 that indicates the degree to which the reservoir in the medical device 320 is full. The patient may use the visual indicator 370 to fill the reservoir in the medical device 320 to any degree. The visual indicator 370 may include (for example) hash marks and/or elements that spring up or otherwise activate to signify a complete fill of the reservoir of the medical device 320.

Figure 4:
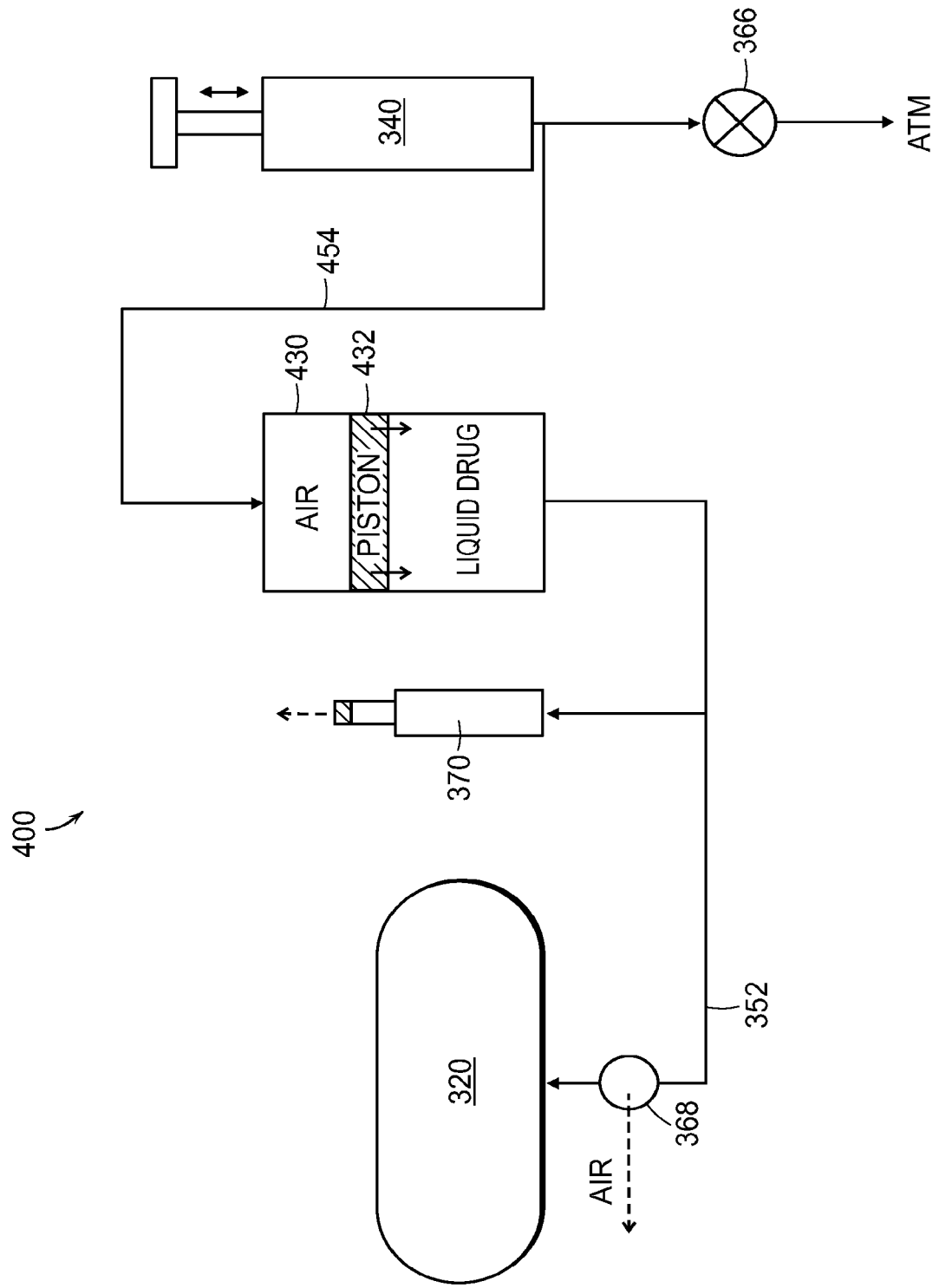
FIG. 4 shows a schematic version of another mechanism usable with a system such as that shown in FIGS. 1A through 1C or FIG. 2.

FIG. 4 illustrates an alternative embodiment in the form of a system 400 with many of the same components as the system 300. In some embodiments, as illustrated in FIG. 4, the liquid drug container 430 is in the form of a cartridge or syringe comprising a plunger or piston 432 or other membrane that separates the fluid (e.g., air) pumped into the liquid drug container 430 from the medication. In these embodiments, the second fluid channel 454 between the pump 340 and the container 430 may not be sterile. Because the membrane, plunger, or piston 432 separates the potentially non-sterile fluid (e.g., air) from the pumping mechanism 340 from the sterile drug in the liquid drug container 430, the second fluid channel 454 need not be sterile. A check valve between the pumping mechanism 340 and the liquid drug container 430 may or may not be present on the non-sterile path or second fluid channel 454.

In some embodiments, the medication may be transferred by pressuring a bottle with air to cause the medication to flow into the medical device reservoir; air may be removed from the line during fluid transfer. The system may be primed to expel air before the medical device is placed on the baseplate; dead volume in the baseplate may be minimized by duct size/volume.

Figure 5:
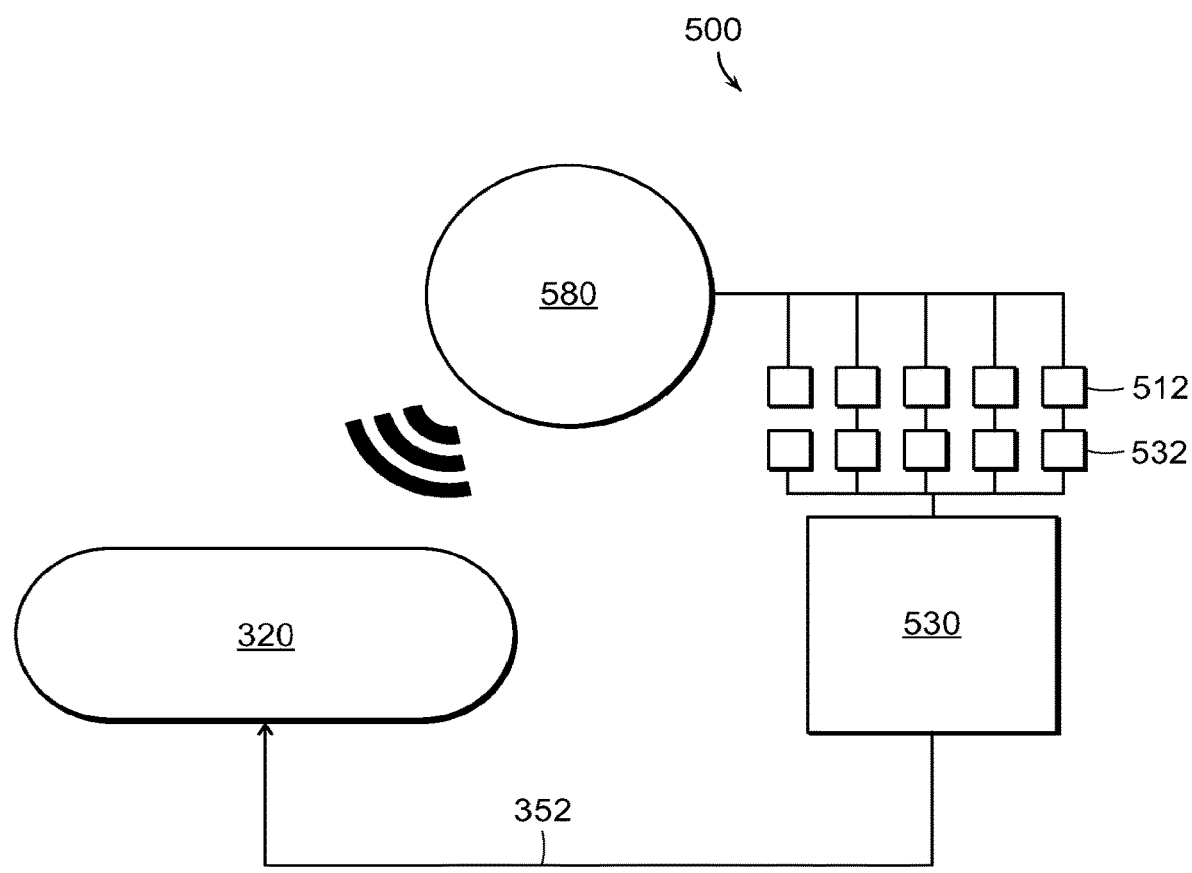
FIG. 5 shows an electrical keying arrangement for mating a drug container or vial to a baseplate.

In some embodiments, such as in the system 500 as shown in FIG. 5, the liquid drug container 530 includes keying features or structures in the form of one or more electrical contacts 532 that mate with corresponding keying features or structures in the form of one or more electrical contacts 512 on the baseplate, instead of, or in addition to, the physical keying features or structures described above. Circuitry in the baseplate connected to the baseplate contacts 512 detects the electrical characteristics of circuitry for the liquid drug container 530 connected to the container contacts 532. If the circuitry in the baseplate detects that the electrical characteristics match expected values, a transmitter 580 in the baseplate sends a signal to a receiver circuit in the medical device 320; upon receipt of the signal, the medical device 320 is configured to enable transfer of medication thereto. In other words, if the correct drug container is mated to the baseplate, the transmitter 580 sends a signal to allow drug transfer to the medical device 320, such as by the medical device 320 moving from a low energy state into a state that permits drug transfer thereto. The signal may be a wireless signal, such as a radio frequency (RF) signal sent by an RF transmitter or a Bluetooth low energy (BLE) signal sent by a BLE transmitter.

The circuitry in the baseplate and liquid drug container may be any combination of resistors, capacitors, inductors, semiconductors, or any other such component. In various embodiments, the liquid drug container circuitry includes a pattern of open circuits, short circuits, and/or resistive circuits that are connected to the liquid drug container contacts 532. The circuit in the baseplate may then, when the liquid drug container is mated to the baseplate, check to see if the pattern matches an expected pattern by, for example, sending signals to the circuitry associated with the liquid drug container via one or more liquid drug container contacts 532 and examining the behavior of other container contacts 532. For example, if a five-kilo-ohm resistance is expected between two container contacts 532, the circuitry in the baseplate may send out a voltage to one contact (e.g., five volts) and expect a current of approximately one milliamp back over the second contact. Any suitable system or method for evaluating and verifying the container circuitry may be used.

Figure 6A:
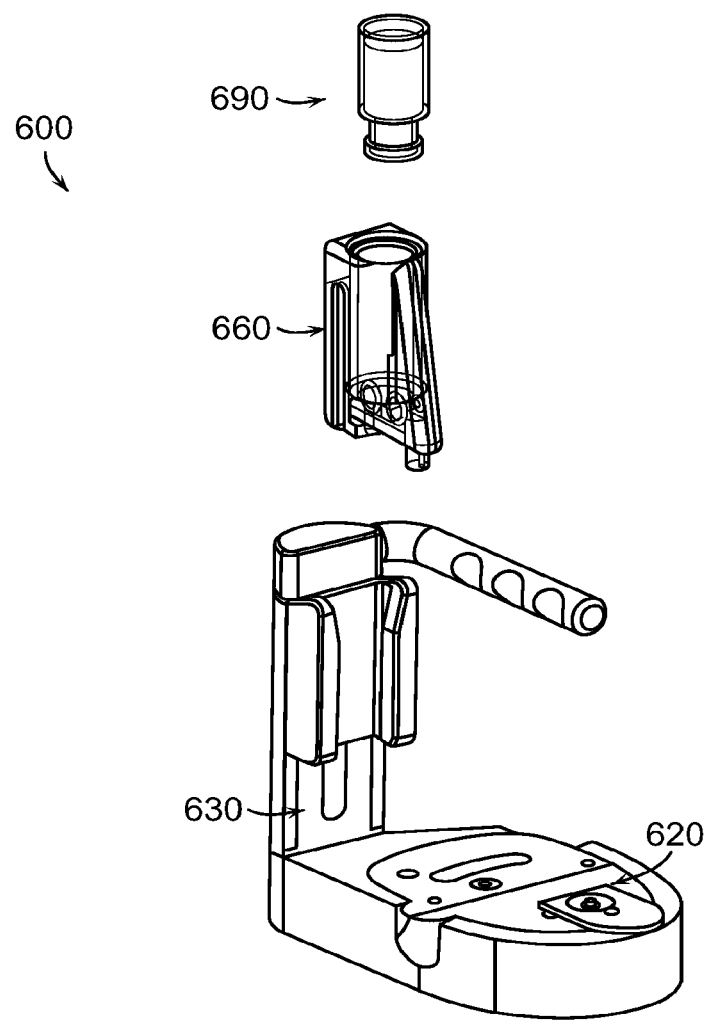
FIGS. 6A through 6U illustrate a system for assisting with filling of a medical device, the system comprising an arbor and cassette.
Figure 6C:
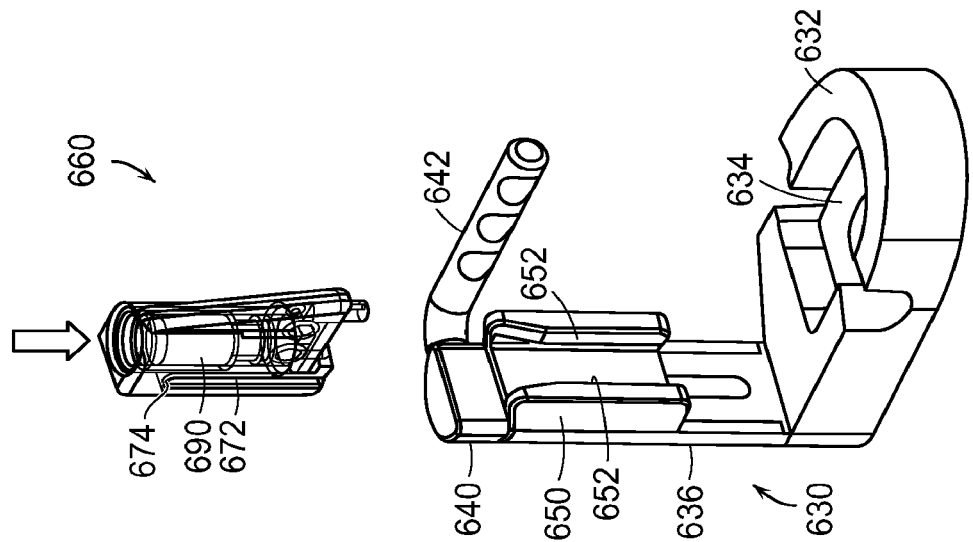
Figure 6B:
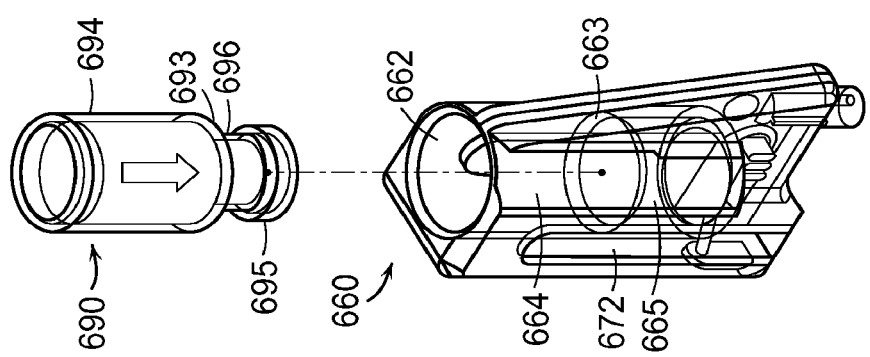
Figure 6E:
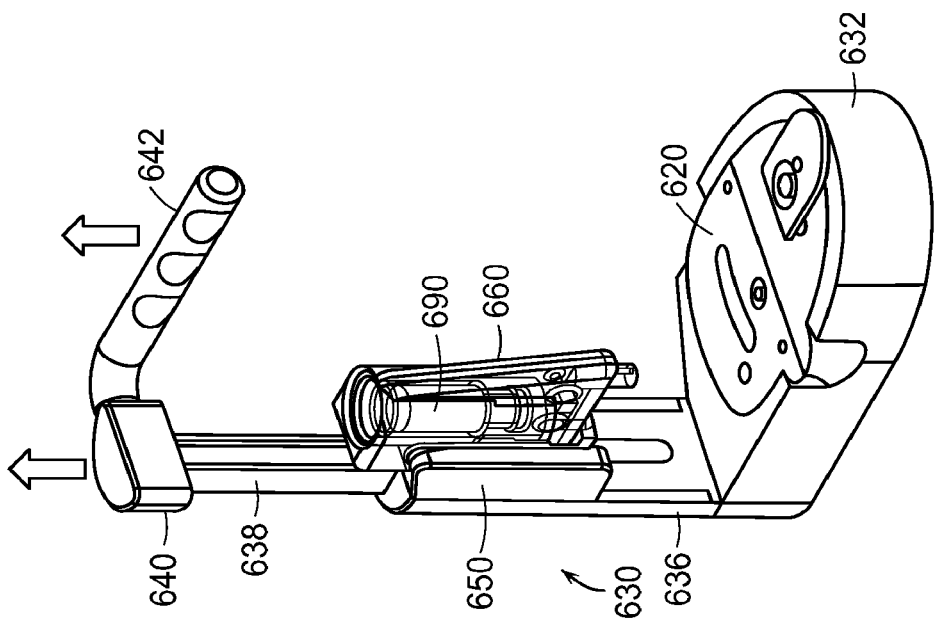
Figure 6D:
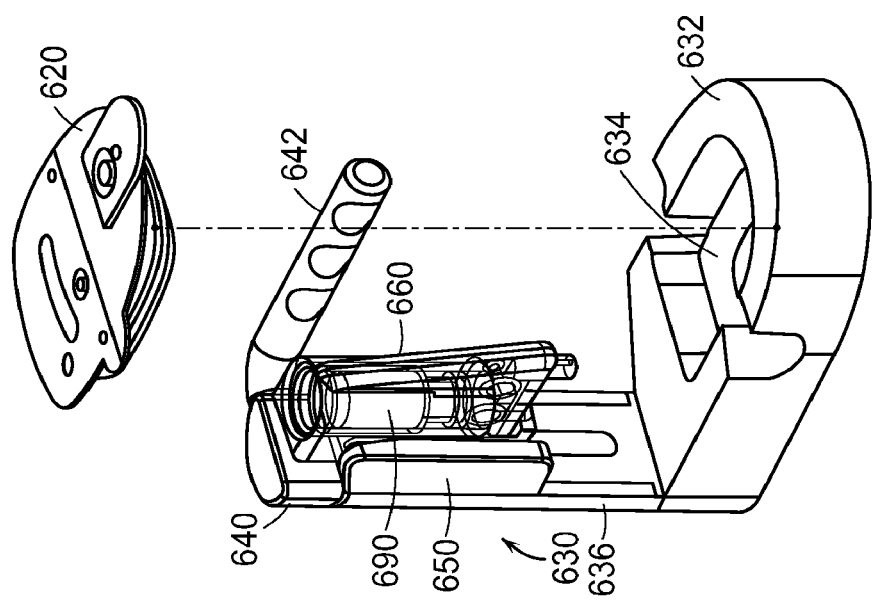
Figure 6H:
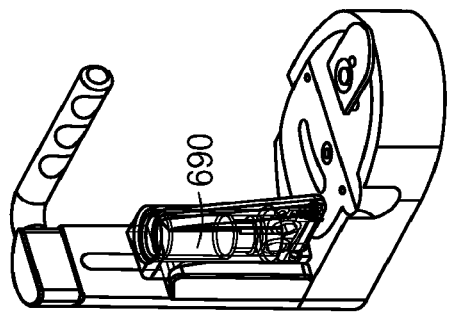
Figure 6G:
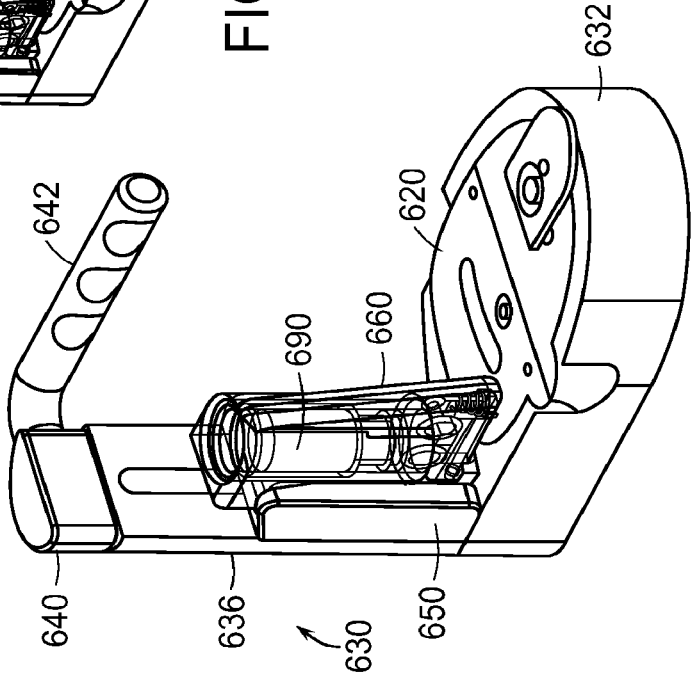
Figure 6F:
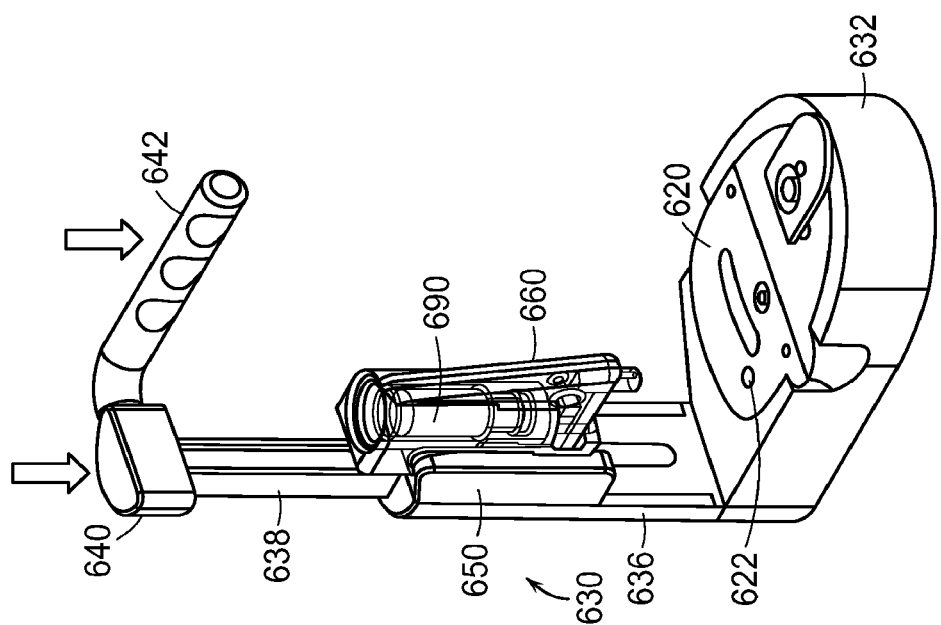
Figure 6K:
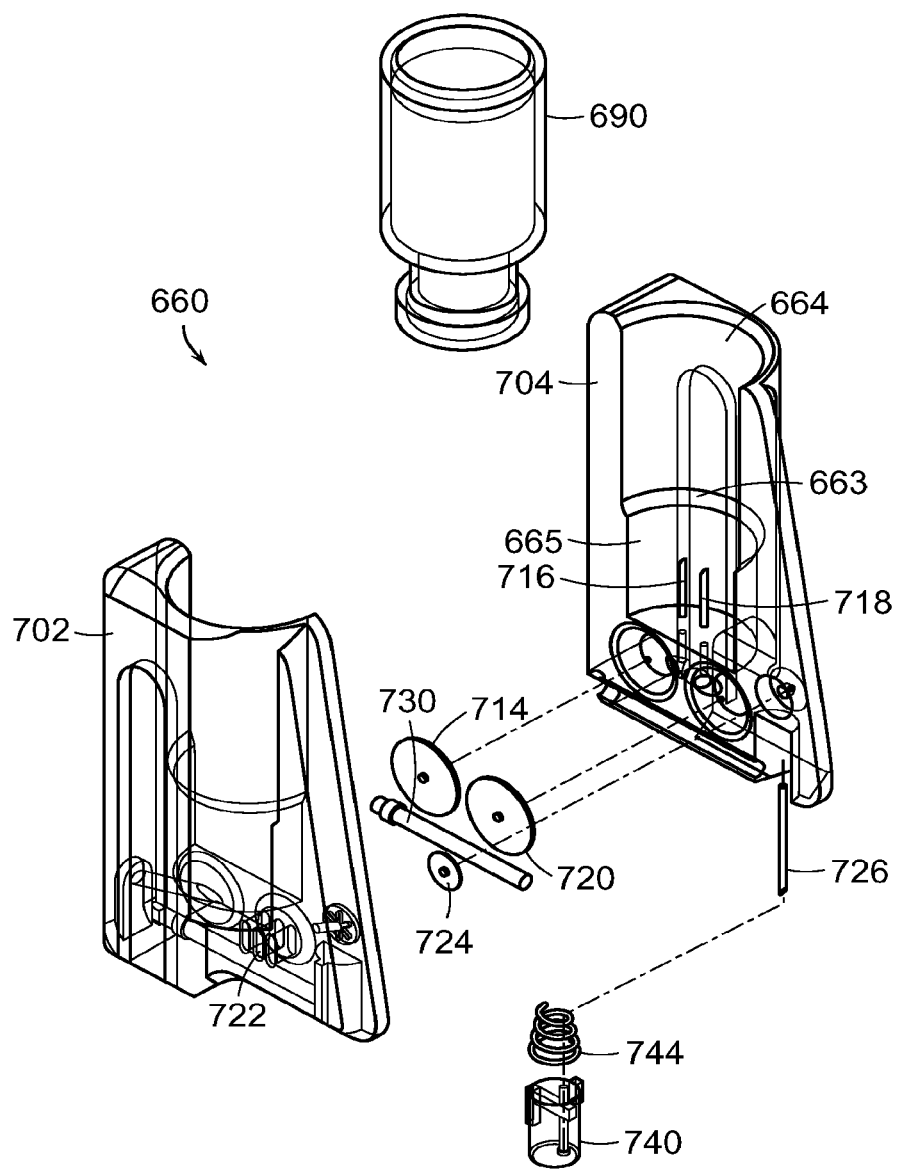
Figure 6T:
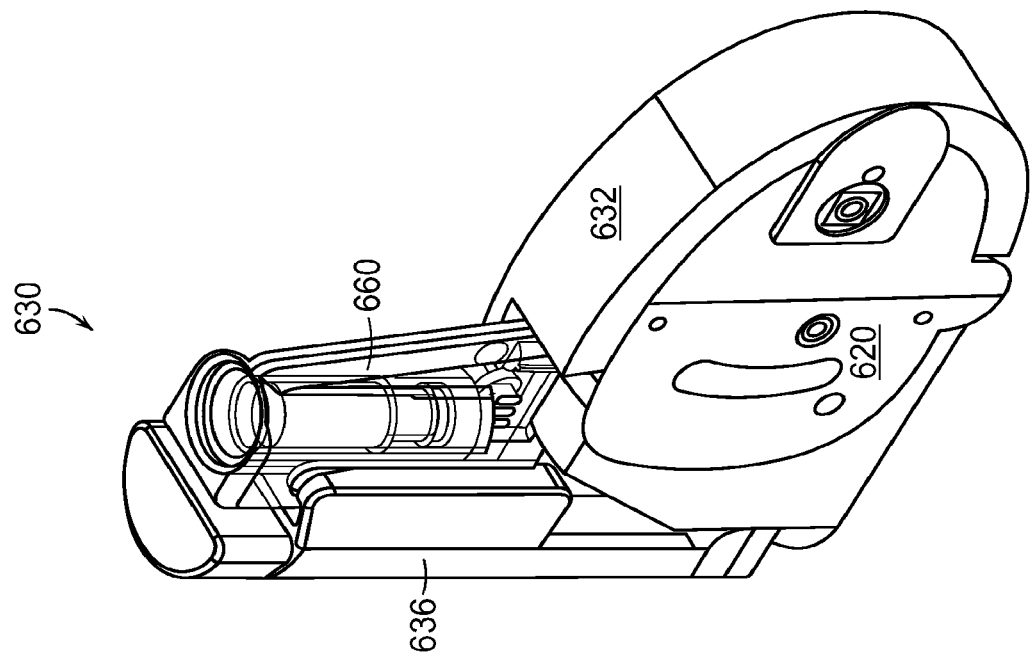
Figure 6S:
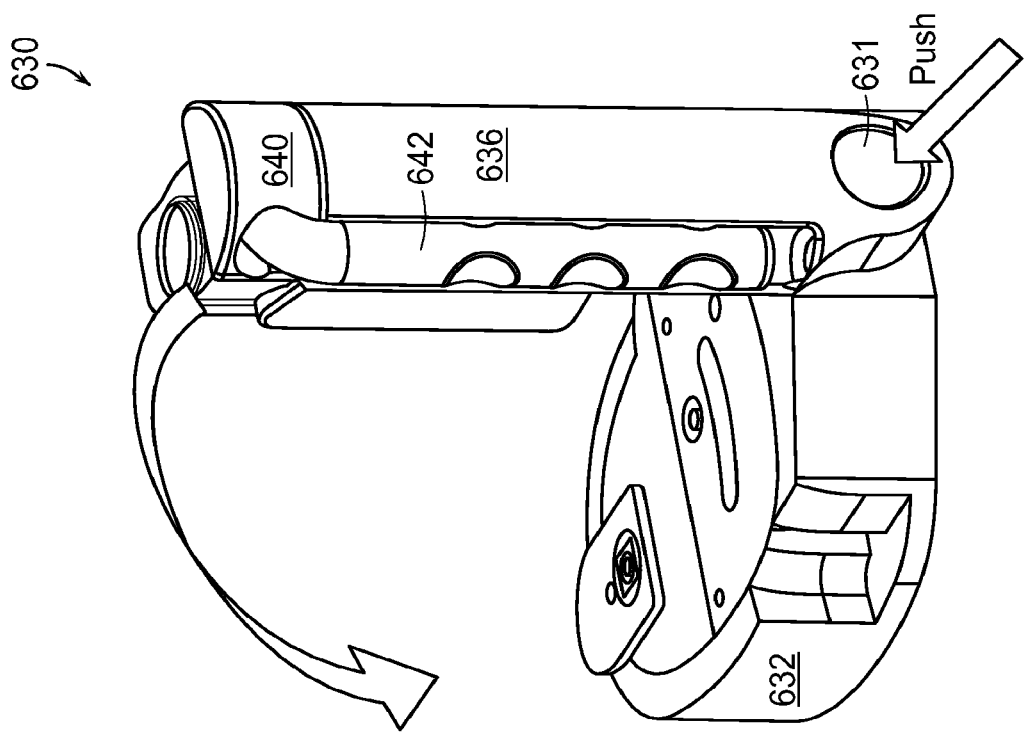
Figure 6U:
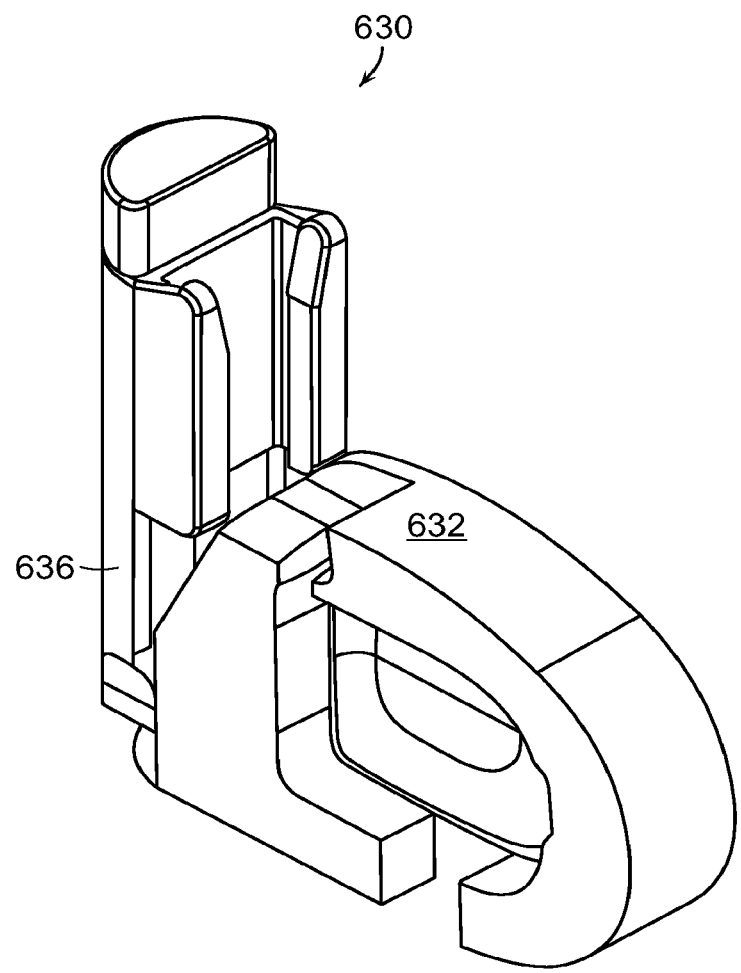

FIGS. 6A through 6U illustrate a system 600 for assisting with filling of a medical device 620, the system comprising an arbor 630 and a cassette 660. FIG. 6A shows a perspective view showing a liquid drug container 690, the cassette 660, the arbor 630, and the medical device 620. The medical device 620 may be a drug delivery device to be worn on or embedded in a body of a person to deliver medication to the person using a needle, cannula, etc., to dispense the medication from a reservoir in the medical device 620 into the body of the person using a pump, such as a mechanical or electric pump. An example medical device 620 is the medical device of the OmniPod® System (Insulet Corporation, Billerica, Mass.). The system 600 is used to transfer medicament from the liquid drug container 690 into a reservoir of the medical device 620. The liquid drug container 690 may be any suitable drug container as described above, such as a vial, cartridge, auto injector, pen, or syringe. In the illustrated example, the liquid drug container 690 is a vial, such as a standard glass vial with piercable membrane, for example a 0.5 ml vial.

FIG. 6B illustrates the step of loading the liquid drug container 690 into the cassette 660. The liquid drug container 690 is shown inverted in FIG. 6B. The liquid drug container 660 comprises a main body portion 694, a top lip 695, and a neck portion 696. The top lip 695 has a narrower diameter than the main body portion 694. At the top of the main body portion 694 is a shoulder 693. The top lip 695 is covered by a pierceable membrane, and the liquid drug container 690 is filled with a liquid medicament. The cassette 660 comprises a bore 662 having a wider upper portion 664 and a narrower lower portion 665 with a ledge 663 therebetween. In the step of loading the liquid drug container 690 into the cassette 660, the inverted liquid drug container 690 is advanced into the bore 662 until the shoulder 693 of the liquid drug container 690 abuts the ledge 663 of the cassette 660, which stops the liquid drug container 690 from further downward advancement into the bore 662. The top lip 695 is small enough to fit past the ledge 663 and into the narrower lower portion 665, but the main body portion 694 has a diameter larger than the lower portion 665 such that the shoulder 663 abutting the ledge 663 prevents further advancement of the liquid drug container 690 into the bore 662 of the cassette 660.

FIG. 6C illustrates the step of loading the cassette 660, which holds the liquid drug container 690, into the arbor 630. The arbor 630 has a base 632 with a medical device nest 634 shaped to hold the medical device 620. The arbor 630 further comprises a vertical member 636 extending upwardly from the base 632. The arbor 630 has a telescoping member 638 that is slideable within the vertical member 636. When the telescoping member 638 is in its full downward position within the vertical member 636, as shown in FIG. 6C, a top portion 640 of the telescoping member 638 is positioned above the vertical member 636. A charge handle 642 is connected to the top portion 640 of the telescoping member 638 to allow the user to slide the telescoping member 638 upward and downward relative to and within the vertical member 636. The arbor 630 also includes a dovetail adapter 650 that slides along the vertical member 636. The dovetail adapter has two ridges 652 for mating with corresponding slots 672 in the cassette 660. The cassette 660 has two such slots 672, one on either side of the cassette 660. Each slot 672 is open on the lower end of the cassette and terminates in an end abutment 674 at the upper end of the slot 672. In the step of loading the cassette 660 into the arbor 630, the cassette 660 is aligned such that the lower ends of the slots 672 align with the ridges 652 of the dovetail adapter 650. Downward movement of the cassette 660 causes the ridges 652 to fit within the slots 672. The cassette 660 is advanced into the dovetail adapter 650 until end abutments 674 engage the ridges 652 such that further advancement of the cassette 660 into the dovetail adapter 650 is prevented.

FIG. 6D illustrates the step of loading the medical device 620 into the arbor 630. The medical device 620 is placed into the medical device nest 634 until it is positioned securely within the medical device nest 634. The step of loading the medical device into the arbor 630 may take place before or after the steps of loading the liquid drug container 690 into the cassette 660 and loading the cassette 660 into the arbor 630.

FIG. 6E shows the liquid drug container 690 loaded into the cassette 660, the cassette 660 loaded into the arbor 630, and the medical device 620 loaded into the arbor 630. FIG. 6E further illustrates the step of lifting the charge handle 642 upward. Lifting the charge handle 642 pulls the telescoping member 638 upward and out of the vertical member 636. An internal stop limits the range of motion of the telescoping member 638 such that it cannot be pulled fully out of the vertical member 636.

FIG. 6F illustrates the step of pushing the charge handle 642 downward. Pushing the charge handle 642 downward pushes the telescoping member 638 downward and back into the vertical member 636. The lifting of the telescoping member 638 out of the vertical member 636 (as shown in FIG. 6E) causes the dovetail adapter 650 to become engaged with the telescoping member 638 or set to be engaged with the telescoping member 638 upon the downward motion of the telescoping member 638. In this way, when the telescoping member 638 is pushed downward and back into the vertical member 636, the downward motion of the telescoping member 638 into the vertical member 636 also causes downward motion of the dovetail adapter 650, and consequently downward motion of the cassette 660 carrying the liquid drug container 690. As the telescoping member 638 is pushed downward and back into the vertical member 636, the dovetail adapter 650, which is engaged with the telescoping member 638, slides downwardly along the vertical member 636. The downward motion of the telescoping member 638 into the vertical member 636 also causes charging of an internal air cylinder within the vertical member 636 of the arbor 630.

FIG. 6G shows the telescoping member 638 in its down position. At the end of the downward motion of the telescoping member 638, an internal lock causes the telescoping member 638 to be held in the down position so that it does not come back up. In this down position, the dovetail adapter 650 is also in a down position such that a fill port needle 726 of the cassette 660 has entered a fill port 622 of the medical device 620. At this locked down position, fluid communication is open between the internal air cylinder and the liquid drug container 690, which automatically forces the medicament from the liquid drug container 690 through the needle and the fill port 622 and into the reservoir of the medical device 620. Thus, the end of the downward movement of the charge handle 642 and telescoping member 638 automatically initiates the step of transferring the medicament from the liquid drug container 690 through the needle and the fill port 622 and into the reservoir of the medical device 620. FIG. 6G illustrates the liquid drug container 690 in a full condition. The liquid drug container 690 is visible such that the user can watch the medicament being dispensed therefrom and can visually inspect the fluid movement to verify the transfer and to see when it is complete. FIG. 6H shows the end of the step of transferring the medicament from the liquid drug container 690 into the reservoir of the medical device 620, at which point it can be seen that the liquid drug container 690 is empty.

FIG. 6I illustrates the step of returning the dovetail adapter 650 to its upward starting position. The dovetail adapter 650 can be released from the locked down position by a disengagement mechanism, such as a button or slide release on the vertical member 636 or by pulling the charge handle 642 outward as shown. Once the dovetail adapter 650 is released from the locked down position, a spring may return the dovetail adapter 650 to its upward starting position, which motion may be damped by a damper. Alternatively, the user may slide the dovetail adapter 650 upward along the vertical member 636, which can be accomplished by a slide member on the vertical member 636 or by grasping the dovetail adapter 650. FIG. 6I shows the dovetail adapter 650 in its upward starting position.

FIG. 6J illustrates the steps of removing the medical device 620 from the arbor 630 and removing the cassette 660 from the dovetail adapter 650 of the arbor 630. The user removes the medical device 620 from the arbor 630 by lifting it out of the medical device nest 634. This can be facilitated by the wall 635 of the medical device nest 634 having one or more notches 637, 639, allowing the user to more easily grasp a tab 627 or ledge 629 of the medical device 620. The user removes the cassette 660 from the dovetail adapter 650 by lifting it from the dovetail adapter 650, sliding it until the slots 672 disengage from the ridges 652.

FIG. 6K illustrates an exploded view of the cassette 660. In this example, the cassette 660 is made as two molded clamshell halves 702, 704. The clamshell halves 702, 704 may be joined together in any suitable manner, such as snap-fit, adhesive, or other suitable bonding.

FIG. 6L shows an assembled view of the cassette 660. FIG. 6M shows a perspective view of the cassette 660 in which the front and one side of the cassette 660 is visible. FIG. 6N shows a perspective view of the cassette 660 in which the back and the other side of the cassette 660 is visible.

FIGS. 6K through 6N show the flow routes for air into the liquid drug container 690 and for medicament out of the liquid drug container 690. As can be seen, when the liquid drug container 690 is loaded into the cassette 660, two piercing needles 716, 718 pierce the membrane on top of the liquid drug container 690 to create passages to the internal space within the liquid drug container 690.

When the loaded dovetail adapter 650 is moved to its downward position for initiation of drug transfer, air enters the cassette 660 through air inlet 710 in the back of the cassette 660. The air comes from the internal air cylinder within the vertical member 636 of the arbor 630. When the telescoping member 638 is forced to the locked down position, fluid communication is opened from the internal air cylinder to the air inlet 710. The air flows through air passage 712 and air particulate filter 714, which filters particulates from the air before the air enters the liquid drug container 690. From there, the air passes through air intake needle 716 into the liquid drug container 690. The air forces medicament from the liquid drug container 690 out of the medicament outlet needle 718. An air eliminating filter 720 allows air but not medicament to escape through an air elimination vent 722. The medicament flows through a passive check valve 724 that prevents backflow. From there, the medicament passes through a fill port needle 726 which has entered the fill port 622 of the medical device 620, allowing the medicament to flow into the reservoir of the medical device 620.

The cassette 660 includes a mechanism for shielding the fill port needle 726. This both prevents injury to the user as well as damage to the fill port needle 726. The cassette 660 includes a retractable needle cap 740 that is biased by a spring 744 to an extended position in which it covers the distal end of the fill port needle 726, as shown in FIG. 6L. A flexible release tab 742 in its relaxed condition extends outwardly to engage a portion of the housing of the cassette 660 to prevent the retractable needle cap 740 from being pressed back from its extended position. Thus, when the user handles the cassette 660, the fill port needle 726 is covered by the retractable needle cap 740.

The cassette 660 further comprises a needle cap release rod 730 comprising a first end 732 and a second end 734. The needle cap release rod 730 is biased toward the back of the cassette 660 by the flexible release tab 742 or alternatively by a separate spring or other biasing mechanism such that the first end 732 extends out of the housing of the cassette 660 (in this example, by virtue of a small cutout or notch in the housing). When the telescoping member 638 is forced toward the locked down position, the first end 732 of the needle cap release rod 730 engages a cam follower on the arbor 630. As shown in FIGS. 6O and 6P, this action presses the needle cap release rod 730 further into the housing of the cassette 660, and the second end 734 of the needle cap release rod 730 presses against the flexible release tab 742. This presses the flexible release tab 742 inwardly so that it no longer engages the housing of the cassette 660, thereby releasing the needle cap 740 to be pressed back from its extended position. As the cassette 660 is advanced toward the medical device 620, the needle cap 740 engages the medical device 620, and the downward movement of the cassette 660 forces the needle cap 740 into the recess 746 in the cassette 660, compressing the spring 744. At the same time, as the cassette 660 is advanced toward the medical device 620, the fill port needle 726 enters the fill port 622 of the medical device 620. During this time, the fill port needle 726 is protected because the distal end of the needle cap 740 is engaged with the medical device 620.

After the medicament has been transferred to the medical device 620, as the cassette 660 is lifted way from the medical device 620, the movement of the needle cap 740 occurs in reverse. The spring 744 forces the needle cap 740 to extend back to its extended position, covering the fill port needle 726. As the cassette 660 is further lifted, the needle cap release rod 730 disengages from the cam follower on the arbor 630, allowing the flexible release tab 742 to move back into its relaxed condition in which it extends outwardly to engage a portion of the housing of the cassette 660 to prevent the retractable needle cap 740 from being pressed back from its extended position. The needle cap 740 remains locked in this extended position as the user removes the cassette 660 from the arbor 630.

FIGS. 6Q through 6U illustrate steps in collapsing the arbor 630 into a compact profile for storage. The charge handle 642 has a main portion 644, an extension portion 646, and an elbow portion 648. In FIG. 6Q, the user swings the charge handle 642 downward so that its main portion 644 is parallel to the vertical member 636. The arbor 630 may have a release lock that holds the charge handle 642 in its operating position (as shown, for example, in FIG. 6A). The release lock may be disengaged such as by pushing a lock-release button to allow the user to swing the charge handle 642 downward so that its main portion 644 is parallel to the vertical member 636.

In FIG. 6R, after the user has moved the charge handle 642 so that the main portion 644 is parallel to the vertical member 636, the user pushes the charge handle 642 toward the vertical member 636. This pushing moves the extension portion 646 inside of the top portion 640 of telescoping member 638. This pushing motion also moves the main portion 644 into a recess 641 in the side of the vertical member 636.

In FIG. 6S, the user releases a lock between the vertical member 636 and the base 632 and swings the vertical member 636 to be aligned with the base 632. The lock, which holds the vertical member 636 in its operating position with respect to the base 632 (as shown, for example, in FIG. 6A) may be released by pushing a button 631.

FIGS. 6T and 6U show the arbor 630 after the vertical member 636 has been moved to be aligned with and parallel to the base 632. In FIG. 6T, the cassette 660 and medical device 620 are shown loaded in the arbor 630. In FIG. 6U, the arbor 630 is without the cassette 660 and medical device 620. In both cases, the device has a low and compact profile for easy storage.

Figure 7D:
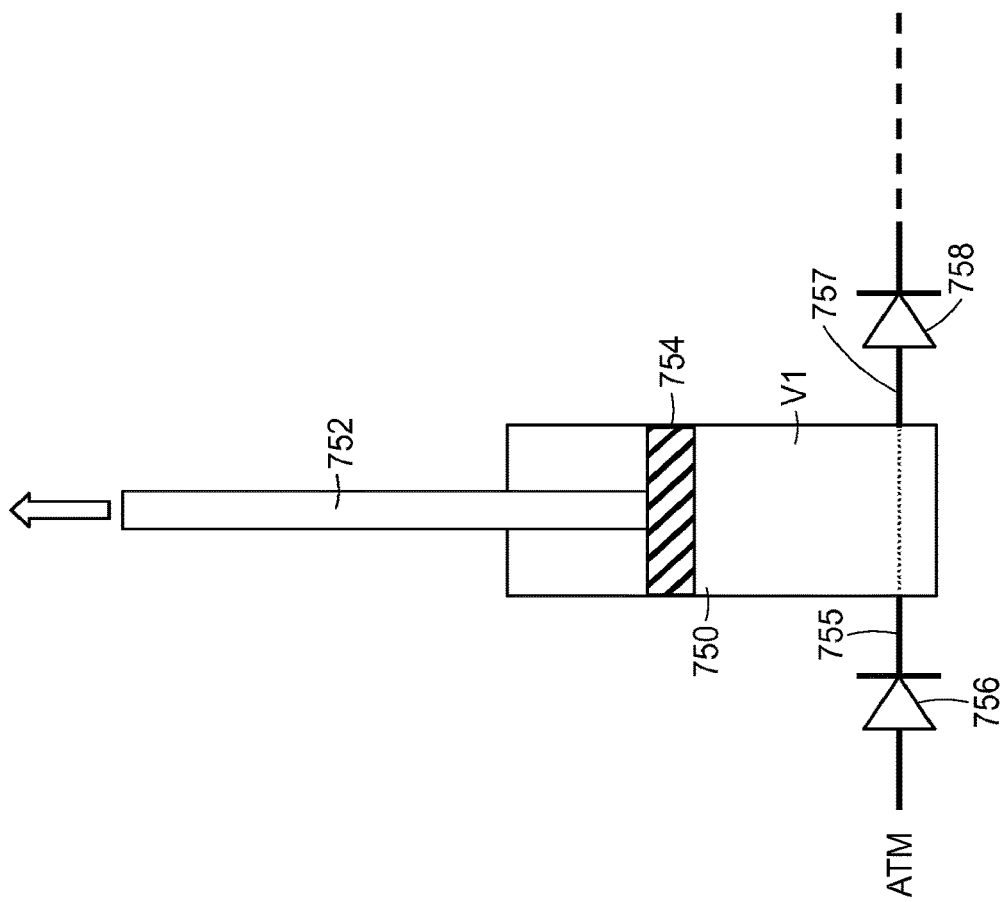

FIGS. 7A through 7L illustrate schematically the operation of the system 600. FIGS. 7A and 7B show illustrations corresponding to the condition shown in FIG. 6D. The charge handle 642 is shown in its down position, while the dovetail adapter 650 is shown in its up position.

As shown in FIGS. 7A and 7B, the vertical member 636 has an internal air cylinder 750 within it. A plunger rod 752 is connected to the charge handle 642 and extends into the air cylinder 750. A plunger or piston 754 is located at the end of the plunger rod 752 to seal a volume of the air cylinder 750.

An inlet air path 755 connects the atmosphere to the sealed volume of the air cylinder 750. A one-way check valve 756 allows flow from the atmosphere through the inlet air path 755 into but not out of the sealed volume of the air cylinder 750. An outlet air path 757 extends out of the sealed volume of the air cylinder 750. A one-way valve 758 when opened allows flow through the outlet air path 757 out of the air cylinder 750 but prevents flow back into the air cylinder 750.

The dovetail adapter 650 is connected to a spring 782 which biases the dovetail adapter 650 to its up position. The charge handle 642 is connected to a dovetail engagement rod 770 which has a latch 772 connected to it. The dovetail adapter 650 has a shelf 780 or other engagement mechanism for engaging with the latch 772.

Figure 7C:
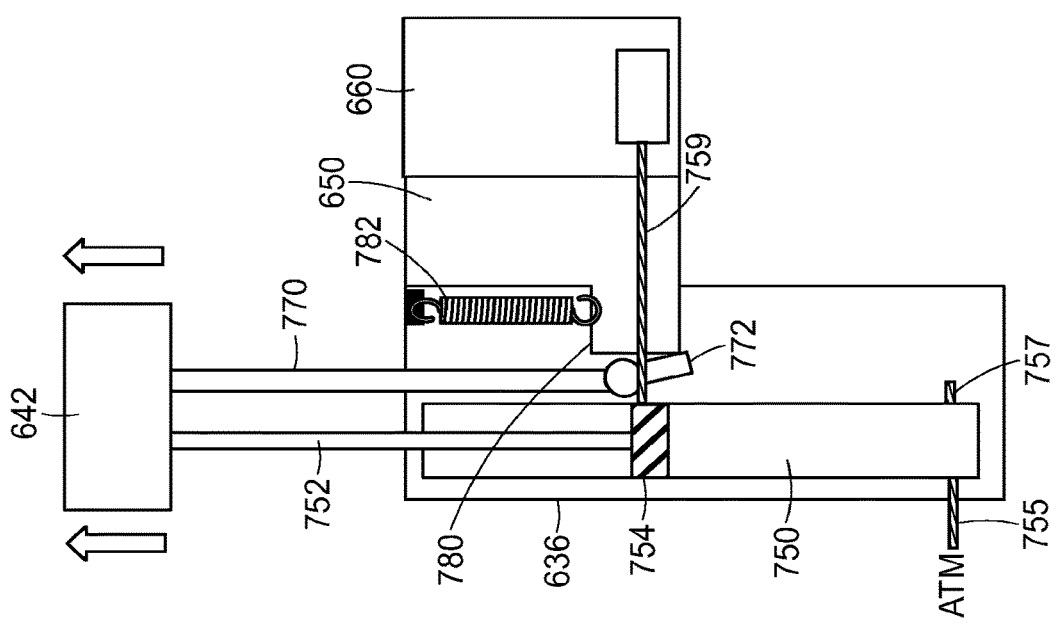

FIGS. 7C and 7D show illustrations corresponding to the charge handle 642 being pulled up part way. This pulls the plunger rod 752 and plunger or piston 754 up within the air cylinder 750. This draws air into the air cylinder 750 from the atmosphere through the inlet air path 755. It also pulls the dovetail engagement rod 770 and latch 772 up. The dovetail engagement rod 770 can have a ratcheting system associated with it so that it cannot be pushed back down until full extension is reached and the latch 772 engages the dovetail adapter 650 as described below.

Figure 7F:
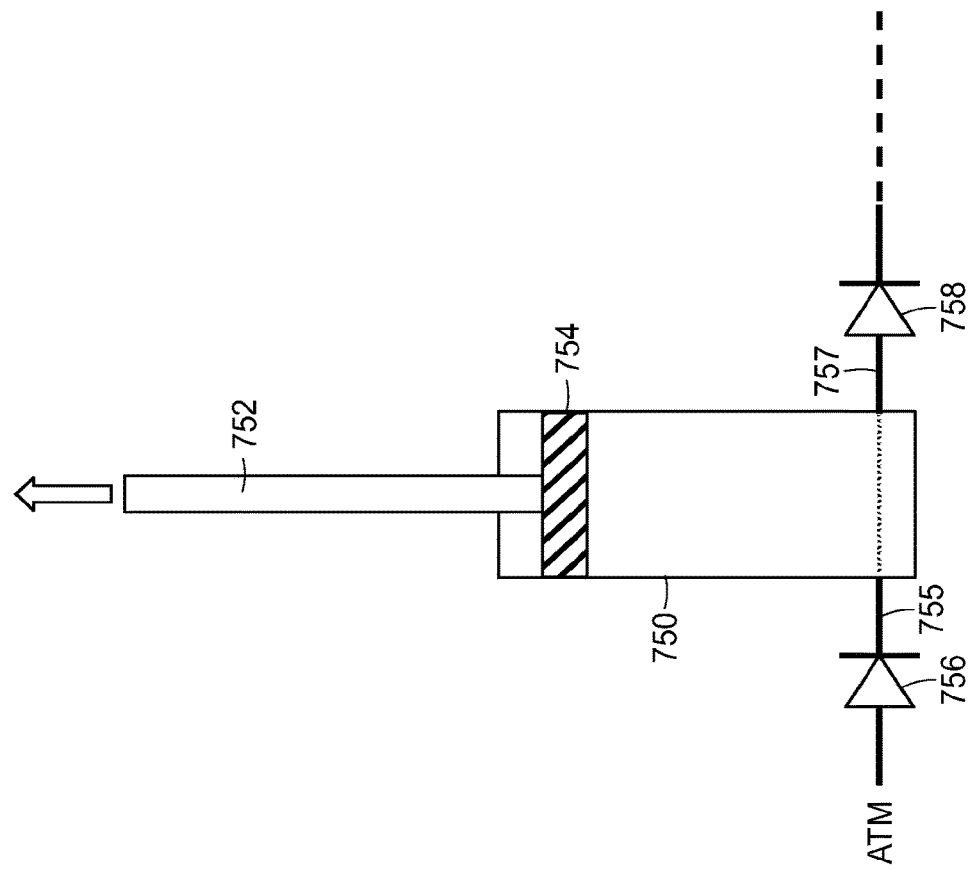
Figure 7E:
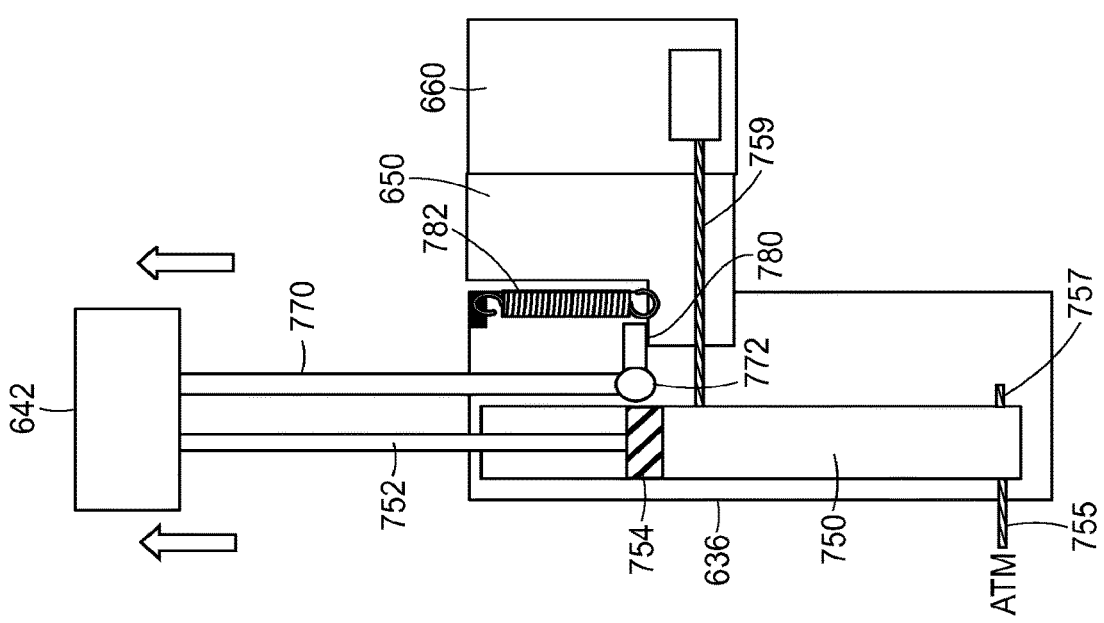

FIGS. 7E and 7F show illustrations corresponding to the charge handle 642 pulled to its full up position. This pulls the plunger rod 752 and plunger or piston 754 further up within the air cylinder 750, drawing more air into the air cylinder 750 from the atmosphere through the inlet air path 755. It also pulls the dovetail engagement rod 770 and latch 772 up so that the latch 772 engages or is set to engage with the dovetail adapter 650, for example by engaging with the ledge 780 or other engagement mechanism of the dovetail adapter 650. As one example, the latch 772 may be designed to travel past the shelf 780 and then, once past the shelf 780, to be rotated into an engagement position by a torsion spring.

Figure 7H:
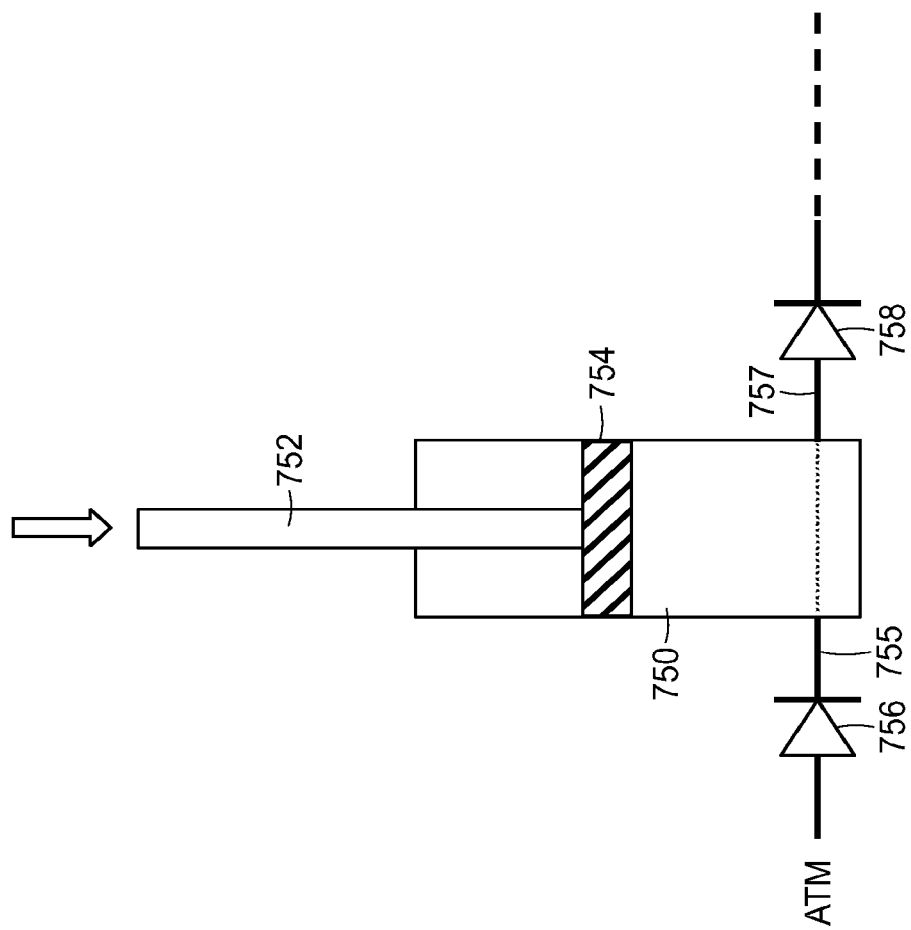
Figure 7G:
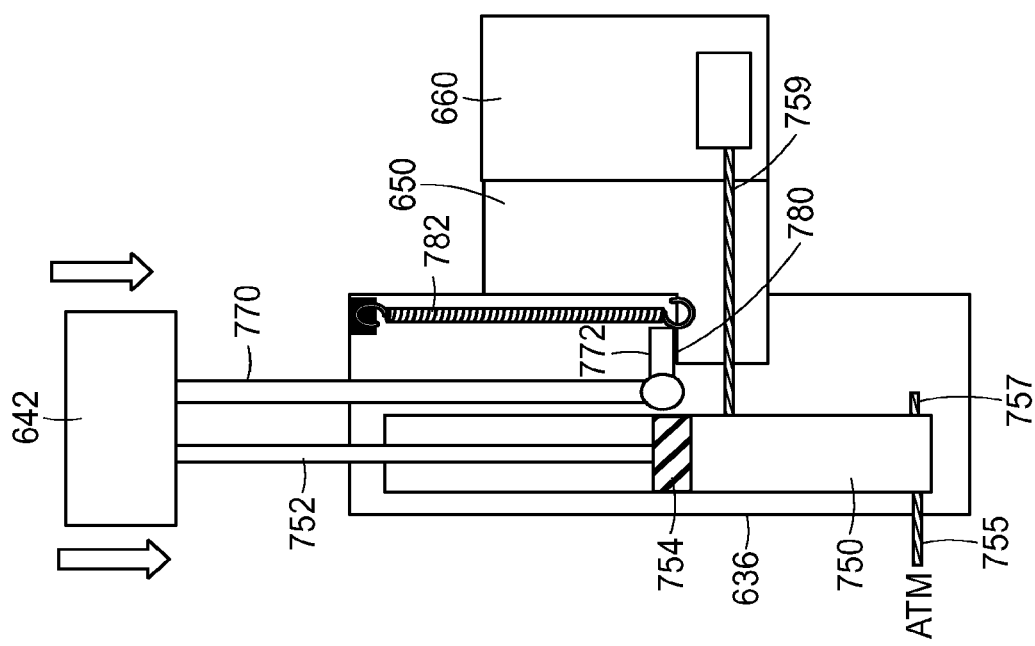

FIGS. 7G and 7H show illustrations corresponding to the charge handle 642 being pushed down part way. This pushes the plunger rod 752 and plunger or piston 754 down within the air cylinder 750, compressing the air in the air cylinder 750. The valve 758 (or another valve) prevents flow out of the air cylinder 750 at this time. Due to the engagement of the latch 772 with the dovetail adapter 650, for example by being engaged with the ledge 780 or other engagement mechanism of the dovetail adapter 650, the downward movement of the charge handle 642 also causes downward movement of the dovetail adapter 650 (and the cassette 660 and liquid drug container 690 held by it).

Figure 7J:
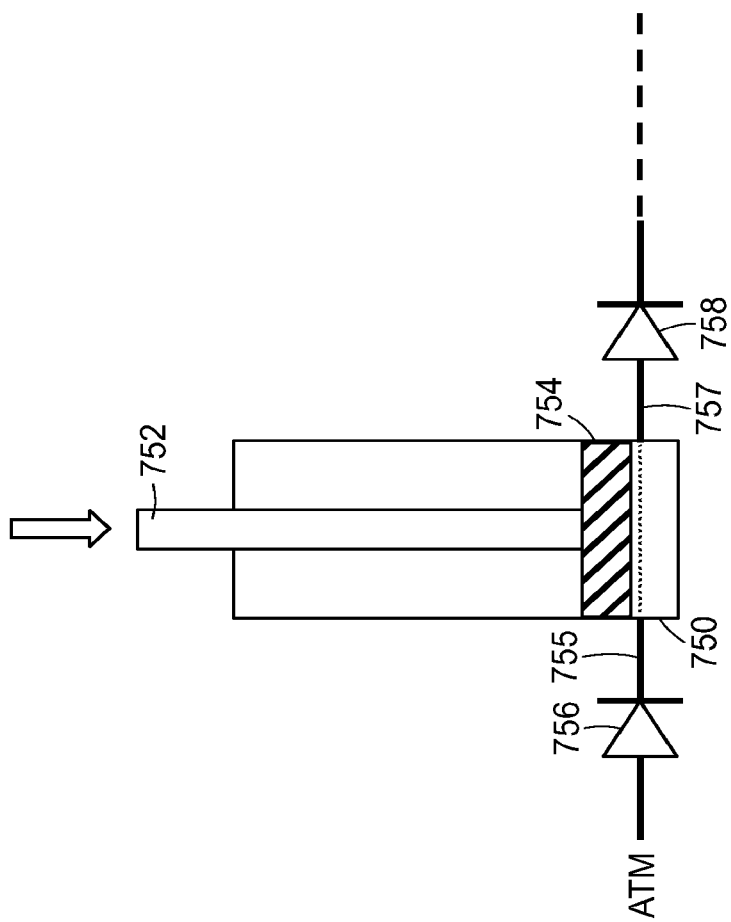
Figure 7I:
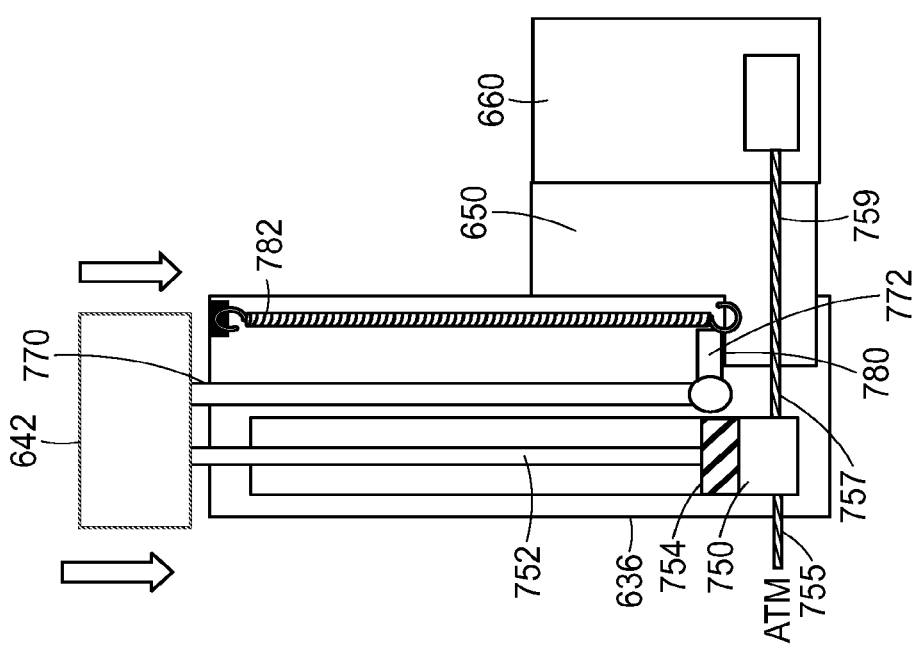

FIGS. 7I and 7J show illustrations corresponding to the charge handle 642 being pushed down to its full down position. This further pushes the plunger rod 752 and plunger or piston 754 down within the air cylinder 750, compressing the air in the air cylinder 750. At the end of the down stroke, the valve 758 (or another valve) is opened, allowing flow out of the air cylinder 750 at this time. The downward movement of the charge handle 642 also causes downward movement of the dovetail adapter 650 (and the cassette 660 and liquid drug container 690 held by it) to its full down position, so that the air path 759 to the cassette 660 (which corresponds to or is connected to air passage 712) is connected to outlet air path 757. Thus, the air flowing out of the air cylinder 750 through the outlet air path 757 flows into the liquid drug container 690 as described above. The volume of the air cylinder 750 and air compression is calibrated (according to the ideal gas law) to provide the correct amount of air pressure for transfer of the drug from the liquid drug container 690. Only moderate force by the user is required for air compression.

Figure 7K:
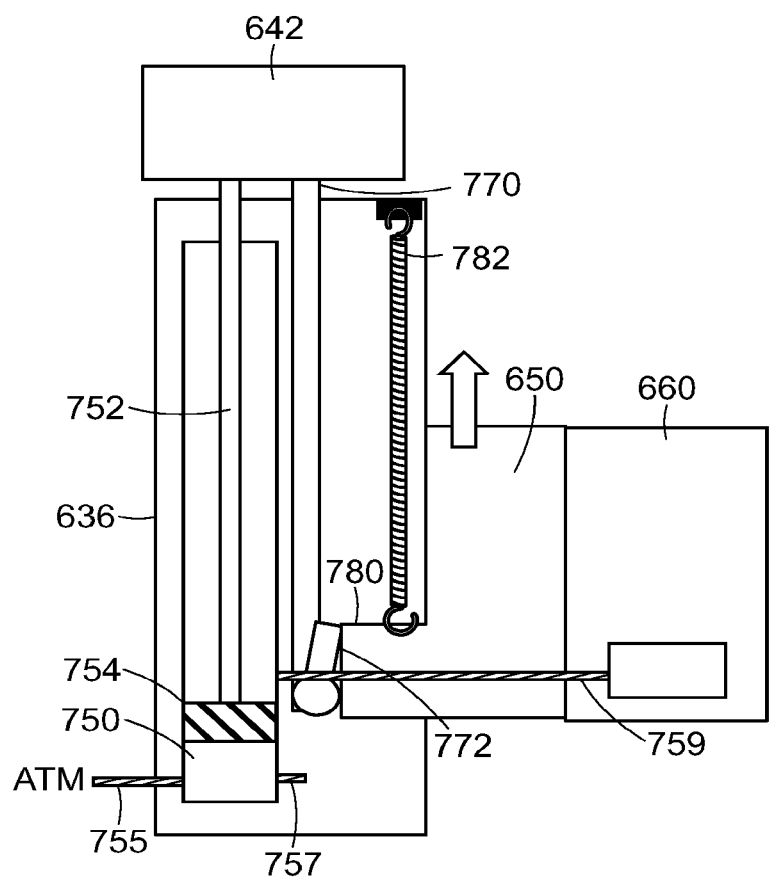
Figure 7L:
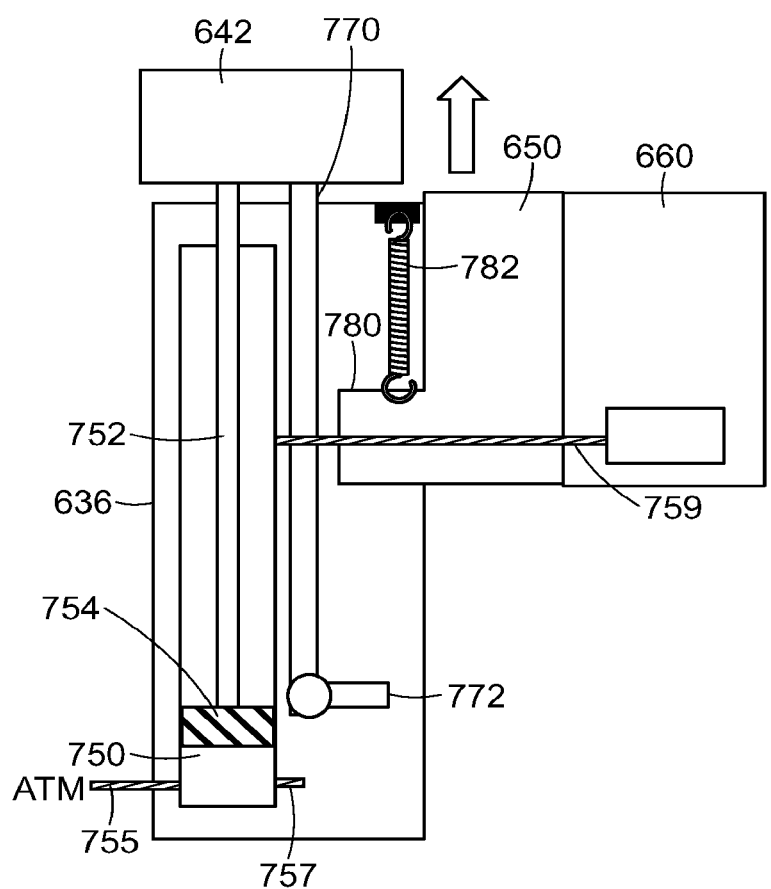

As described above with respect to FIG. 6I, the dovetail adapter 650 can be released from the locked down position by a disengagement mechanism, such as a button or slide release on the vertical member 636 or by pulling the charge handle 642 outward as shown. This can release the latch 772 from engagement with the ledge 780 or other engagement mechanism of the dovetail adapter 650, as shown in FIG. 7K. Once the dovetail adapter 650 is released from the locked down position, the spring 782 may return the dovetail adapter 650 to its upward starting position, which motion may be damped by a damper.

A system such as the system 600 can have a number of advantages. It can be easy to use, can assist patients with transferring the drug from the liquid drug container to the medical device, can require only gross motor skills, is safe to use (e.g., by covering the needle), has a small footprint, is collapsible, is relatively easy and inexpensive to manufacture, and is eco-friendly. For example, the cassette can be recyclable or disposable. In addition, the cassette 660 may be provided with keying features or structures as described herein, for use only with liquid drug containers having matching keying features or structures. The medical device nest 634 can be designed with keying features or structures as described herein, for use only with medical devices having matching keying features or structures. In this way, the system insures that only the correct drug is used to fill the medical device.

Figure 8:
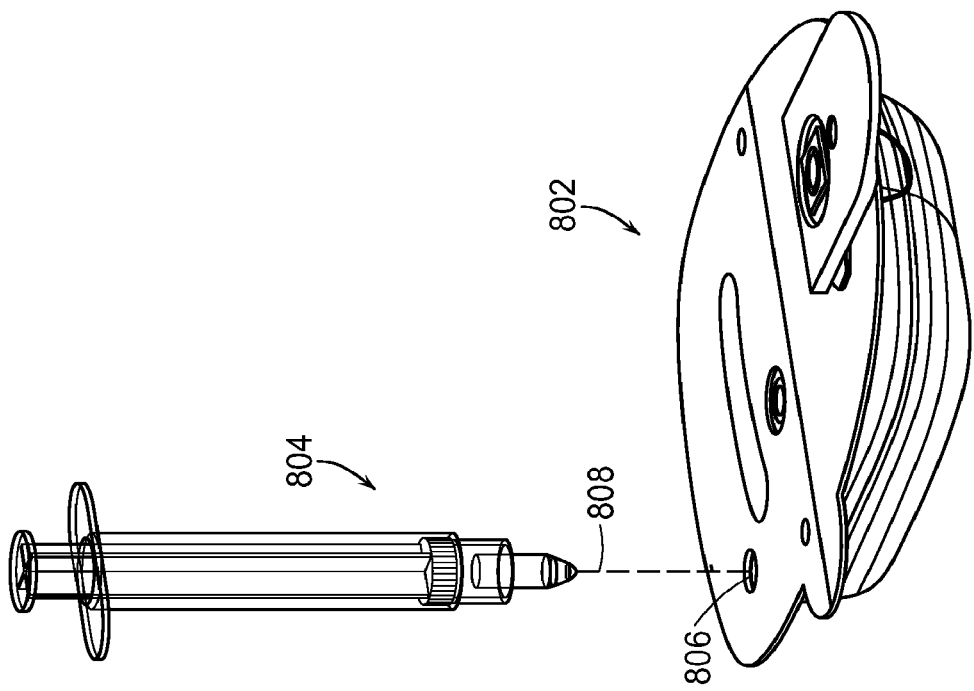
FIG. 8 illustrates a conventional process for filling a drug delivery device with a drug.

FIG. 8 illustrates a conventional process for filling a drug delivery device with a drug. As shown in FIG. 8, a medical device or drug delivery device 802 can be accessed by a syringe 804. The drug delivery device 802 can be a wearable drug delivery device. The drug delivery device 802 can be designed to deliver any type of drug or medicine to a user such as, for example, insulin. The drug delivery device 802 can be a single-use device (e.g., filled once and used once and then discarded) or can be a multiple-use device (e.g., filled one or more times and used after one or more fillings). The syringe 804 can contain the drug or medicine intended to be delivered by the drug delivery device 802 that is to be transferred to the drug delivery device 802 before use. In various embodiments, the drug delivery device 802 can be an OmniPod® (Insulet Corporation, Billerica, Mass.) insulin delivery device.

As shown in FIG. 8, the drug delivery device 802 can include a fill port 806 that can be accessed by the needle tip 808 of the syringe 804. As shown by the conventional filling process, the syringe 804 is manipulated without any alignment aid when attempting to position the needle tip 808 of the syringe 804 into the fill port 806. For individuals with compromised motor skills such as, for example, an elderly user of the drug delivery device 802, precisely aligning the needle tip 808 of the syringe 804 with the fill port 806 of the drug delivery device 802 can be a cumbersome and challenging task. If the needle tip 808 of the syringe 804 is not precisely aligned with the fill port 806 of the drug delivery device 802, one or more problems can occur such as, for example, damage to the needle tip 808 of the syringe 804 and/or improper delivery of the drug from the syringe 804 to the drug delivery device 802.

For example, the drug delivery device 802 may include a septum within the fill port 806 that is to be pierced by the needle tip 808 of the syringe 804 before the drug within the syringe 804 can be properly transferred into the drug delivery device 802. If the needle tip 808 of the syringe 804 is not aligned properly with the septum of the fill port 806 of the drug delivery device 802, then the septum may not be pierced and/or the needle tip 808 of the syringe 804 may be damaged. In turn, the drug within the syringe 804 may not be properly transferred to the drug delivery device 802. This can result in spillage or other waste or loss of the drug and/or an inability to provide the proper dosage of a medicine or drug to the user.

Figure 9A:
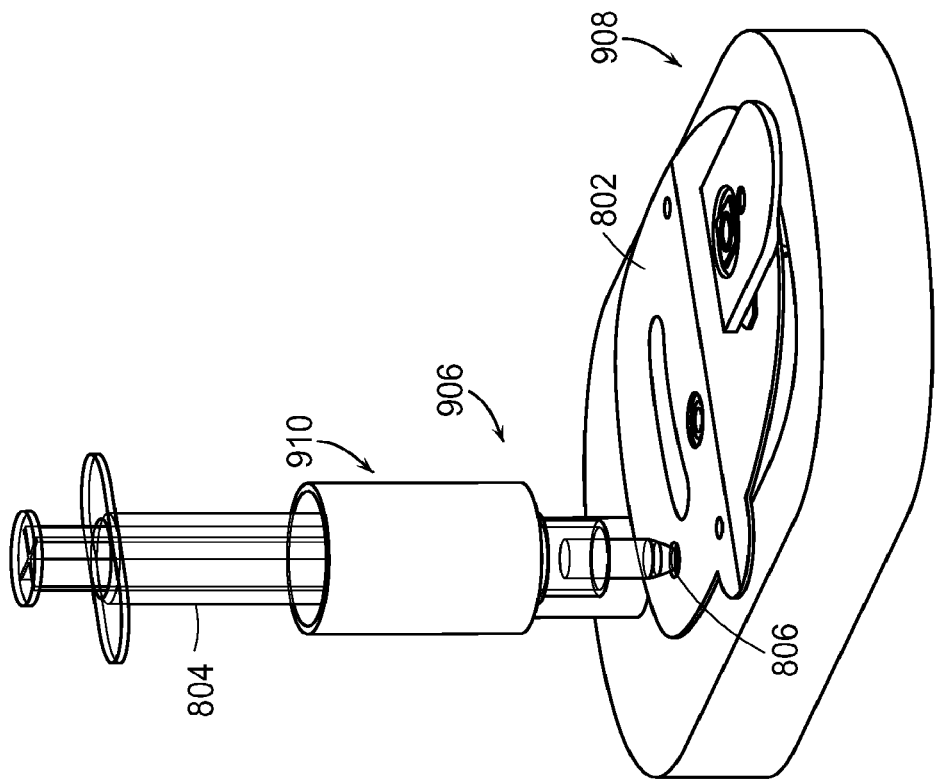
FIG. 9A shows an alignment aid or device that can be used to ensure proper alignment of a liquid drug container and a drug delivery device.

As shown in FIG. 9A, an alignment aid or device 906 can be used to ensure proper alignment of a liquid drug container, such as a syringe, vial, or cartridge, and a drug delivery device. FIG. 9A shows the alignment aid 906 used to align the syringe 804 and the drug delivery device 802. In particular, the alignment aid 906 can ensure that the needle tip 808 of the syringe 804 is properly aligned with the fill port 806 of the drug delivery device 802 to ensure that the drug contained in the syringe 804 is properly and efficiently transferred to the drug delivery device 802. In this way, for example, the septum of the fill port 806 of the drug delivery device 802 can be precisely pierced by the needle tip 808 of the syringe 804 to ensure that a reservoir within the drug delivery device 802 receives the intended drug dosage.

The alignment aid or device 906 can include a base 908 (or baseplate) and a stem or extension 910 (or arm). The base 908 of the alignment device 906 can hold or contain the drug delivery device 802. In various embodiments, the base 908 can be shaped to accept or hold the drug delivery device 802 in a position so as to make the fill port 806 of the drug delivery device 802 accessible (e.g., positioned under the stem or extension 910). In general, when positioned in the base 908, the drug delivery device 802 can remain in a stable position.

The stem 910 can also be considered to be a syringe holder, vial holder, or cartridge holder. The stem 910 can be coupled to the base 908 and can include one or more features for holding or securing a liquid drug container device such as a vial, cartridge, or the syringe 804. The stem 910 can be positioned so as to position the needle tip 808 of the liquid drug container 804 directly over the fill port 806 of the drug delivery device 802. As shown in FIG. 9A, the syringe 804 is precisely aligned with the fill port 806 of the drug delivery device 802. As such, the drug delivery device 802 can be filled more easily and efficiently without waste or spillage.

The alignment device 906 can be used by a wide range of users including those with compromised motor skills. The alignment device 906 can be manufactured to be low cost and can be re-used (e.g., to fill the same or a different drug delivery device 802). Further, the alignment device 906 can be designed to be collapsible so as to have a small footprint, thereby reducing packaging space and costs.

FIGS. 9B through 9D illustrate a fluid transfer process using the alignment device 906. As shown in the FIG. 9B, the syringe 804 can include a syringe needle tip 808 and a syringe plunger 810 that can force a liquid or fluid out of the syringe reservoir through the syringe needle tip 808. In a first step of the fluid transfer process, the syringe 804 with the syringe plunger 810 in an extended position can be positioned into the alignment device 906. Specifically, the syringe 804 can be positioned in the arm or stem 910 of the alignment device 906. In doing so, the needle tip 808 of the syringe 804 can be positioned directly over the fill port 806 of the drug delivery device 802.

Prior to or after placing the syringe 804 in the arm or stem 910 of the alignment device 906, the drug delivery device 802 can be positioned in the base 908 of the alignment device 906. As shown in FIG. 9B, the drug delivery device 802 can be positioned into an open area or medical device nest of the base 908 such that the drug delivery device 802 can rest within the base 908 (as opposed to on top of the base 908). By positioning the drug delivery device 802 into an open area or medical device nest of the base 908, the drug delivery device 802 can be stabilized for the fluid transfer process.

Once the needle tip 808 of the syringe 804 is positioned directly over the fill port 806 of the drug delivery device 802, a second step of the fluid transfer process can occur. Specifically, as shown in FIG. 9C, the plunger 810 of the syringe 804 can be compressed to force a drug or medicine or other fluid within the syringe 804 out of the syringe 804 through the needle tip 808 and into the fill port 806 of the drug delivery device 802. When the desired amount of fluid is transferred from the syringe 804 to the drug delivery device 802 (e.g., a desired drug dosage), the fluid transfer process can be complete. FIG. 9D shows the plunger 810 pressed into the syringe barrel at the completion of drug transfer. At the completion of drug transfer, the syringe 804 can be removed from the arm or stem 910 of the alignment device 906. Additionally, the drug delivery device 802 can be removed from the base 908 of the alignment device 906 and can be used.

Figure 9E:
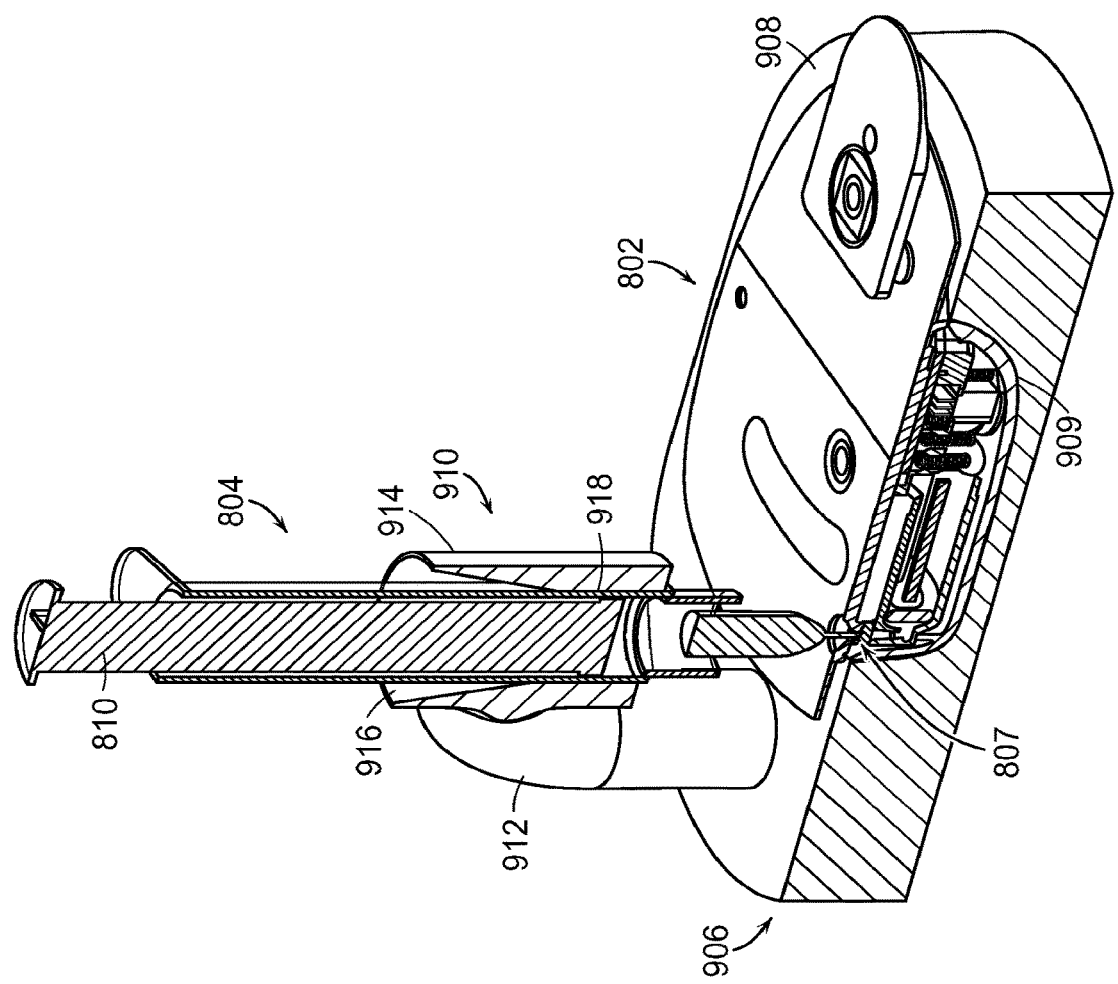
FIG. 9E shows a cut-away isometric view of the alignment device of FIG. 9A.

FIG. 9E shows a cut-away isometric view of the alignment device 906. In FIG. 9E, the alignment device 906 is shown relative to the syringe 804 and the drug delivery device 802. As shown in FIG. 9E, the syringe 804 is positioned within the arm or stem 910 of the alignment device 906. Further, the drug delivery device 802 is positioned within base 908 of the alignment device 906. Specifically, the drug delivery device 802 is positioned within a medical device nest 909 in the base 908 of the alignment device 906. The open area of the base 908 that is designed to accept a portion of the drug delivery device 802 can be considered to be the nest 909. The nest 909 can be shaped and designed to stabilize the drug delivery device 802. As further shown in FIG. 9E, the needle tip 808 of the syringe 804 is positioned directly over the fill port 806 of the drug delivery device 802 so as to access and reach a fill septum 807 of the drug delivery device 802.

The drug delivery device 802 can mate with the base or baseplate 908 of the alignment device 906. As described above, the one or more features of the baseplate 908 in the area or areas at which the drug delivery device 802 mates with the baseplate 908 may be referred to as a nest 909. The nest 909 may allow a specific drug delivery device 802 (e.g., a particular manufacturer and/or brand) and alignment device 906 to mate while preventing other types of medical devices from mating with the alignment device 906. In this way, the size and shape of the nest 909 can be a keying feature of the alignment device 906, and the size and shape of the medical device 802 can be a keying feature of the medical device 802 to mate with the size and shape of the nest 909. In addition, other keying features as described above may be incorporated.

The stem 910 can include a post portion 912 and an alignment cylinder 914. The alignment cylinder 914 has an internal bore for accommodating the syringe 804. The internal bore can have a tapered lead-in geometry defining a conical wall 916 to lead the syringe 804 easily to a lower bore wall 918 that is sized to the syringe diameter to securely hold the syringe 804.

Figure 9G:
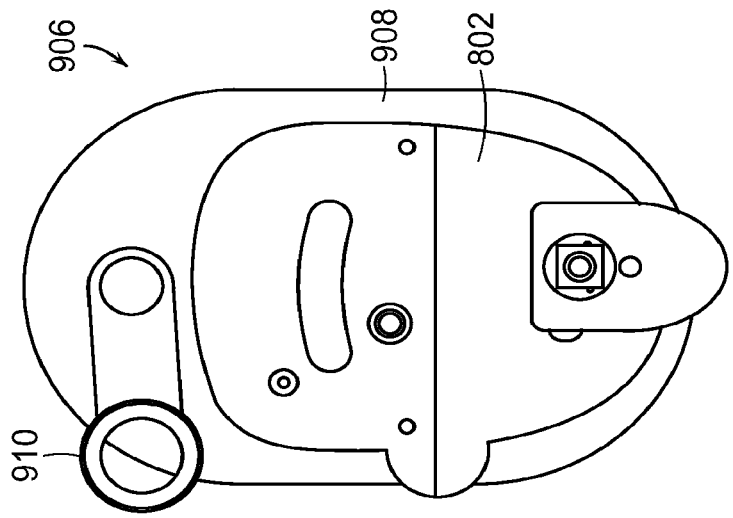
FIGS. 9F and 9G show top views of the alignment device of FIG. 9A illustrating different positioning of a stem of the alignment device.
Figure 9F:
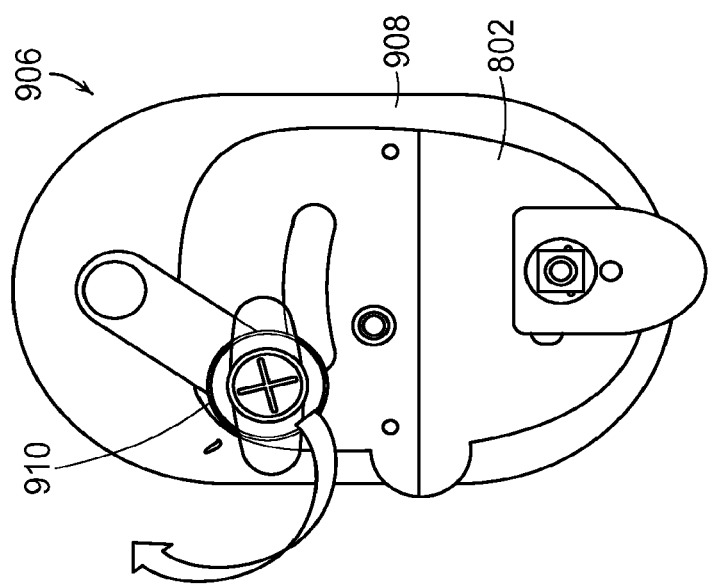

FIGS. 9F and 9G show top views of the alignment device 906 illustrating different positioning of the stem 910. As shown in FIGS. 9F and 9G, the drug delivery device 802 is positioned within the base 908 of the alignment device 906. The arm or stem 910 of the alignment device 906 can either be fixed (e.g., immovable) or can be moved (e.g., rotated) to allow a more open entry and exit of the drug delivery device 802 from the alignment device 906. FIG. 9F shows the stem 910 aligned with the fill port 806 of the medical device 802. FIG. 9G shows the stem 910 in a different position after it has been rotated out of the way to facilitate removal of the drug delivery device 802.

Figure 10C:
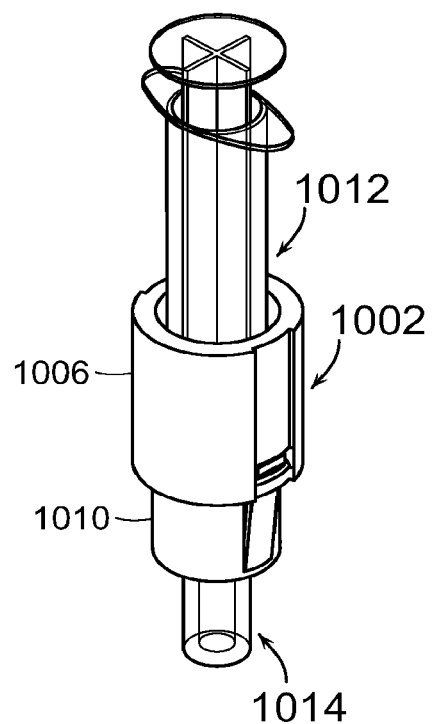

FIGS. 10A through 10M illustrate a system 1000 including a skirt assembly 1002 and alignment device 1070 to assist in filling a medical device 802. FIG. 10A illustrates the skirt assembly 1002. On the left-hand side of FIG. 10A, an exploded view of the skirt assembly 1002 is shown. The skirt assembly 1002 includes a skirt body 1006, a skirt 1010, and a retraction or retract spring 1008. The skirt assembly may also include an optional pressure sensitive adhesive (PSA) 1004 which can be, for example, a double-sided adhesive or tape. The skirt body 1006 and the skirt 1010 can be made from a variety of materials including, for example, a plastic material. The retract spring 1008 can be made from a variety of materials including, for example, a metal material. The skirt assembly 1002 can allow a user to safely and reliably use a syringe and needle to fill a drug delivery device as further described below.

The skirt assembly 1002 can be used with a syringe 1012 and needle cap 1014 as shown in FIG. 10A. The syringe 1012 can be any type of syringe such as, for example, a 2 milliliter (ml) syringe. The needle cap 1014 can be attached to a needle hub 1018 that can be attached to the syringe 1012 as shown. For example, the needle hub 1018 can be screwed on to the syringe 1012. The needle hub 1018 can be attached to a needle 1016 that can extend from the needle hub 1018 into the open area of the needle cap 1014, where it is protected by the needle cap 1014. The syringe 1012, the needle cap 1014, and the skirt assembly 1002 can be aligned as shown in FIG. 10A through FIG. 10C. Once coupled to the syringe 1012, the needle cap 1014 can be removed to expose the needle 1016 that can remain coupled to the syringe 1012 (e.g., along with the needle hub 1018).

FIGS. 10B and 10C show attachment of the skirt assembly 1002 to the syringe 1012 and the needle cap 1014. As shown in FIG. 10B, the skirt assembly 1002 can be axially aligned with the needle cap 1014 and the syringe 1012. The needle cap 1014 can be positioned through a center portion of the skirt assembly 1002. As shown in FIG. 10C, when the syringe 1012 and the skirt assembly 1002 are coupled together, the needle cap 1014 can extend below the skirt 1010, and the skirt body 1006 can extend above the skirt 1010 towards a top end of the syringe 1012. The center portion or opening of the skirt assembly 1002 can be shaped to fit around and to secure the syringe 1012 to the skirt assembly 1002.

Figure 10D:
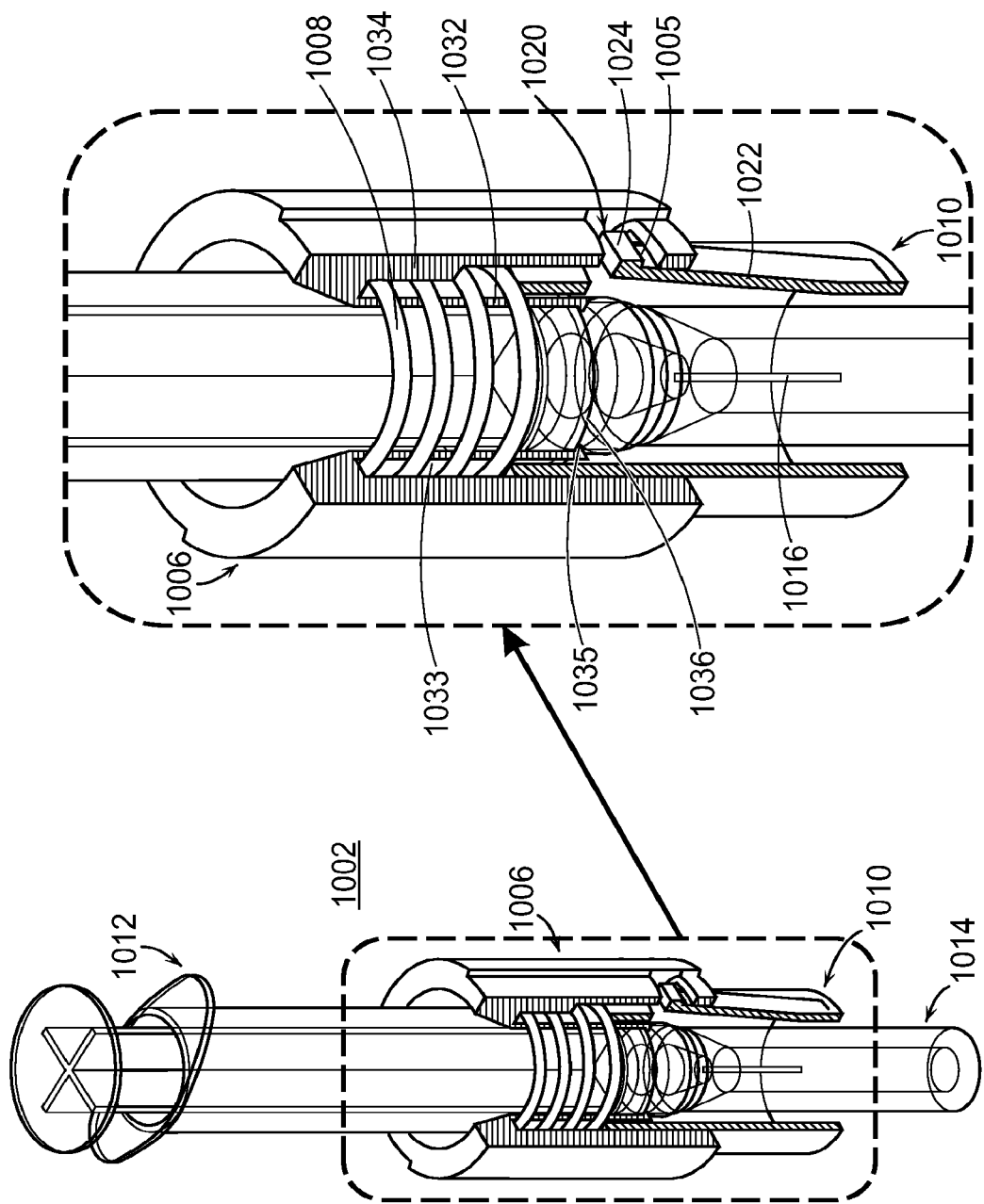

FIG. 10D illustrates additional details on the attachment or coupling of the skirt assembly 1002 to the syringe 1012 and the needle cap 1014. The left-hand side of FIG. 10D shows the skirt assembly 1002 coupled to the syringe 1012 and the needle cap 1014. A portion of the skirt assembly 1002 is removed to reveal the positioning and arrangement of the skirt assembly 1002 relative to the syringe 1012 and the needle cap 1014. As shown, the skirt assembly 1002 is positioned over an area where the syringe 1012 is coupled to the needle cap 1014 with a portion of the needle cap 1014 extending below the skirt 1010.

The right-hand side of FIG. 10D shows a close-up view of the left-hand side of FIG. 10D. As shown, the retract spring 1008 can be positioned above the skirt 1010 between an inner portion (e.g., inner shell) 1032 and an outer portion (e.g., outer shell) 1034 of the skirt body 1006. A portion of the skirt 1010 can be positioned just below the retract spring 1008 between the inner portion 1032 and the outer portion 1034 of the skirt body 1006, with a portion of the skirt 1010 positioned below the skirt body 1006. The skirt body 1006 has a channel 1033 between the inner portion 1032 and the outer portion 1034. The retract spring 1008 is positioned in the channel 1033, and the proximal end of the skirt 1010 is positioned in the channel 1033 abutting against the retract spring 1008. When the syringe 1012 is advanced into the skirt assembly 1002, the syringe 1012 is advanced until a shoulder 1036 on the barrel of the syringe 1012 engages a ledge 1035 at the distal end of the inner portion 1032 of the skirt body 1006, which prevents further movement of the syringe 1012 into the skirt assembly 1002. The inner portion 1032 of the skirt body 1006 can be positioned adjacent to the syringe 1012 to form a tight fit with the syringe 1012. For example, the geometry and shaping of the skirt body 1006 can be aligned to fit around a portion of the syringe 1012 to retain the skirt assembly 1002 in engagement with the syringe in the position shown in FIG. 10D. Additionally or alternatively, an adhesive may be placed on the ledge 1035 such that when the shoulder 1036 is pressed against the ledge 1035 the syringe 1012 becomes secured to the skirt body 1006 and therefore to the skirt assembly 1002. The optional adhesive 1004 may also serve to secure the syringe 1012 to the skirt body 1006 and therefore to the skirt assembly 1002.

The skirt 1010 can include one or more skirt latches 1020 as shown in FIG. 10D. The latches 1020 couple and retain the skirt 1010 to the skirt body 1006 (except when the latches are temporarily unlatched when the skirt assembly is advanced inside the alignment device as described herein). As shown, each skirt latch 1020 comprises a flexure beam 1022 and a latch projection 1024. The skirt body 1006 can include a corresponding opening 1005 for each latch 1020. The opening 1005 on the skirt body 1020 can be positioned in the outer portion 1034 of the skirt body 1006. The opening 1005 can retain the latch projection 1024. The latch projections 1024 and the corresponding openings 1005 on the skirt body 1006 can maintain an orientation of the skirt body 1006 relative to the skirt 1010.

The skirt 1010 can have any number of latches 1020, and the skirt body 1006 can have a corresponding number of openings 1005. The latches 1020 can be molded as part of the skirt 1010. The latches 1020 can be used to keep the skirt 1010 locked to the skirt body 1006, preventing movement of the skirt body 1006 in an axial direction relative to the skirt 1010 (until unlatched). The skirt body 1006 and the skirt 1010 can have any shape. In various embodiments, the skirt body 1006 and the skirt 1010 can have a "clocking" shape— i.e., a non-round/non-circular shape that can be elliptical, square, or other suitable shape. The shape of the skirt body 1006 and the skirt 1010 can help provide alignment with a fill assist device as described in more detail below.

Figure 10F:
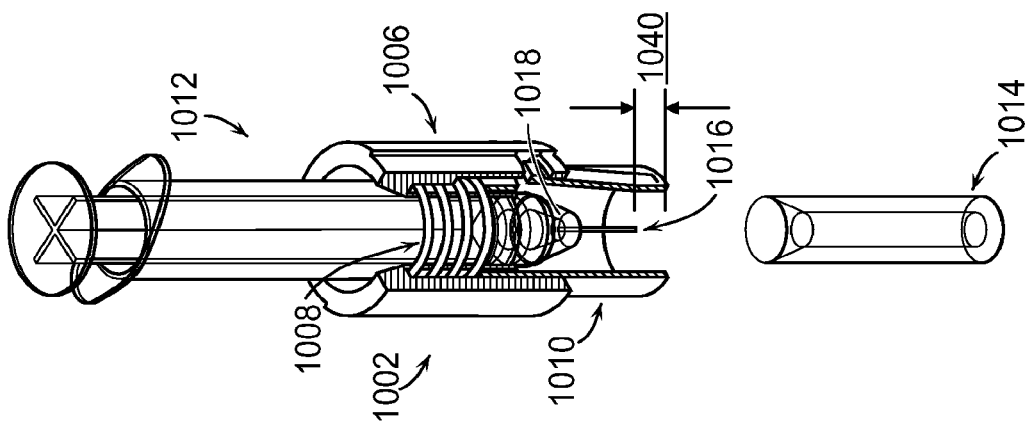
Figure 10E:
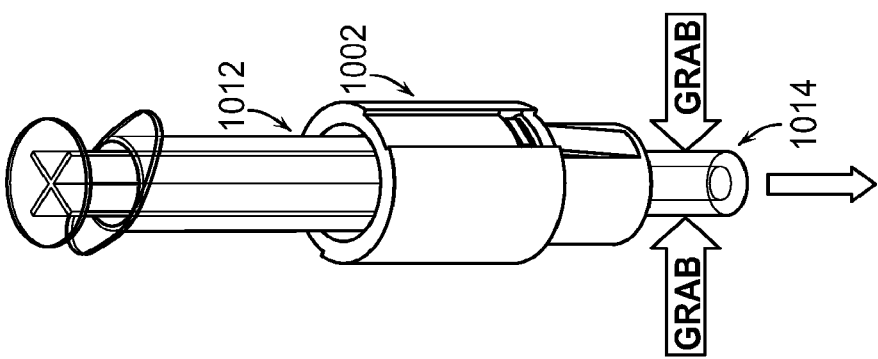

FIGS. 10E and 10F illustrate accessing the needle of the syringe 1012 by removing needle cap 1014. As shown in FIG. 10E, the needle cap 1014 can be removed from the syringe 1012 by grabbing and then pulling down on the needle cap 1014 (e.g., in a downward direction as shown in FIG. 10E). The needle cap 1014 can surround the needle 1016 coupled to the syringe 1012. Accordingly, a user can safely grab and pull down on the needle cap 1014 to remove the needle cap 1014 without coming into contact with the needle 1016. As an example, the needle hub 1018 coupled to the needle 1016 can remain attached to the syringe 1012, and the needle cap 1014 can be removed by pulling down as shown in FIG. 10E.

FIG. 10F shows the needle cap 1014 decoupled from the syringe 1012. Further, FIG. 10F shows a portion of the skirt assembly 1002 removed to show the relative positioning of the syringe 1012, the skirt assembly 1002, and the needle cap 1014. As shown, when the needle cap 1014 is decoupled from the syringe, a needle 1016 coupled to the syringe 1012 is exposed (i.e., no longer covered by the needle cap 1014). The needle 1012 is positioned within an interior portion of the skirt 1010 and can be coupled to or pass through a needle hub 1018 attached to the syringe 1012.

As further shown in FIG. 10F, a space or distance 1040 indicates a distance from a bottom of the skirt 1010 to an end of the needle 1016. That is, the needle 1016 remains a distance 1040 above the bottom of the skirt 1010. As a result, the needle 1016 does not extend below a bottom of the skirt 1010 and is safely retained within the interior portion of the skirt 1010. The positioning of the needle 1016 relative to the skirt 1010 allows a user to safely remove the needle cap 1014 and to manipulate the syringe 1012 and the skirt assembly 1002 with minimized risk of touching the needle 1016. The provided spacing 1040 and the arrangement of the skirt assembly 1002 relative to the syringe 1012 and the needle 1016 can comply with the International Organization for Standardization (ISO) 23908 Sharps Injury Protection standard.

Figure 10H:
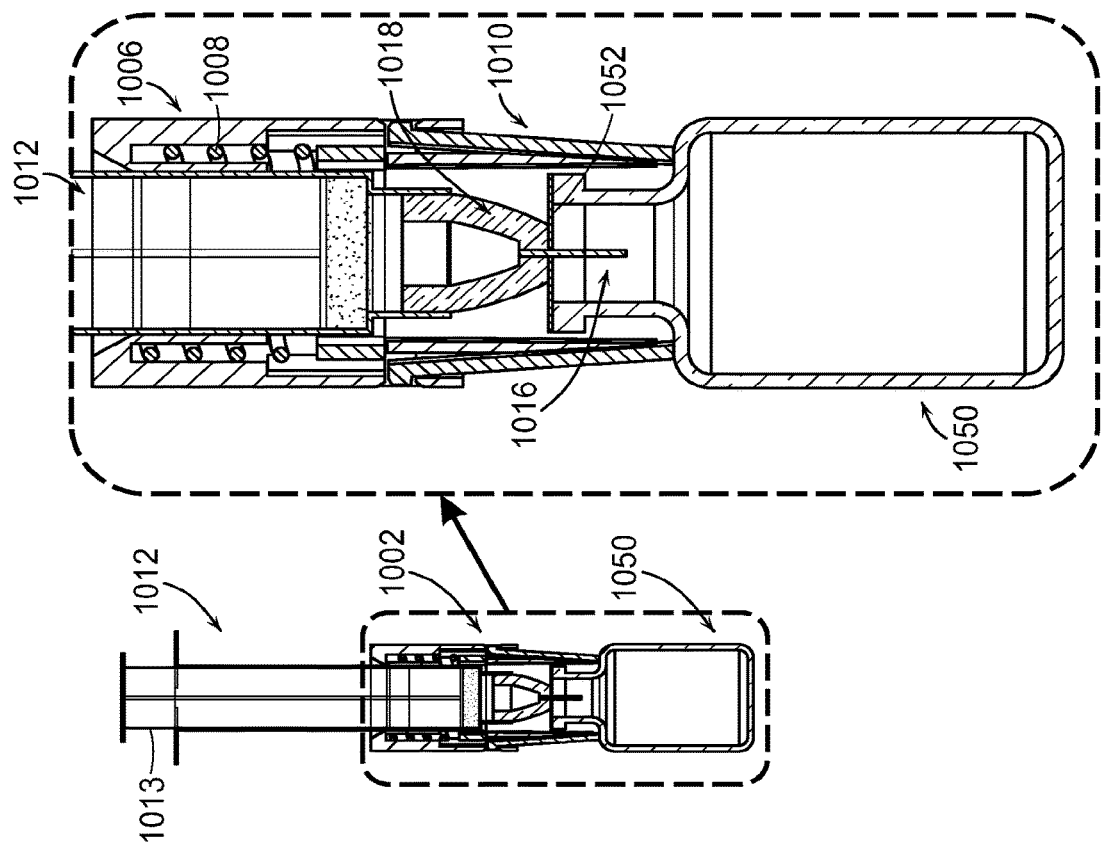
Figure 10G:
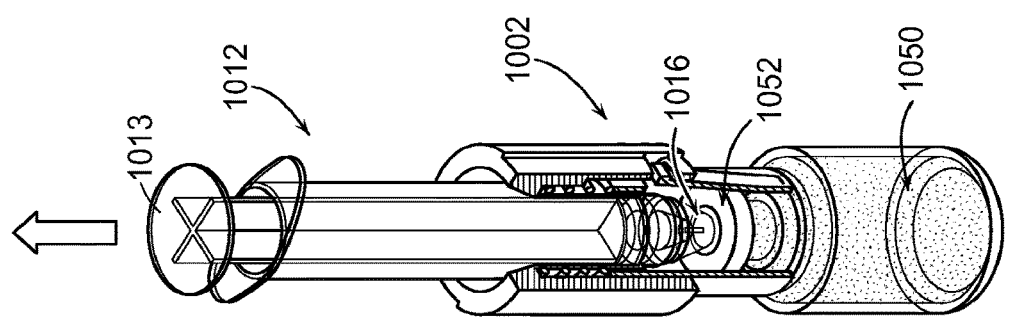

FIGS. 10G and 10H illustrate the skirt assembly 1002 being used to facilitate filling the syringe 1012. As shown in FIG. 10G, the syringe 1012 and the skirt assembly 1002 can be positioned over a liquid drug container 1050. The liquid drug container 1050 can be a vial, cartridge, or other container or closure system or device for retaining or holding a drug. In FIGS. 10G and 10H, the illustrated drug container is a vial 1050. The vial 1050 can hold a liquid drug. A pierceable septum 1052 can be positioned at a top of the vial 1050.

The vial 1050 can hold a liquid drug that is to be transferred into the syringe 1012. To transfer the drug from the vial 1050 to the syringe 1012, the needle 1016 can be positioned over the septum 1052 to pierce the septum 1052. The positioning of the needle 1016 is facilitated by the skirt assembly 1002 because the skirt 1010 is sized to fit over the top portion of the vial 1050 in a way that aligns the needle 1016 with the desired area to be pierced, e.g., the center of the septum 1052. Once the needle 1016 has pierced the septum 1052, the plunger at the proximal end of the syringe 1012 can be pulled to draw the liquid drug out of the vial 1050, through the needle 1016, and into an open chamber of the syringe 1012. When transferring the drug of the vial 1050 into the syringe 1012, the vial 1050 can be oriented below the syringe 1012 or above the syringe 1012 (e.g., opposite to the orientation shown in FIG. 10G).

FIG. 10H shows a close-up view of the positioning of the syringe 1012, the needle 1016, the vial 1050, and the skirt assembly 1002. As shown, the needle 1016 has pierced the septum 1052 and is positioned in a neck or upper region of the vial 1050. The needle 1016 as shown can access the contents of the vial 1050. Support and stability during the transfer process can be provided by a tip of the syringe and/or a bottom portion of the skirt 1010. For example, at a bottom of the syringe 1012, an over-mold 1018 (e.g., needle hub 1018) can be positioned between the needle 1016 and the syringe 1012. The over-mold piece 1018 can surround the needle 1016 while leaving a portion of the needle 1016 exposed when the needle cap 1014 is removed. The over-mold piece 1018 can be a portion of the syringe 1012. Prior to removal, the needle cap 1014 can be coupled to and cover a portion of the over-mold piece 1018, thereby preventing exposure of the needle 1016.

A bottom of the over-mold piece 1018 can rest on a top portion of the vial 1050. This can create a "hard stop" that prevents the needle 1016 from entering further into the vial 1050. The over-mold piece 1018 can also provide stability when the drug is being drawn into the syringe 1012. Further, the bottom of the skirt 1010 can be positioned or can rest on a shoulder of the vial 1050 as shown. Specifically, a neck of the vial 1050 can be positioned within an inner region of the skirt 1010, and the bottom of the skirt 1010 can surround the top of the vial 1050 and can rest against the shoulder of the vial 1050. This can also create a "hard stop" that prevents the needle 1016 from entering further into the vial 1050. The positioning of the bottom of the skirt 1010 and the neck of the vial 1050 can also provide stability when the drug is being drawn into the syringe 1012.

FIGS. 10I and 10J illustrate an initial step for transferring a fluid in the syringe 1012 to a drug delivery device 802. Specifically, FIGS. 10I and 10J show the filled syringe 1012 and the attached skirt assembly 1002 being placed into an alignment device 1070 that aids filling of the drug delivery device 802.

In FIG. 10I, a syringe 1012 with the attached skirt assembly 1002 is shown oriented over the alignment device 1070. The alignment device 1070 can be used to ensure proper alignment of the syringe 1012 and the drug delivery device 802. The alignment device 1070 can be similar to the alignment device 906 as described above in relation to FIGS. 9A through 9G. The drug delivery device 802 can be similar to the drug delivery device 802 depicted and described in relation to FIGS. 9A through 9G. The syringe 1012 as shown in FIG. 10I can be filled with a liquid drug that can be transferred to the drug delivery device 802 using the process illustrated in FIGS. 10I through 10M.

As shown in FIG. 10I, the drug delivery device 802 is positioned within the alignment device 1070. The syringe 1012 with the skirt assembly 1002 is shown being placed into the alignment device 1070 (e.g., into an arbor or extension or arm of the alignment device 1070).

FIG. 10J further shows a cut-away view of the syringe 1012, the skirt assembly 1002, and the alignment device 1070. The alignment device 1070 includes a base 1072 having a nest 1073 for receiving the medical device 802, similar to the medical device nests described above. The alignment device 1070 further includes a stem comprising a post portion 1076 and an alignment cylinder 1078 for receiving and aligning the skirt assembly 1002 and syringe 1012. As shown, the skirt assembly 1002 can be held in a vertical position by the alignment device 1070. Further, the alignment device 1070 can ensure a proper orientation of the needle 1016 of the syringe 1012 relative to the drug delivery device 802 (e.g., the needle 1016 can be positioned above a fill port 806 of the drug delivery device 802). The skirt assembly 1002 can form a tight or snug fit with the alignment cylinder 1078 of the alignment device 1070. A bottom of the skirt 1010 can make contact with the drug delivery device 802, which prevents the skirt 1010 from moving further downward and shields the needle 1016.

The right-hand side of FIG. 10J shows a close-up view of the orientation of the skirt body 1006, the skirt 1010, and a portion of the alignment device 1070. When engaged, the latches 1020 on the skirt 1010 can block or prevent the skirt body 1006 (and, accordingly, the syringe 1012 and needle 1016) from moving downward relative to the skirt 1010. When the syringe 1012 and skirt assembly 1002 are first positioned into the alignment device 1070, the syringe 1012 can be aligned with a fill port 806 of the drug delivery device 802 with a needle 1016 of the syringe 1012 positioned above the fill port 806. The syringe 1012 can further be stabilized by the alignment device 1070 and the skirt assembly 1002, thereby minimizing any risk of the syringe 1012 tipping over or not staying precisely oriented with the drug delivery device 802. As described in more detail below, a force 1026 can be exerted on the latches 1020 to move the latch projections 1024 inward and out of the openings 1005 to enable the skirt body 1006 and syringe 1012 to move relative to the skirt 1010 and closer to the drug delivery device 802 to allow the needle 1016 to access the drug delivery device 802.

FIGS. 10K through 10M illustrate the syringe 1012 accessing the fill port 806 of the drug delivery device 802. FIG. 10K shows that a force exerted downward on the syringe 1012, for example on the barrel or on the plunger of the syringe 1012, can move the syringe 1012 downward so as to push the needle 1016 of the syringe 1012 into the drug delivery device 802.

FIGS. 10L and 10M illustrate how the syringe 1012 can be moved downward. As shown, when the syringe 1012 is pushed downward, the force 1026 presses on the latches 1020. The force 1026 can push the latches 1020 inward, forcing the flexure beams 1022 to flex so that the latch projections 1024 are moved inwardly and out of the openings 1005 in the skirt body 1006. The force 1026 can be introduced by the alignment device 1070 (e.g., by the alignment cylinder 1078) when the syringe 1012 is pushed down. For example, mechanical features in the alignment device 1070 can depress the latches 1020. Force 1026 indicates that the latches 1020 are deflected inward away from the corresponding openings 1005 on the skirt body 1006. The alignment device 1070 can include features to properly align the skirt assembly 1002 within the alignment device 1070 such that the latches 1020 deflect inward as described.

Once the latches 1020 are deflected inward, the syringe 1012 and the skirt body 1006 are able to move downward relative to the skirt 1010. The downward movement of the skirt 1010 can cause not only the disengagement of the latches 1020 but can also cause the distal end of the skirt 1010 to engage the medical device 802, which stops the downward movement of the skirt 1010. As the syringe 1012 continues to be pushed downward, it carries the skirt body 1006 but not the skirt 1010 with it, since the skirt body 1006 has been disengaged from the skirt 1010 and the skirt 1010 is pressed against the medical device 802. As the syringe 1012 and skirt body 1006 move downward relative to the skirt 1010, the skirt 1010 is accommodated further into the channel 1033 of the skirt body 1006 while the spring 1008 compresses. As this happens, the needle 1016 can extend past the end of the skirt 1010 and into the drug delivery device 802. The needle 1016 can extend a distance 1094 from the bottom of the skirt 1010 and into the drug delivery device 802. Because the distal end of the skirt 1010 is pressed against the medical device 802 during this downward motion of the syringe 1012, the needle 1016 is protected from the outside as it enters the medical device 802.

As shown in FIG. 10M, the spring 1008 can be compressed by the downward movement of the skirt body 1006 and the relative upward movement of the skirt 1010 (the skirt 1010 remains pressed against the medical device 802, but there is relative movement between the skirt body 1006 and skirt 1010 due to the downward movement of the skirt body 1006). The spring 1008 provides a reaction force to ensure the skirt 1010 moves downward to re-cover the needle 1016 when the syringe 1012 is removed from the alignment device 1070. When the skirt 1010 is extended by the spring 1008 back to its extended position, the latches 1020 reengage into their corresponding openings 1005 to again lock the skirt 1010 to the skirt body 1006, protecting the needle. In this way, a drug stored in the syringe 1012 can be transferred to the drug delivery device 802 without ever exposing the needle to a user—that is, the needle 1016 can always be covered by the skirt assembly 1002 during the filling process and the transferring process described herein, as well as when the syringe 1012 and skirt assembly 1002 are removed from the alignment device 1070.

The skirt assembly 1002 described herein provides numerous benefits to a user that may need to transfer a liquid from a container or vial to a drug delivery device. The skirt assembly 1002 enables a syringe to be filled from a container or vial and emptied into a drug delivery device without exposing the needle to the user, thereby significantly reducing the likelihood that the user is hurt by the needle or that the needle is damaged. The skirt assembly 1002 can be reused and can be cleaned (e.g., the skirt assembly 1002 can be dishwasher safe). The skirt assembly 1002 can be compatible with existing drug delivery devices (e.g., such as the drug delivery device 802 described above, including the OmniPod® drug delivery device) and existing fill syringes. The skirt assembly 1002 provides sharps protection throughout the filling and emptying processes. The skirt assembly 1002 enables filling using a standard drug container or vial. Further, the skirt assembly 1002 can be manipulated by a user having reduced or impaired motor skills and reduces the likelihood of injury to an impaired user that uses a syringe having an attached skirt assembly 1002. The skirt assembly 1002 also can be manufactured at low cost.

Figure 11:
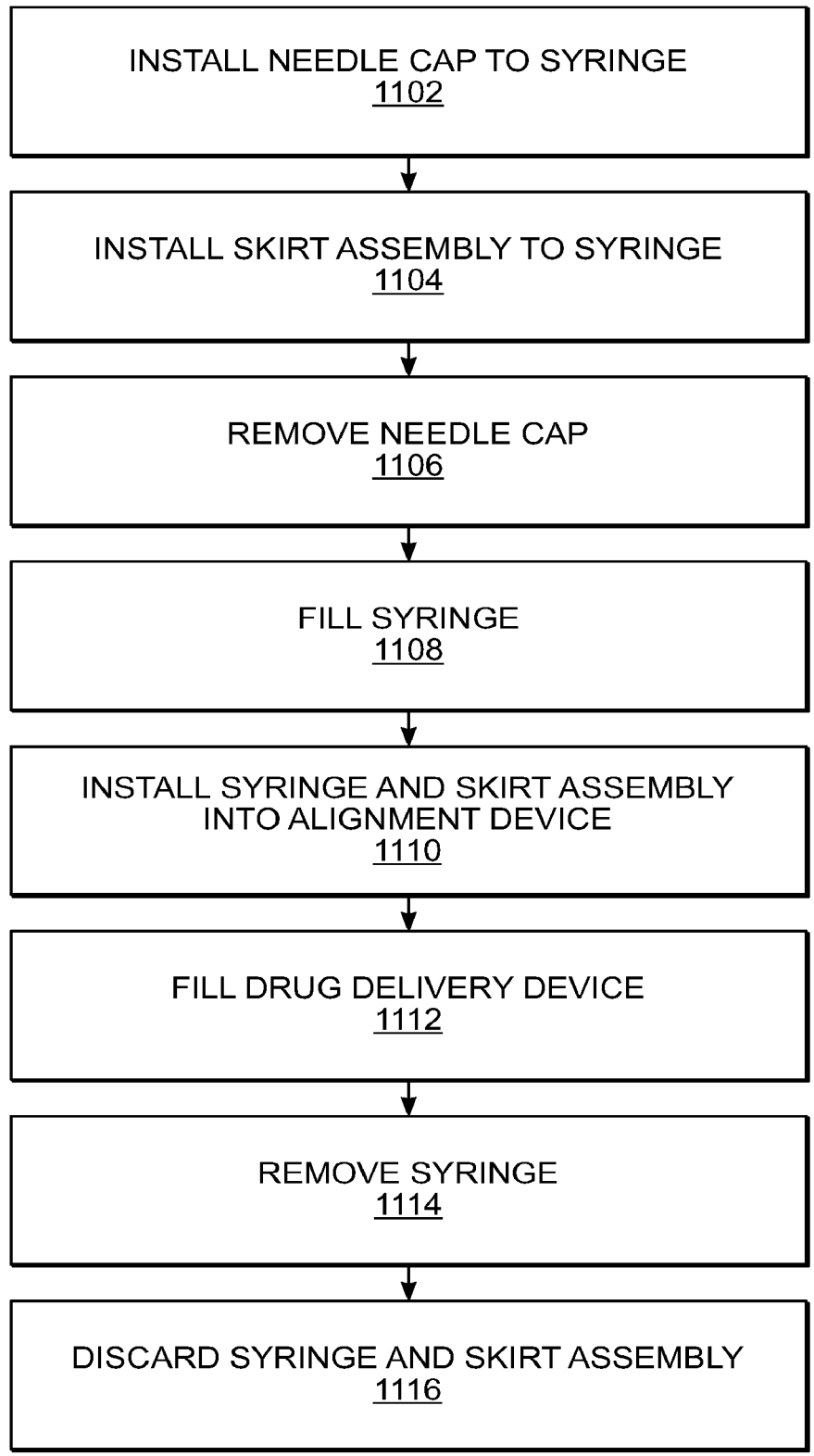
FIG. 11 illustrates a method for using a skirt assembly like the skirt assembly shown in FIGS. 10A through 10M and FIGS. 12A through 12H.

FIG. 11 illustrates a method 1100 for using a skirt assembly (e.g., the skirt assembly 1002) according to the techniques described herein.

At 1102, a needle cap can be installed onto a syringe. The syringe can be designed for use with a particular drug delivery device. The needle cap can be connected to a needle hub that can be screwed onto the syringe. The needle hub can include a needle.

At 1104, a skirt assembly can be installed onto the syringe. The skirt assembly can be positioned on the syringe to cover a portion of the syringe and needle cap. The needle cap can extend below the skirt assembly.

At 1106, the needle cap can be removed. A user can pull down on the needle cap to remove the needle cap (i.e., to decouple the needle cap from the syringe). The needle can remain with the syringe. The skirt assembly can surround the needle to prevent exposure of the needle to the user. The skirt assembly can provide sharps protection according to the ISO 23908 standard.

At 1108, the syringe can be filled. The syringe can be filled with a liquid drug. The syringe can be filled with a liquid drug stored or held in a vial, cartridge, or other container. To fill the syringe, the syringe and skirt assembly can be positioned over the container or vial. The skirt assembly and/or a needle hub can be used to orient and stabilize the syringe relative to the container or vial. Further, the skirt assembly and/or the needle hub can align the needle with a septum of the container or vial positioned at a top of the container or vial. Once stabilized and aligned, the needle can pierce the septum of the container or vial. Once the septum is pierced, the user can pull on a plunger of the syringe to fill the syringe with the liquid contained in the container or vial.

At 1110, once the syringe is filled, the syringe and skirt assembly can be positioned into an alignment device (e.g., the alignment device 1070). The syringe and skirt assembly can be positioned into an arbor or arm extending from a base of the alignment device. When initially positioned into the alignment device, a lower portion of the skirt assembly can rest on top of the drug delivery device. The needle can be positioned above a fill port of the drug delivery device. The alignment device can align the needle with the fill port of the drug delivery device.

At 1112, the drug delivery device can be filled. A skirt of the skirt assembly can retract into a skirt body of the skirt assembly due to a downward force on the syringe. The user's downward force on the syringe can cause latches on the lower portion of the skirt assembly (e.g., the skirt of the skirt assembly) to be pressed inward, thereby allowing the syringe, needle, and upper portion of the skirt assembly (e.g., the skirt body of the skirt assembly) to move further downward. In doing so, the needle can be moved downward and can enter the fill port of the drug delivery device. The lower portion of the skirt assembly or skirt can retract upward relative to the skirt body and can compress a spring, so that the skirt moves within a channel of the skirt body. Features in the arm or arbor of the alignment device can be oriented with the latches of the skirt assembly to cause the latches to move inward to allow free movement of the syringe and upper portion of the skirt assembly, thereby allowing the needle to reach the fill port of the drug delivery device.

Once the needled is positioned in the drug delivery device, the drug delivery device can be filled. The liquid stored in the syringe can be transferred into the drug delivery device through the needle and fill port. By pushing down on the plunger, the user can force the fluid out of the syringe.

At 1114, the syringe and skirt assembly can be removed from the alignment device. The filled drug delivery device can then be ready for use. When the syringe is pulled up out of the alignment device by the user, the compressed spring can cause the lower portion of the skirt assembly, i.e., the skirt, to move downward relative to the skirt body. Thus, the lower portion of the skirt assembly or skirt can immediately and automatically extend back into position, covering the needle and ensuring that the needle is not exposed. When the skirt is extended back into its extended position, the latches reengage into their corresponding openings, locking the skirt again to the skirt body, and preventing it from being pressed back to expose the needle. Sharps protection is therefore once again provided when the syringe and skirt assembly are separated from the alignment device.

At 1116, the syringe and/or the skirt assembly can be disposed of or discarded. The skirt assembly can be recycled or cleaned and reused if desired.

Figure 12A:
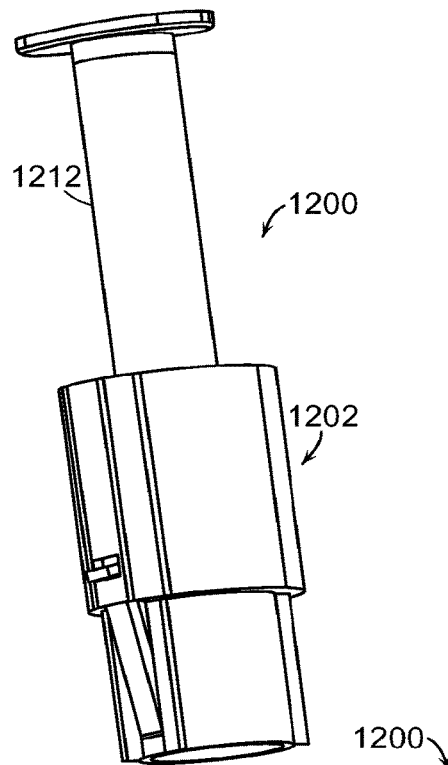
Figure 12B:
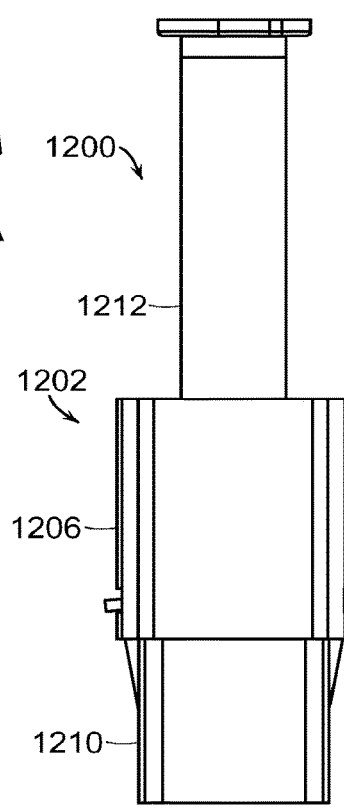
Figure 12C:
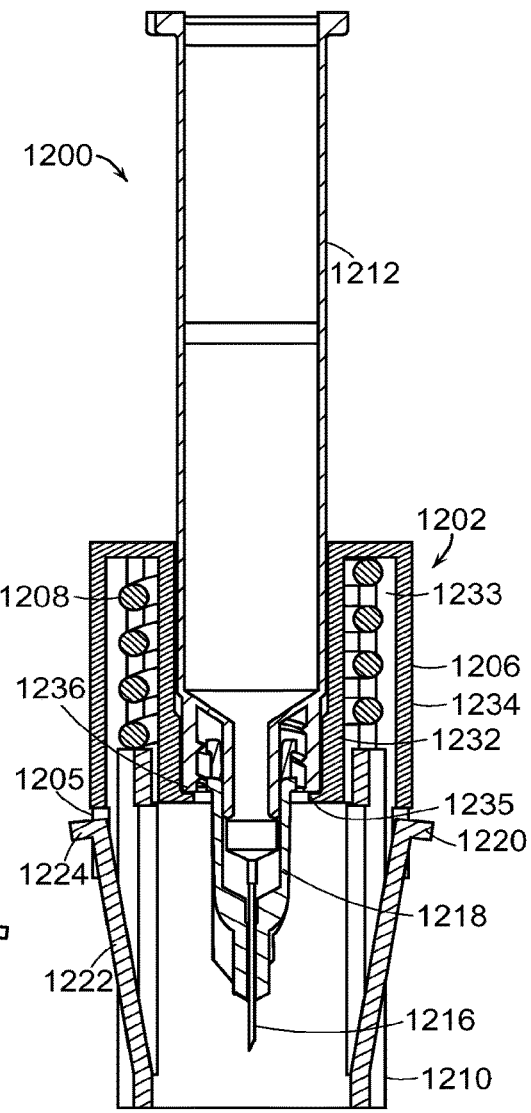

FIGS. 12A through 12H illustrate a system 1200 including a skirt assembly 1202 and alignment device 1270 to assist in filling a medical device 802. In many respects the system 1200 and its components are similar to the system 1000 and its components as described above. FIG. 12A illustrates a syringe 1212 inserted into a skirt assembly 1202. FIG. 12B shows a side view of the syringe 1212 and skirt assembly 1202 of FIG. 12A. FIG. 12C shows a cross-sectional view corresponding to FIG. 12B. As can be seen in FIG. 12C, the skirt assembly 1202 includes a skirt body 1206, a skirt 1210, and a retraction or retract spring 1208. The skirt body 1206 and the skirt 1210 can be made from a variety of materials including, for example, a plastic material. The retract spring 1208 can be made from a variety of materials including, for example, a metal material.

The skirt assembly 1202 can be used with a syringe and needle cap similar to the syringe 1012 and needle cap 1014 as shown in FIG. 10A. The syringe 1212 can be any type of syringe such as, for example, a 2 milliliter (ml) syringe. The needle cap can be attached to a needle hub 1218 that can be attached to the syringe 1212 as shown. For example, the needle hub 1218 can be screwed on to the syringe 1212. The needle hub 1218 can be attached to a needle 1216 that can extend from the needle hub 1218 into the open area of the needle cap, where it is protected by the needle cap. When the syringe 1212 and the skirt assembly 1202 are coupled together, the needle cap can extend below the skirt 1210. Once coupled to the syringe 1212, the needle cap can be removed to expose the needle 1216 that can remain coupled to the syringe 1212 (e.g., along with the needle hub 1218). The needle cap can be removed as described above with respect to FIGS. 10E and 10F. When the needle cap is removed, the needle 1216 remains a distance similar to the distance 1040 above the bottom of the skirt 1210. As a result, the needle 1216 does not extend below a bottom of the skirt 1210 and is safely retained within the interior portion of the skirt 1210. The positioning of the needle 1216 relative to the skirt 1210 allows a user to safely remove the needle cap and to manipulate the syringe 1212 and the skirt assembly 1202 with minimized risk of touching the needle 1216. The provided spacing and the arrangement of the skirt assembly 1202 relative to the syringe 1212 and the needle 1216 can comply with the ISO 23908 Sharps Injury Protection standard.

As shown in FIG. 12C, the retract spring 1208 can be positioned above the skirt 1210 between an inner portion (e.g., inner shell) 1232 and an outer portion (e.g., outer shell) 1234 of the skirt body 1206. A portion of the skirt 1210 can be positioned just below the retract spring 1208 between the inner portion 1232 and the outer portion 1234 of the skirt body 1206, with a portion of the skirt 1210 positioned below the skirt body 1206. The skirt body 1206 has a channel 1233 between the inner portion 1232 and the outer portion 1234. The retract spring 1208 is positioned in the channel 1233, and the proximal end of the skirt 1210 is positioned in the channel 1233 abutting against the retract spring 1208. When the syringe 1212 is advanced into the skirt assembly 1202, the syringe 1212 is advanced until a shoulder 1236 on the barrel of the syringe 1212 engages a ledge 1235 at the distal end of the inner portion 1232 of the skirt body 1206, which prevents further movement of the syringe 1212 into the skirt assembly 1202. When the syringe 1212 is inserted into the skirt assembly 1202, the inner portion 1232 of the skirt body 1206 can form a tight fit with the syringe 1212. For example, the geometry and shaping of the skirt body 1206 can be aligned to fit around a portion of the syringe 1212 to retain the skirt assembly 1202 in engagement with the syringe in the position shown in FIG. 12C. Additionally or alternatively, an adhesive may be placed on the ledge 1235 such that when the shoulder 1236 is pressed against the ledge 1235 the syringe 1212 becomes secured to the skirt body 1206 and therefore to the skirt assembly 1202.

The skirt 1210 can include one or more skirt latches 1220 as shown in FIG. 12C. The latches 1220 can be used to couple and to retain the skirt 1210 to the skirt body 1206. As shown, each skirt latch 1220 comprises a flexure beam 1222 and a latch projection 1224. The skirt body 1206 can include a corresponding opening 1205 for each latch 1220. The opening 1205 on the skirt body 1220 can be positioned in the outer portion 1234 of the skirt body 1206. The opening 1205 can retain the latch projection 1224. The latch projections 1224 and corresponding openings 1205 on the skirt body 1206 can maintain an orientation of the skirt body 1206 relative to the skirt 1210.

The skirt 1210 can have any number of latches 1220, and the skirt body 1206 can have a corresponding number of openings 1205. The latches 1220 can be molded as part of the skirt 1210. The latches 1220 keep the skirt 1210 locked to the skirt body 1206, preventing movement of the skirt body 1206 in an axial direction relative to the skirt 1210 (except when the latches are temporarily unlatched when the skirt assembly is advanced inside the alignment device as described herein). The skirt body 1206 and the skirt 1210 can have any shape. In various embodiments, the skirt body 1206 and the skirt 1210 can have a "clocking" shape—i.e., a non-round/non-circular shape that can be elliptical, square, or other suitable shape. The shape of the skirt body 1206 and the skirt 1210 can help provide alignment with a fill assist device as described in more detail below.

The skirt assembly 1202 can be used to facilitate filling the syringe 1212 in a manner similar to that described above with respect to FIGS. 10G and 10H and the vial 1050. The skirt 1210 may be sized to fit over the top portion of the vial 1050 in a way that aligns the needle 1216 with the desired area to be pierced, e.g., the center of the septum 1052. The needle hub 1218 can be sized to abut a top portion of the vial 1050, creating a "hard stop" that prevents the needle 1216 from entering further into the vial 1050. Further, the bottom of the skirt 1210 can be sized to abut a shoulder of the vial 1050 as shown in FIGS. 10G and 10H, creating an alternative or additional "hard stop" that prevents the needle 1216 from entering further into the vial 1050. A neck of the vial 1050 can be positioned within an inner region of the skirt 1210, and the bottom of the skirt 1210 can surround the top of the vial 1050, abutting the shoulder of the vial 1050.

FIGS. 12D through 12F illustrate an alignment device 1270 for transferring a fluid in the syringe 1212 to a drug delivery device 802. The filled syringe 1212 and the attached skirt assembly 1202 are placed into the alignment device 1270 for filling of the drug delivery device 802.

The alignment device 1270 can be used to ensure proper alignment of the syringe 1212 and the drug delivery device 802. The alignment device 1270 can be similar to the alignment device 906 as described above in relation to FIGS. 9A through 9G. The drug delivery device 802 can be similar to the drug delivery device 802 depicted and described in relation to FIGS. 9A through 9G. The syringe 1212 can be filled with a liquid drug that can be transferred to the drug delivery device 802 using the alignment device 1270.

FIG. 12D shows a perspective view of the alignment device 1270 with the drug delivery device 802 in place. FIG. 12E shows a perspective view of the alignment device 1270 with the syringe 1212 and attached skirt assembly 1202 loaded into the alignment device 1270. FIG. 12F shows a top view of the alignment device 1270 with the drug delivery device 802 in place and the syringe 1212 and attached skirt assembly 1202 loaded into the alignment device 1270. The alignment device 1270 includes a base 1272 having a nest 1273 for receiving the medical device 802, similar to the medical device nests described above. The alignment device 1270 further includes a stem comprising a post portion 1276 and an alignment cylinder 1278 for receiving and aligning the skirt assembly 1202 and syringe 1212. As shown, the skirt assembly 1202 can be held in a vertical position by the alignment device 1270. Further, the alignment device 1270 can ensure a proper orientation of the needle 1216 of the syringe 1212 relative to the drug delivery device 802 (e.g., the needle 1216 can be positioned above a fill port 806 of the drug delivery device 802). The skirt assembly 1202 can form a tight or snug fit with the alignment cylinder 1278 of the alignment device 1270. When fully loaded, a bottom of the skirt 1210 can make contact with the drug delivery device 802.

In a similar manner as described above with respect to FIGS. 9F and 9G, the alignment device 1270 may be moved between a first position in which the alignment cylinder 1278 is away from the nest 1273 and a second position in which the alignment cylinder 1278 is above the nest 1273 to align the needle 1216 of the syringe 1212 with the fill port 806 of the drug delivery device 802. FIG. 12F shows the alignment device 1270 in the second position. The alignment device 1270 further comprises a ball spring detent 1280 for holding the alignment device 1270 in the first position and the second position and for facilitating easy movement between the two positions. The ball spring detent 1280 moves in a track 1282 which has two recess 1284, one corresponding to the first position and the other corresponding to the second position. In either position, the ball spring detent is pushed by spring force into the recess 1284 to hold the alignment cylinder 1278 in place. A user can apply a sufficient amount of force to overcome the spring force holding the ball spring detent in one of the recesses 1284 in order to move the alignment cylinder 1278 from one of the positions to the other.

Figure 12G:
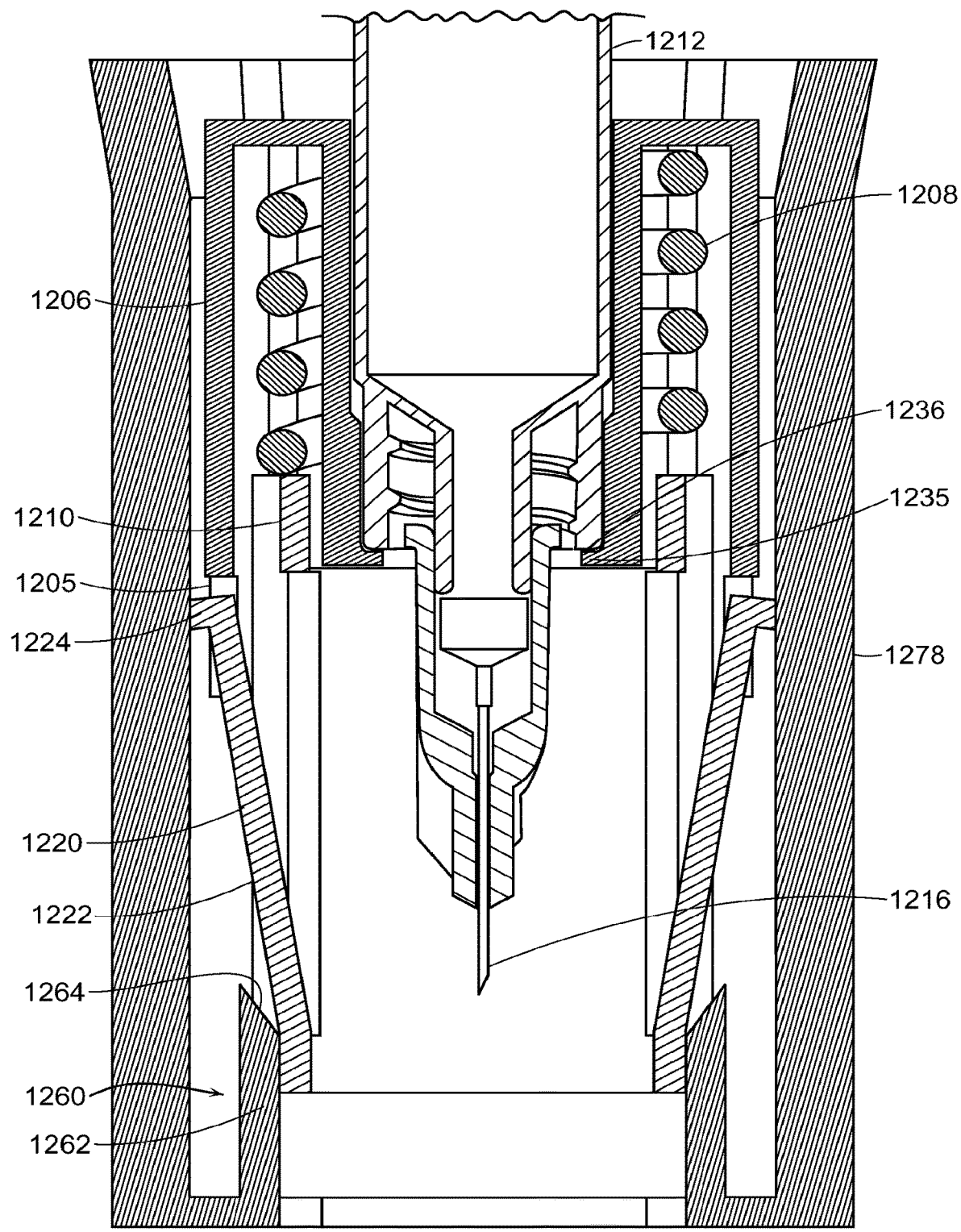
Figure 12H:
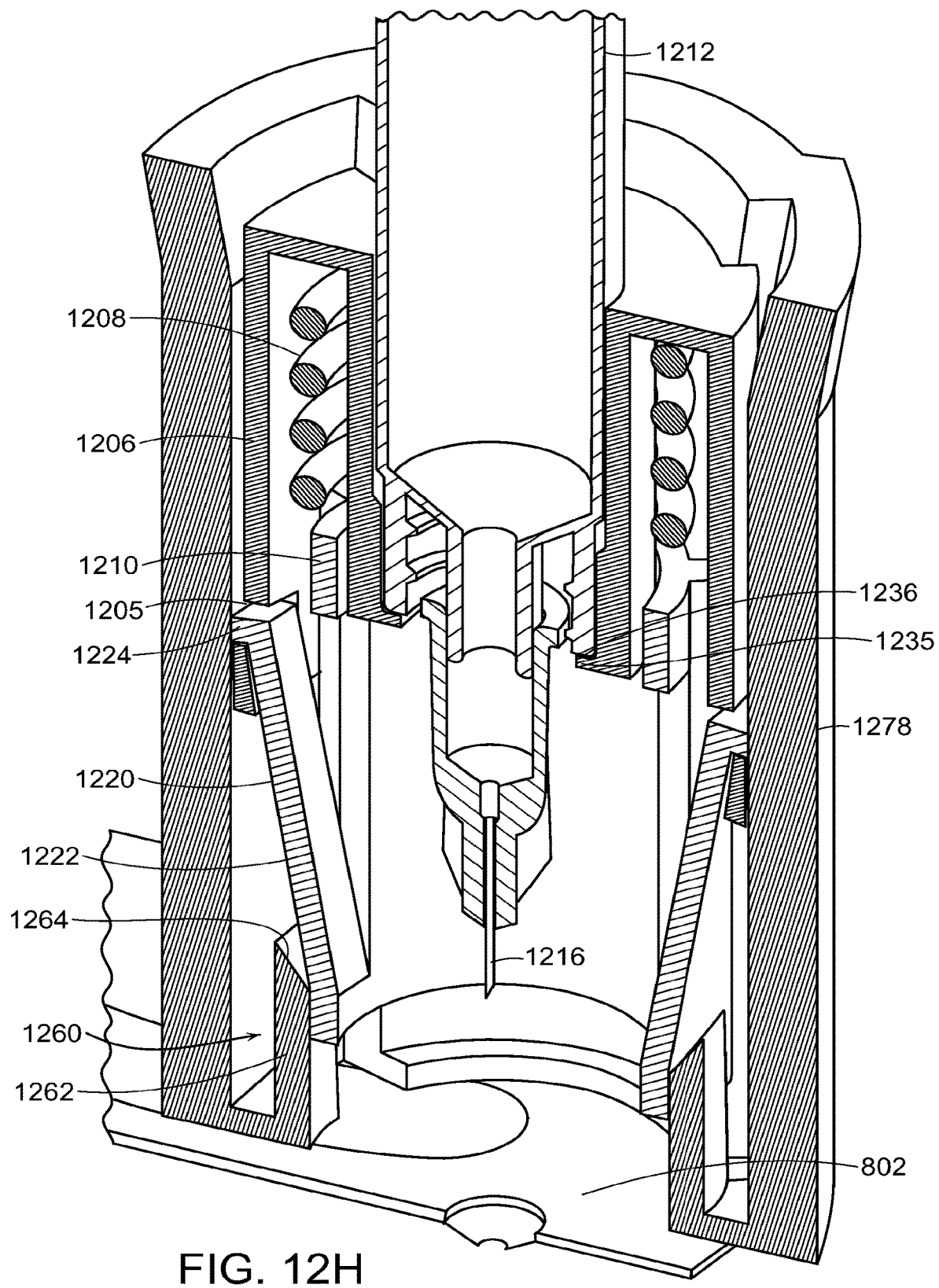

FIG. 12G shows a cross-sectional view of the syringe 1212 and skirt assembly 1202 loaded into the alignment cylinder 1278 of the alignment device 1270. FIG. 12H shows a perspective view in cross-section of the syringe 1212 and skirt assembly 1202 loaded into the alignment cylinder 1278 of the alignment device 1270, positioned over a medical device 802. As shown, the latches 1220 on the skirt 1210 can block or prevent the skirt body 1206 (and, accordingly, the syringe 1212 and needle 1216) from moving downward relative to the skirt 1210.

A force exerted downward on the syringe 1212 can move the syringe 1212 and skirt assembly 1202 downward. When the syringe 1212 is pushed downward, the skirt assembly 1202 travels with it, forcing the latches 1220 against the latch disengagement mechanism 1260. In this embodiment, the latch disengagement mechanism 1260 is part of the alignment cylinder 1278 of the alignment device 1270, and the latch disengagement mechanism 1260 comprises one or more posts 1262 each of which terminates in an inclined surface 1264. As the syringe 1212 and therefore the skirt body 1206 and skirt 1210 are advanced into the alignment cylinder 1278, the skirt latches 1220 come into contact with the latch disengagement mechanism 1260. Advancement of the skirt 1210 causes the flexure beams 1222 of the latches 1220 to engage the inclined surfaces 1264 of the latch disengagement mechanism 1260, which causes the flexure beams 1222 to flex inward. This moves the latch projections 1224 inwardly and out of the openings 1205 in the skirt body 1206.

Once the latches 1220 are deflected inward and the latch projections 1224 are out of the openings 1205, the syringe 1212 and the skirt body 1206 are able to move downward relative to the skirt 1210. The downward movement of the skirt 1210 causes not only the disengagement of the latches 1220 but also causes the distal end of the skirt 1210 to engage the medical device 802, which stops the downward movement of the skirt 1210. As the syringe 1212 continues to be pushed downward, it carries the skirt body 1206 but not the skirt 1210 with it, since the skirt body 1206 has been disengaged from the skirt 1210 and the skirt 1210 is pressed against the medical device 802. As the syringe 1212 and skirt body 1206 move downward relative to the skirt 1210, the skirt 1210 is accommodated further into the channel 1233 of the skirt body 1206 while the spring 1208 compresses. As this happens, the needle 1216 can extend past the end of the skirt 1210 and into the drug delivery device 802. The needle 1216 can extend a distance similar to the distance 1094 from the bottom of the skirt 1210 and into the drug delivery device 802. Because the distal end of the skirt 1210 is pressed against the medical device 802 during this downward motion of the syringe 1212, the needle 1216 is protected from the outside as it enters the medical device 802.

The spring 1208 can be compressed by the downward movement of the skirt body 1206 (the skirt 1210 remains pressed against the medical device 802). The spring 1208 provides a reaction force to ensure the skirt 1210 moves downward to re-cover the needle 1216 when the syringe 1212 is removed from the alignment device 1270. When the skirt 1210 is extended by the spring 1208 back to its extended position, the latches 1220 reengage into their corresponding openings 1205 to again lock the skirt 1210 to the skirt body 1206, protecting the needle. In this way, a drug stored in the syringe 1212 can be transferred to the drug delivery device 802 without ever exposing the needle to a user—that is, the needle 1216 can always be covered by the skirt assembly 1202 during the filling process and the transferring process described herein, as well as when the syringe 1212 and skirt assembly 1202 are removed from the alignment device 1270.

The skirt assembly 1202 provides advantages similar to those described above with respect to the skirt assembly 1002. It allows a user to easily, safely, and reliably transfer a liquid drug from a container or vial to a drug delivery device.

As discussed above, an attachment or cap configured to be fitted onto a container (e.g., a vial) holding liquid medication may include one or more features that cover the septum or other entryway into the container. When a suitable needle hub is inserted into the cap, it engages the feature(s) to uncover the septum, thereby permitting access to the medication. In various embodiments, the cap and/or needle hub may include other features, such as keying features or protrusions, that permit only a needle hub of a certain type to be inserted into the cap and uncover the septum—a needle hub of the wrong type is not permitted to enter the cap and uncover the septum. A person may mate the syringe with the container, withdraw medication therefrom, and thereafter mate the syringe with the drug delivery medical device and dispense the medication thereto. A drug may thus be transferred from a container or vial to a drug delivery medical device without giving the person conducting the transfer the ability to access the drug via an alternate method and to minimize tamper. In other words, the syringe matches or has keying features matching the container or vial and the drug delivery medical device, so that only the correct container or vial and drug delivery medical device can be accessed by the syringe, thereby ensuring that the correct drug is transferred from the correct matching container or vial to the correct matching drug delivery medical device.

Figure 13:
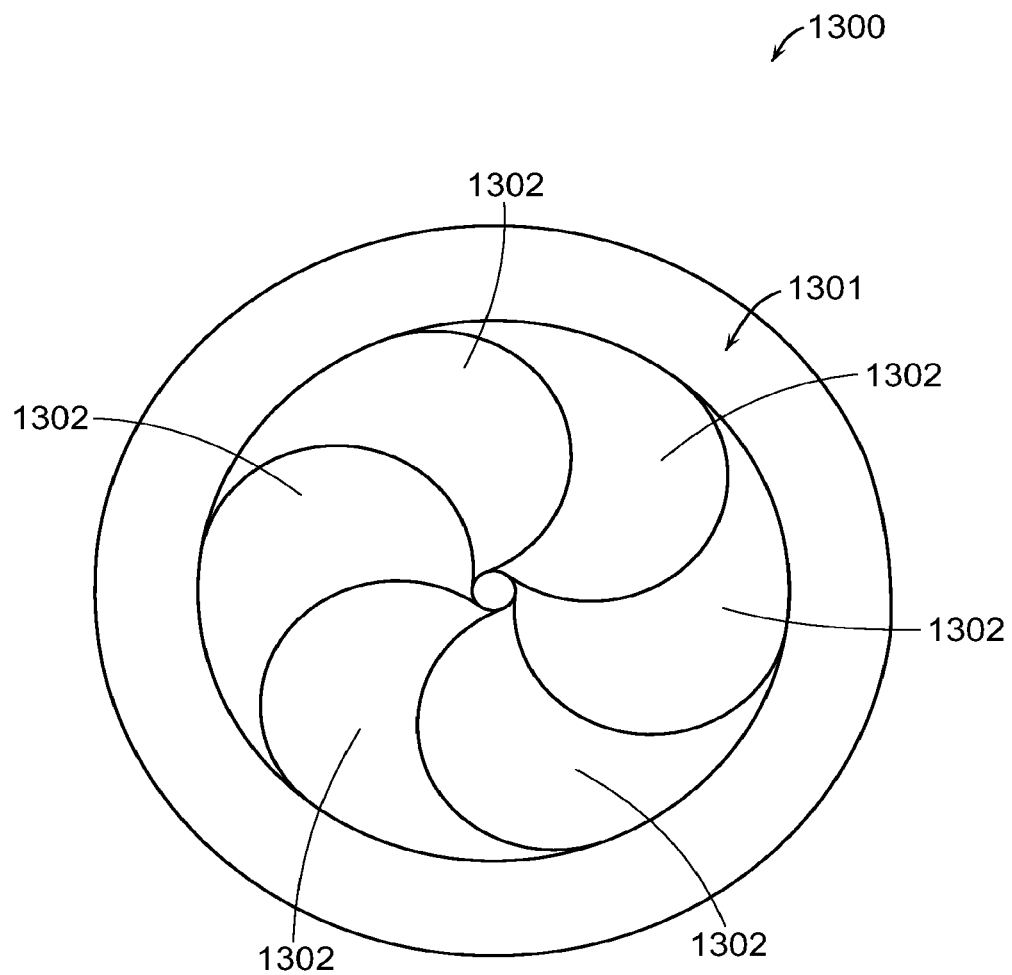
FIG. 13 shows a cap for a liquid drug container or medical device wherein the cap has an iris.

In one such embodiment, as shown in FIG. 13, the cap 1300 includes an iris 1301. The iris 1301 comprises a series of movable iris elements 1302. When a needle hub enters the cap 1300, it may be engaged with one or more features of the iris 1301 and/or features connected thereto and rotated, thereby causing the iris 1301 to open (e.g., the iris elements 1302 of the iris 1301 move away from the center), thereby creating an opening to allow the needle to enter the liquid drug container and/or medical device associated with the cap 1300. In other embodiments, the needle hub and/or cap includes an element that translates straight-line motion to rotational motion (such as a cam); in these embodiments, the iris 1301 may be opened by simply inserting the needle hub into the cap without rotating it. The cap, iris, and/or cam may be formed using any material, such as molded plastic.

In another embodiment, as shown in FIGS. 14A through 14C, the cap 1400 includes one, two, or more bendable features 1402 that, when not acted upon by an outside force, cover the opening of a liquid drug container and/or a fill port of a medical device, such as the septum 1452 of the container or vial 1450. A needle hub 1430 may be configured to include protruding features 1432 that, when the needle hub 1430 is inserted into the cap 1400, engage with the one or more bendable features 1402. In some embodiments, the needle hub protruding features 1432 extend past a length of the needle 1434. When the needle hub 1430 enters the cap 1400, it and/or protruding features 1432 disposed thereon exert a force on the bendable members 1402 such that the bendable members 1402 are pushed down (i.e., in the direction of motion of the needle hub 1430). The bendable feature(s) 1402 include a pass-through point 1404, such as a hole, along their length. When the bendable feature(s) 1402 are pushed down to a certain point and/or fully pushed down, the pass-through(s) 1404 align with the entryway to the fill port or container or vial 1450 (and each other if using two features), allowing the needle 1434 to enter the container or vial 1450. The needle hub protruding features 1432 may be configured to be stiffer than the cap bendable features 1402 so that the needle hub protruding features 1432 do not bend or compress, or do so only negligibly, before the cap bendable features 1402 have bottomed out. The needle 1434 may be advanced relative to the needle hub protruding features 1432 in order to be extended through the pass-through(s) 1404 and into the fill port or container or vial 1450.

Figure 15A:
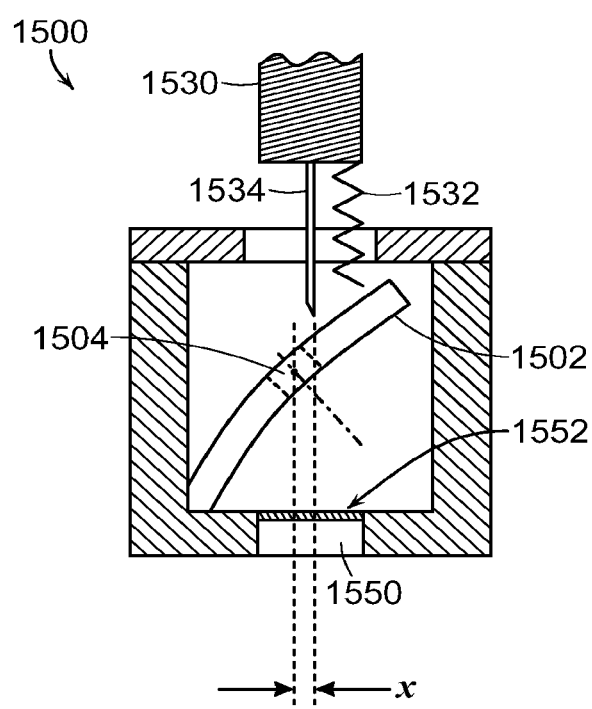
FIGS. 15A and 15B show another embodiment of a cap for a liquid drug container or medical device and a corresponding needle hub, wherein the cap has one or more bendable features or doors.
Figure 15B:
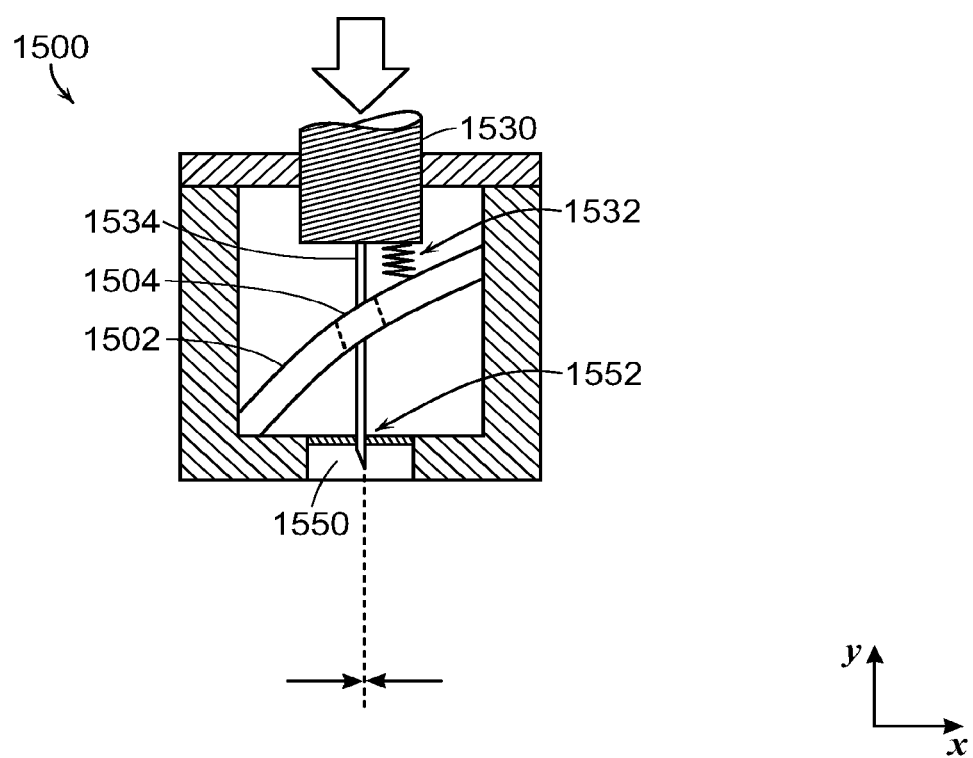

In other embodiments, the needle hub protrusions are springs or any other flexible material, as shown in FIGS. 15A and 15B. In these embodiments, the springs 1532 may exert a force on the bendable members 1502 instead of, or in addition to, the protruding features discussed above. In some embodiments, the spring constant of the springs 1532 is greater than the spring constant of the bendable features 1502 (i.e., the springs 1532 are "stiffer" than the bendable features 1502). In these embodiments, upon initial contact of the springs 1532 and bendable members 1502, the bendable members 1502 are pushed down while the springs 1532 do not move or distort (or do so only negligibly).

In some embodiments, the cap 1500 features a mechanical stop to halt further motion of the needle hub 1530 toward the medical device fill port or vial 1550 and septum 1552. The mechanical stop may be configured such that, when the needle hub 1530 reaches the mechanical stop, the pass-through points 1504 of the bendable member(s) 1502 are aligned over the fill port or opening of the vial 1550. If two or more features 1502 are used to cover the septum 1552, the pass-through points 1504 may align once the features 1502 have bottomed out, allowing the needle 1534 to extend through the pass-through points 1504. If one feature 1502 is used, the cap 1500 may contain a smaller hole underneath the feature 1502 that aligns with the pass-through 1504 once the feature 1502 has bottomed out, allowing the needle 1534 to extend through the pass-through point 1504 and the smaller hole in the cap 1500. In FIG. 15A, the distance x indicates a distance from the lockout axis (left dashed line) to the needle axis (right dashed line). In FIG. 15B, the bendable feature 1502 has been compressed to a hard stop position against the inside wall of the cap 1500, the spring 1532 is compressed, and the needle 1534 is extended to pierce the septum 1552 and enter the liquid drug region of the vial 1550.

In other embodiments, as shown in FIGS. 16A and 16B, a magnetic feature 1602 in the cap 1600 slidably covers the fill port of the medical device or the septum 1652 of the vial 1650. The feature 1602 may be constructed from a ferromagnetic material, rare-earth magnet, or any other magnetic material. A magnetic field may be applied to the cap 1600 to open the feature 1602 and expose the fill port or septum 1652 via the use of magnetic attraction or repulsion; as the feature 1602 is exposed to the magnetic field, it slides or moves in response, allowing the needle 1634 to access the septum 1652. The feature 1602 may be disposed in a slidable housing that permits the feature 1602 to move or slide only within a certain dimension or distance. The magnetic field may be provided by a magnet disposed in the needle hub 1630 or in another device.

Figure 17A:
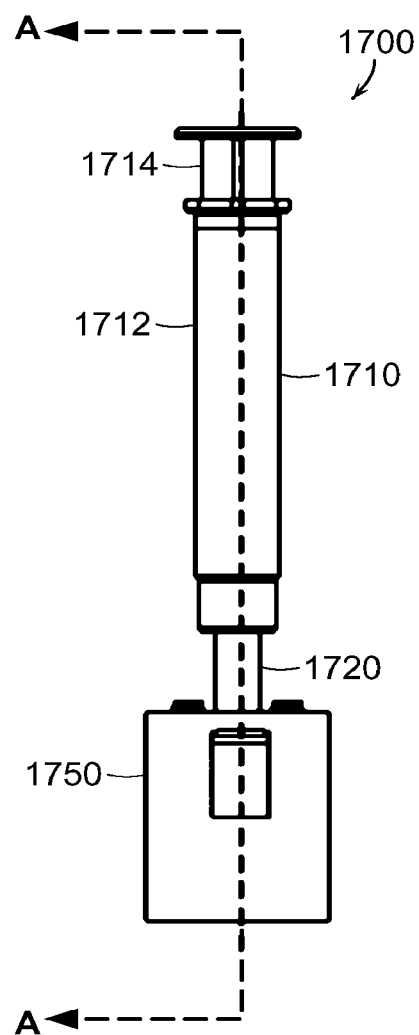
Figure 17B:
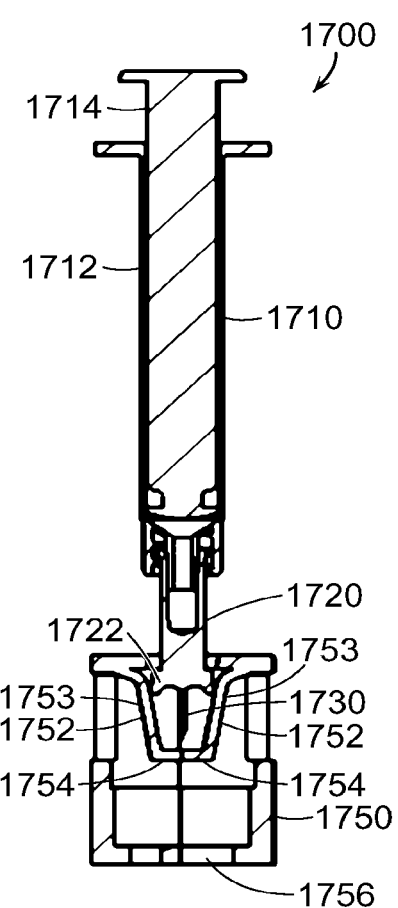

FIGS. 17A through 17H illustrate a system 1700 comprising a syringe 1710, needle hub 1720, and vial adapter or cap 1750 in accordance with other embodiments. FIG. 17A shows a side view of the system 1700, and FIG. 17B shows a cross-sectional view taken along the line A-A in FIG. 17A. The syringe 1710 comprises a syringe barrel 1712 and a plunger 1714. The needle hub 1720 is attached to the syringe 1710, for example by a Luer connection, and carries a needle 1730. The needle hub 1720 has one, two, or more engagement features or key features 1722. The cap 1750 is adapted to fit onto and attach to a liquid drug container or vial. Alternatively, the cap 1750 may cover a fill port of a medical device. In the illustrated example, the cap 1750 has a vial opening 1756 that can receive the neck of a liquid drug container or vial such that in use a top of the vial is located inside of the cap 1750 and the lower part of the vial (below the neck) is located outside of the cap 1750. The cap 1750 may be made from molded plastic and may have one, two, or more slanted arms or doors 1752 that flex or pivot when the key features 1722 of the needle hub 1720 (attached to the syringe 1710) contact them.

Figure 17C:
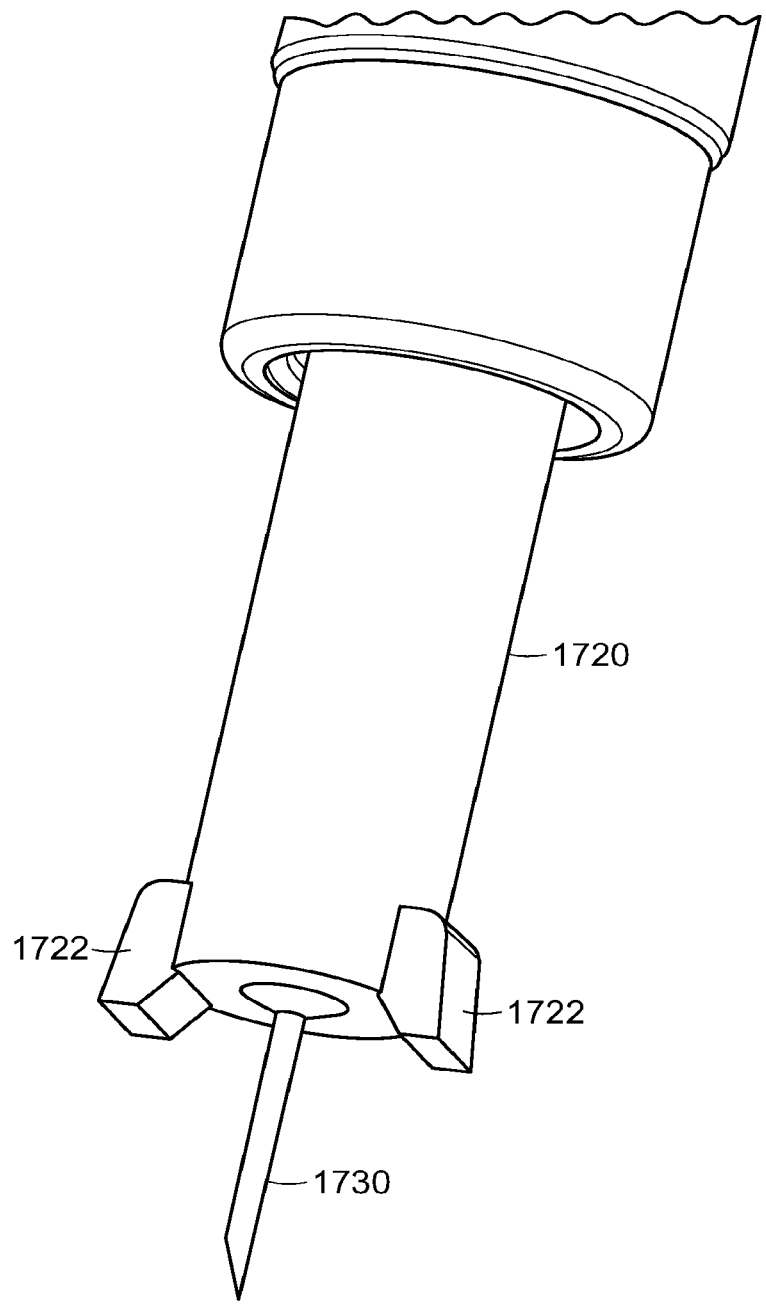
Figure 17D:
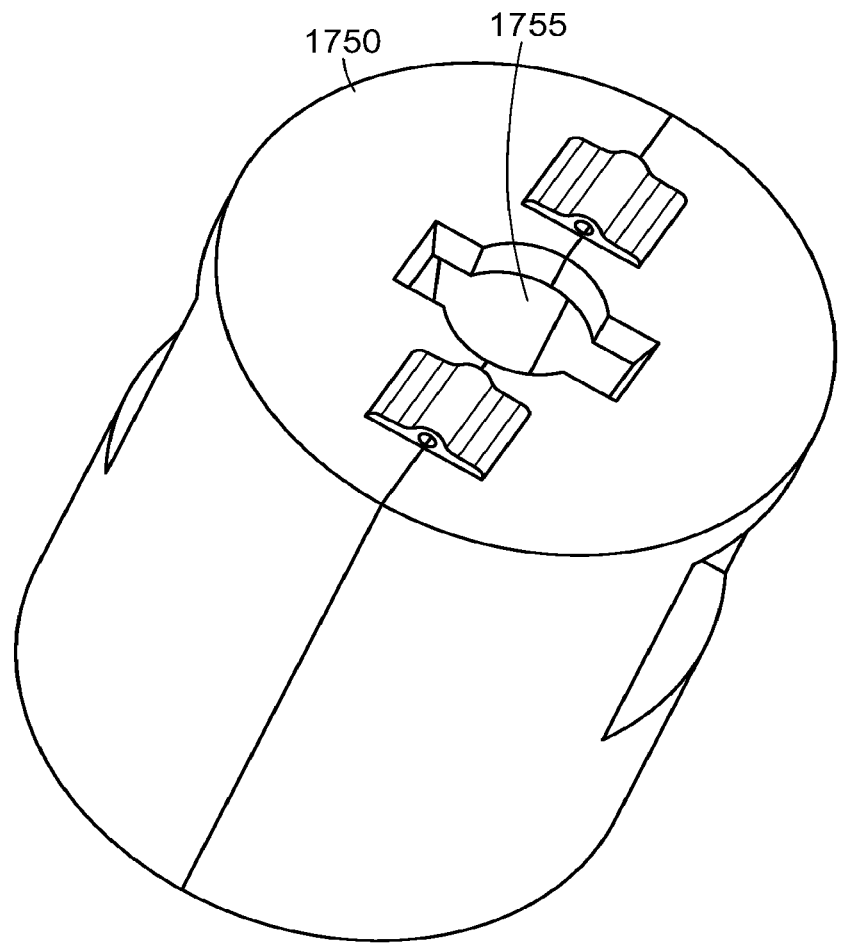
Figure 17E:
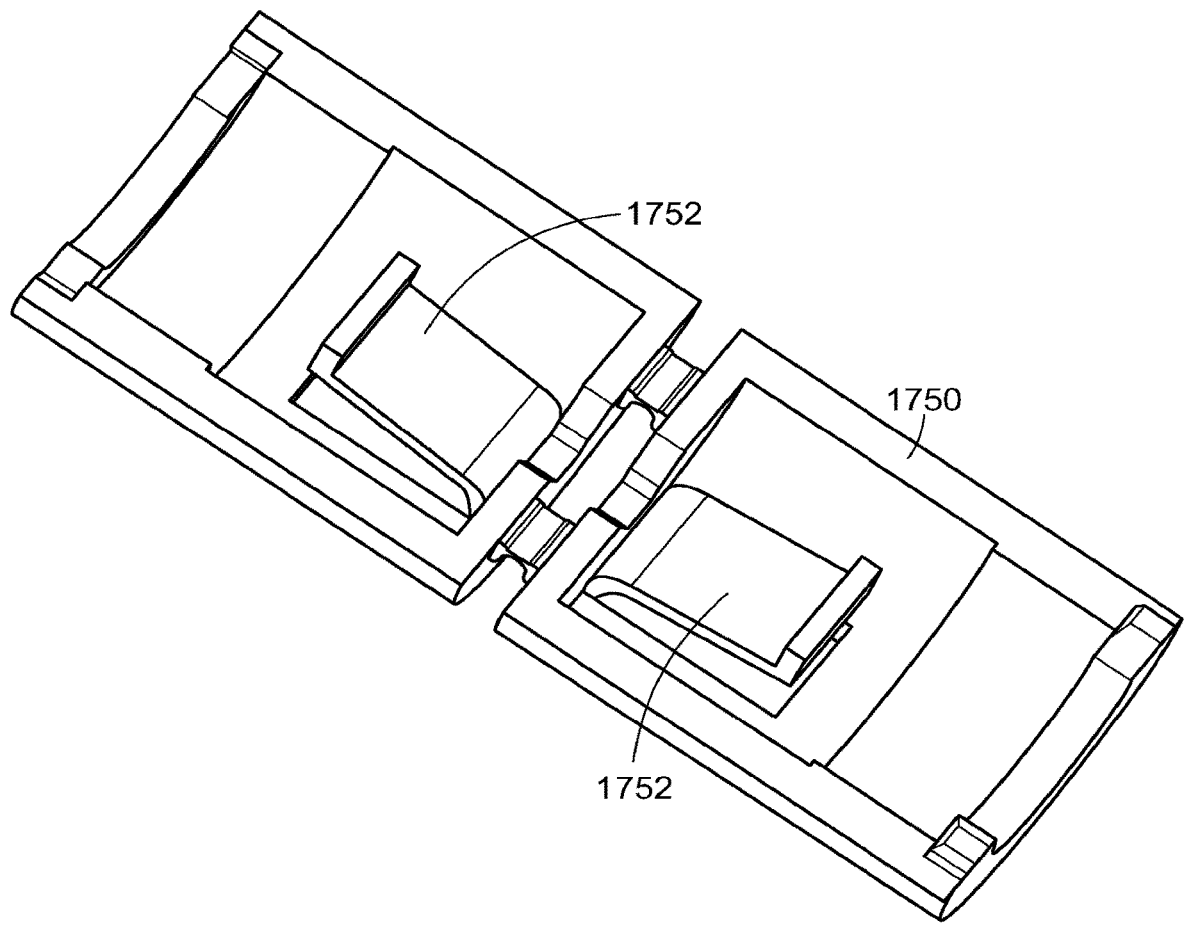
Figure 17H:
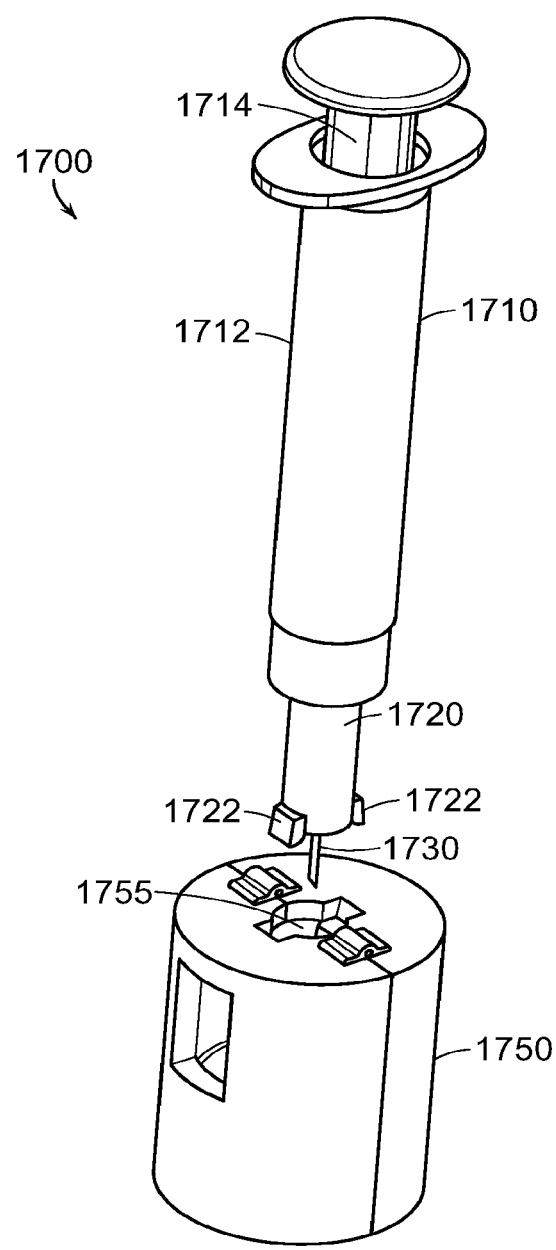

FIG. 17C shows an enlarged view of the needle hub 1720 showing two engagement or key features 1722 for making contact with the two slanted arms or doors 1752. FIG. 17D is an enlarged illustration of the cap 1750. The cap 1750 has a key feature in the form of an opening 1755 configured to accommodate entry of the needle hub 1720 including the two engagement features 1722. FIG. 17E is a perspective view of the inside of the cap 1750 as it is hinged open along one end; the figure is presented for illustrative purposes, and the cap is not required to open. FIG. 17F is a side view of the cap 1750 as it is hinged open. FIG. 17G shows a cross-sectional view taken along the line A-A in FIG. 17F. FIG. 17H illustrates a perspective view of the system 1700, showing the syringe 1710, needle hub 1720, and cap 1750.

Each arm or door 1752 may have a slanted portion 1753 and a flat portion 1754. In a resting condition, the arms or doors 1752, and more specifically the flat portions 1754 of the arms or doors 1752, block access to fill port or the opening of the liquid drug container. When the needle hub 1720 is advanced into the cap 1750 through the opening 1755, the key features 1722 engage the slanted portions 1753 of the arms or doors 1752, moving the arms or doors 1752 to the side, thus creating a gap between the arms or doors 1752 to allow the needle 1730 to pass through. The needle 1730 may then have access to the fill port or the septum of the liquid drug container or vial as it is pushed down, and the syringe 1710 may then be filled with the liquid drug from the liquid drug container or vial or may deliver the liquid drug to a medical device. When the needle 1730 is removed, the arms or doors 1752 may return to their original position, as the plastic will no longer be under stress. In some embodiments, a standard needle hub is not able to make contact with the arms or doors 1752, due to not fitting into the opening 1755 and/or not being able to open the arms or doors 1752; the septum remains covered when trying to enter the liquid drug container with a standard needle.

The system 1700 is used to make sure that only the correct drug is used. The needle hub 1720, with its key features 1722, has a cross-sectional shape and size that match the cross-sectional shape and size of the opening 1755 in the top of the cap 1750. In this way, the needle hub 1720 can enter the cap 1750. Other needle hubs that do not fit in the opening 1755 will not be able to access the liquid drug container. In addition, the key features 1722 have a shape and size that open the arms or doors 1752. Other needle hubs that cannot open the arms or doors 1752 will not be able to access the liquid drug container. A medical device, or a system or arbor for filling a medical device, may be designed so that the needle hub 1720, with its key features 1722, can mate with the medical device, or the system or arbor for filling the medical device, so that the drug from the matching capped vial can be transferred to the medical device. Other needle hubs that do not mate with the medical device, or the system or arbor for filling the medical device, will not be able to transfer drug to the medical device. In this way, the system 1700 can be used to make sure that the correct drug vial and drug are matched with the correct medical device, ensuring that the medical device is filled only with the intended drug.

Figure 18:
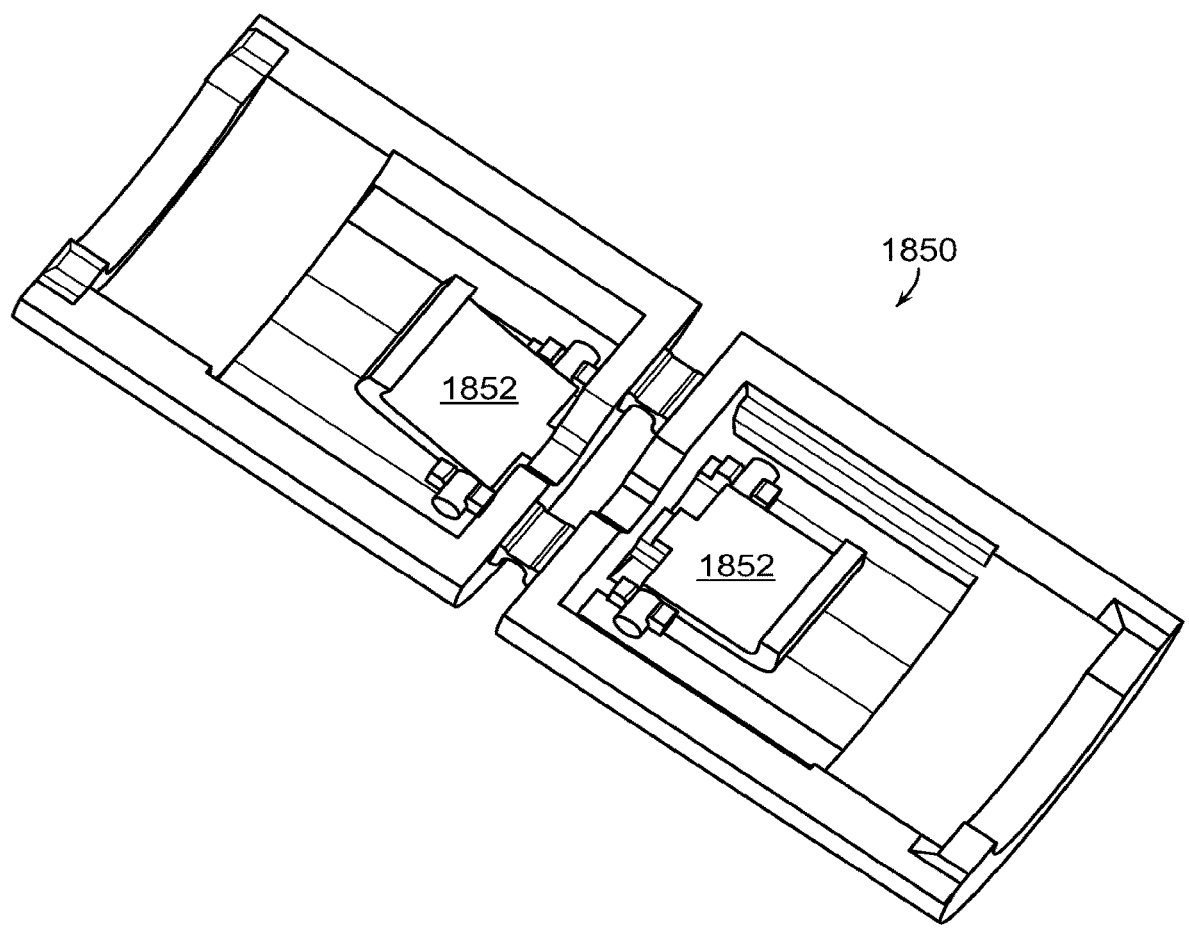
FIG. 18 shows another version of a cap similar to the cap in FIGS. 17A through 17H.

FIG. 18 illustrates another embodiment of a cap 1850 in which the slanted arms or doors 1852 are mounted on hinges. The cap 1850 operates in a similar manner to the cap 1750. When the needle hub contacts the slanted arms or doors 1852, the slanted arms or doors 1852 pivot on the hinges. The hinge(s) may be either on the side or top of the cap 1850. The cap 1850 may be molded as one or more pieces and may be made of plastic. Each arm or door 1852 may have a flat portion toward the middle of the system so that if a needle contacts the bottom of the arm or door 1852, it would not provide the sideways force necessary to push the arm or door 1852 aside. The flat bottoms may ship lap each other to ensure no opening exists above the septum.

The arms or doors 1852 may have a slant so that the needle hub would provide a sideways force to the arms or doors 1852 while moving the needle system down toward the septum. The needle hub may contact the slanted sides of the arms or doors 1852 before the needle has contacted the flat bottom of the arms or doors 1852.

Figure 19A:
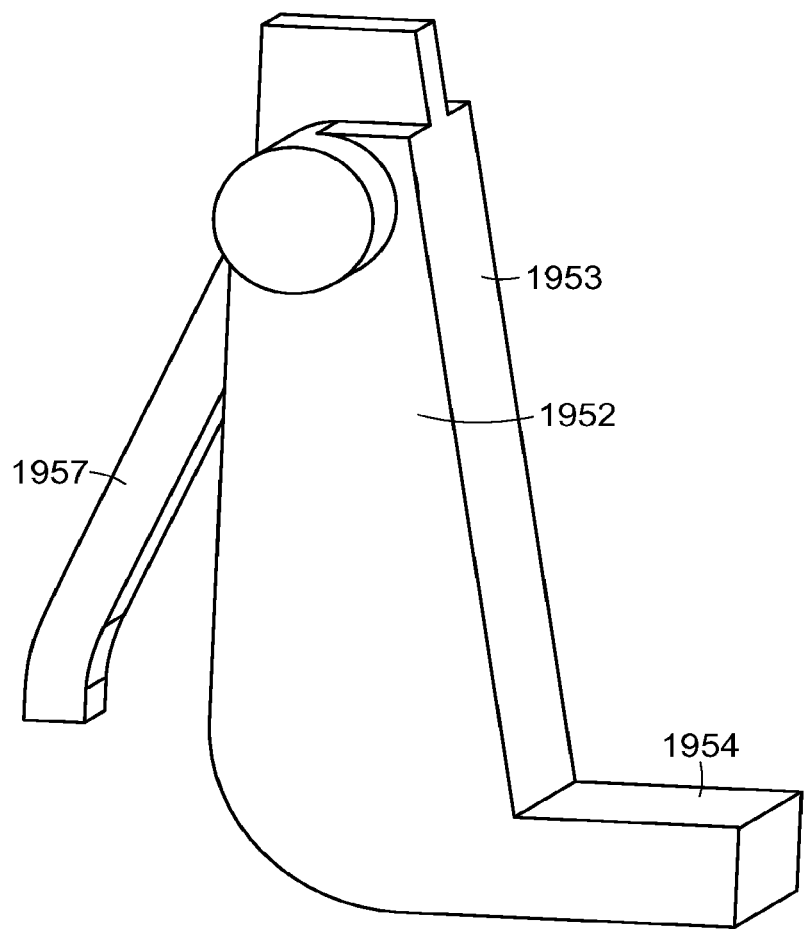
FIGS. 19A and 19B show another version of a cap similar to the cap in FIGS. 17A through 17H.
Figure 19B:
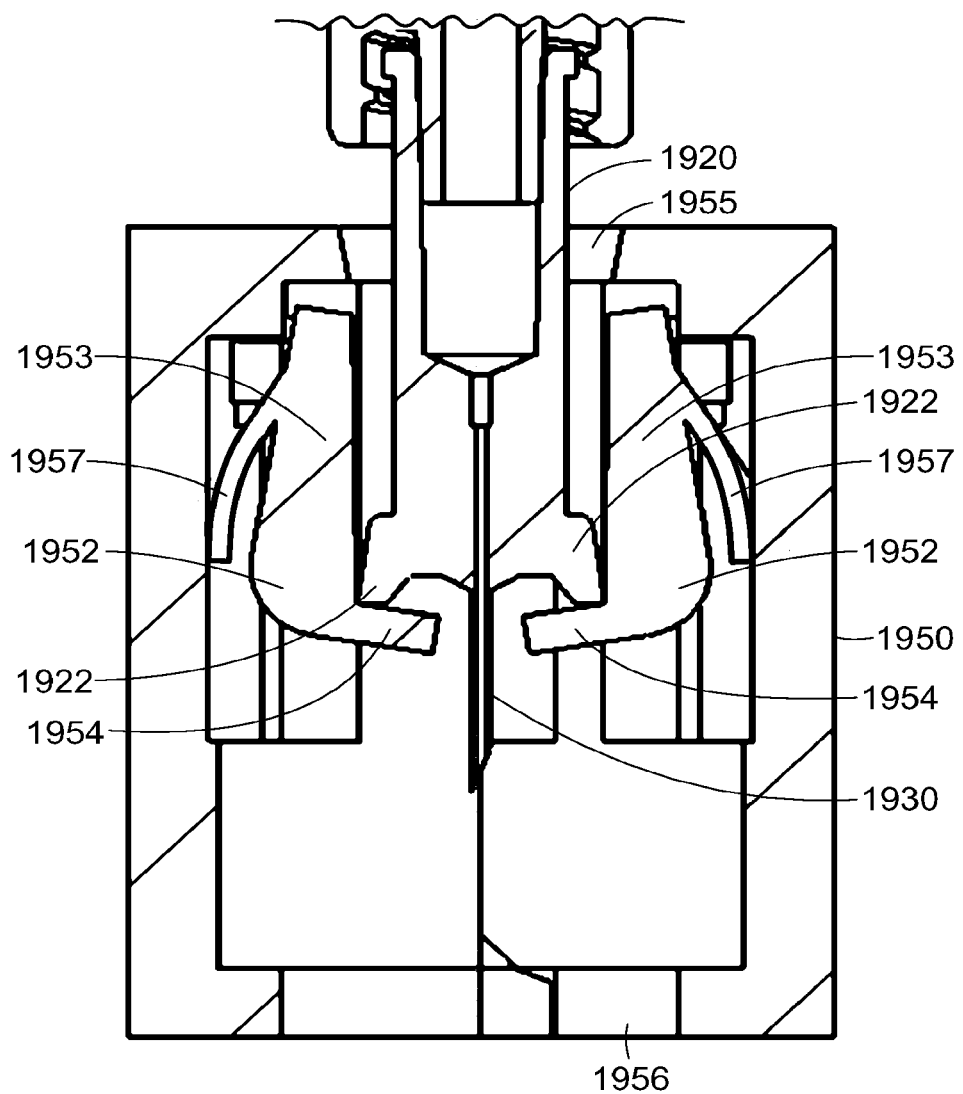

FIGS. 19A and 19B illustrate a cap 1950 similar to the cap 1750 and the cap 1850. FIG. 19A shows an arm or door 1952 having a slanted portion 1953 and a flat portion 1954 as well as a flexing element 1957. FIG. 19B shows a cross-section of the cap 1950. The cap 1950 is adapted to fit onto and attach to a liquid drug container or vial. For example, the cap 1950 has a vial opening 1956 similar to vial opening 1756.

When the needle hub 1920 is advanced into the cap 1950 through the opening 1955, the key features 1922 engage the slanted portions 1953 of the arms or doors 1952, moving the arms or doors 1952 to the side, thus creating a gap between the arms or doors 1952 to allow the needle 1930 to pass through. When the arms or doors 1952 are pressed open, the flexing elements 1957 flex against the inner wall of the cap 1950. When the needle 1730 is removed, the arms or doors 1952 may return to their original position, as the flexing elements 1957 force the arms or doors 1952 to close.

Figure 20A:
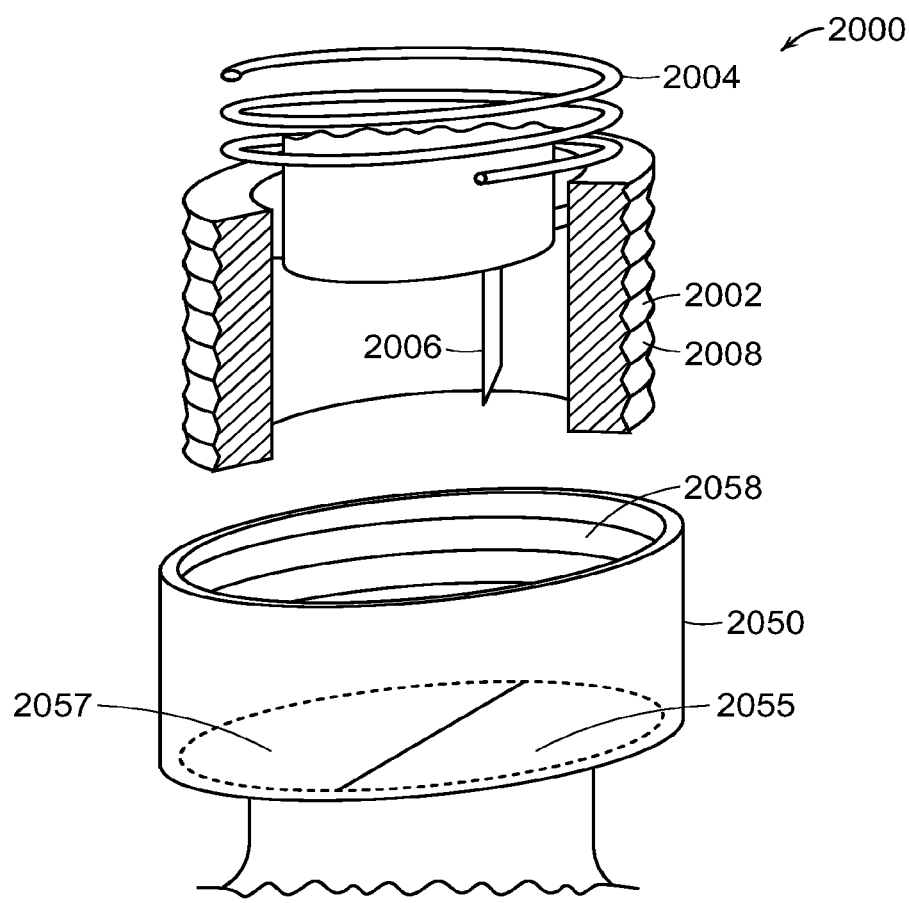
FIGS. 20A through 20C show a system comprising a needle hub and container or vial adapter or cap in accordance with another embodiment.
Figure 20B:
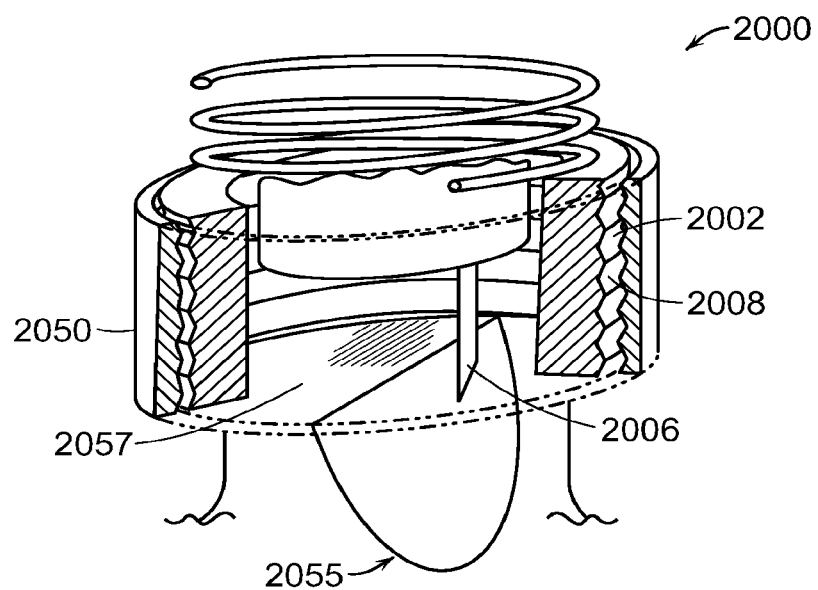
Figure 20C:
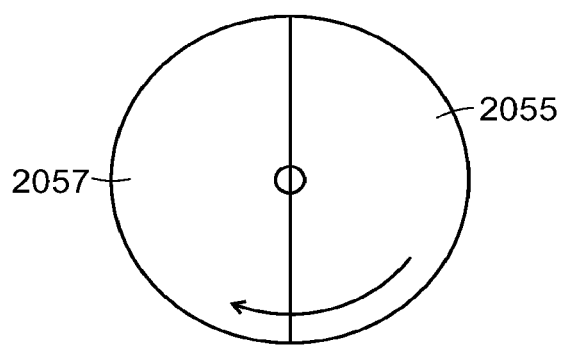

FIGS. 20A through 20C illustrate another embodiment. The system 2000 includes a threaded needle cover 2002 that is biased toward the distal end by a spring 2004 to cover a needle 2006. The needle cover 2002 is a threaded open cylinder. Thus, the needle hub includes a needle 2006 (which may be off-center) that is fully enclosed by the threaded open cylinder serving as needle cover 2002. At the base of the threaded open cylinder or needle cover 2002 is the small spring 2004. A cap 2050 may be attached to a vial or other liquid drug container that may be filled with fluid; the cap 2050 features threads 2058 that mate with the threads 2008 of needle cover 2002 of the needle hub. The cap 2050 covers a septum on the container that may be penetrated by the needle 2006 to inject or remove fluid. Once the threaded open cylinder or needle cover 2002 on the needle hub and cap 2050 are mated, the door or cap cover 2055 is moved out of the way, allowing the needle 2006 to be pushed into the septum to either inject or remove fluid from the container. As the needle hub is unmated with the cap 2050, the cap cover 2055 covers the membrane once again; this re-covering may be assisted by a spring inside the cap.

The needle 2006 may be sub-flush of the threaded open cylinder or needle cover 2002; the spring mentioned above may be used to allow the needle 2002 to be pushed down into the septum once the threads are fully engaged. When the needle hub is fully threaded into the cap 2050, it may rotate the door or cap cover 2055 in the cap 2050 to allow access to the septum. The door or cap cover 2055 may be semi-circular, and the cap 2056 may contain a fixed semicircular piece 2057 opposite the door or cap cover 2055 in the closed position and which may align with the door or cap cover 2055 when opened to create a semicircular pass through. The door or cap cover 2055 may either be spring loaded or could close by other means when the needle hub is unscrewed. FIG. 20C shows a top view of the door or cap cover 2055 and the fixed semicircular piece 2057.

In some embodiments, as shown in FIGS. 21A through 21H, a system 2100 includes a medical device 2130 with a medical device cap 2132 having a keyed alignment device 2134, a liquid drug container 2150 with a keyed cap 2152, and a syringe 2110 with a keyed connector 2112. In some embodiments, the keyed components 2134, 2152, 2112 are unique to a particular medication, type of medication, dosage of medication, strength of medication, or any other classification of medication. The keyed components 2152, 2134 on the liquid drug container (e.g., vial) and medical device may be the same type and feature the ability to mate with the same syringe keyed component 2112. The syringe 2110 includes a keyed connector 2112 that mates with one or both of the keyed components 2134, 2152 of the medical device and liquid drug container.

Figure 21A:
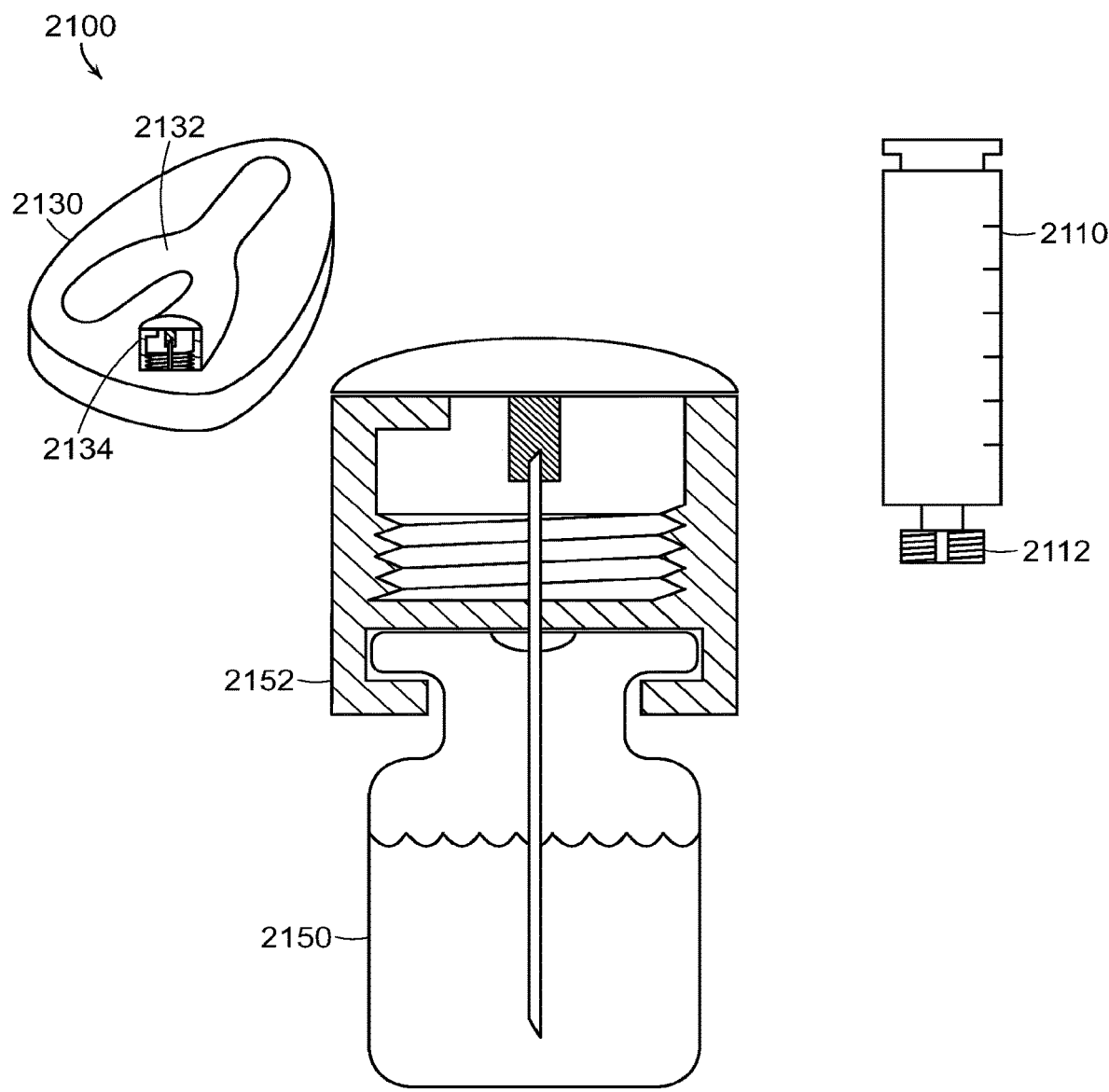
FIGS. 21A through 21F show a system comprising a needle hub, container or vial adapter or cap, and medical device in accordance with another embodiment.
Figure 21B:
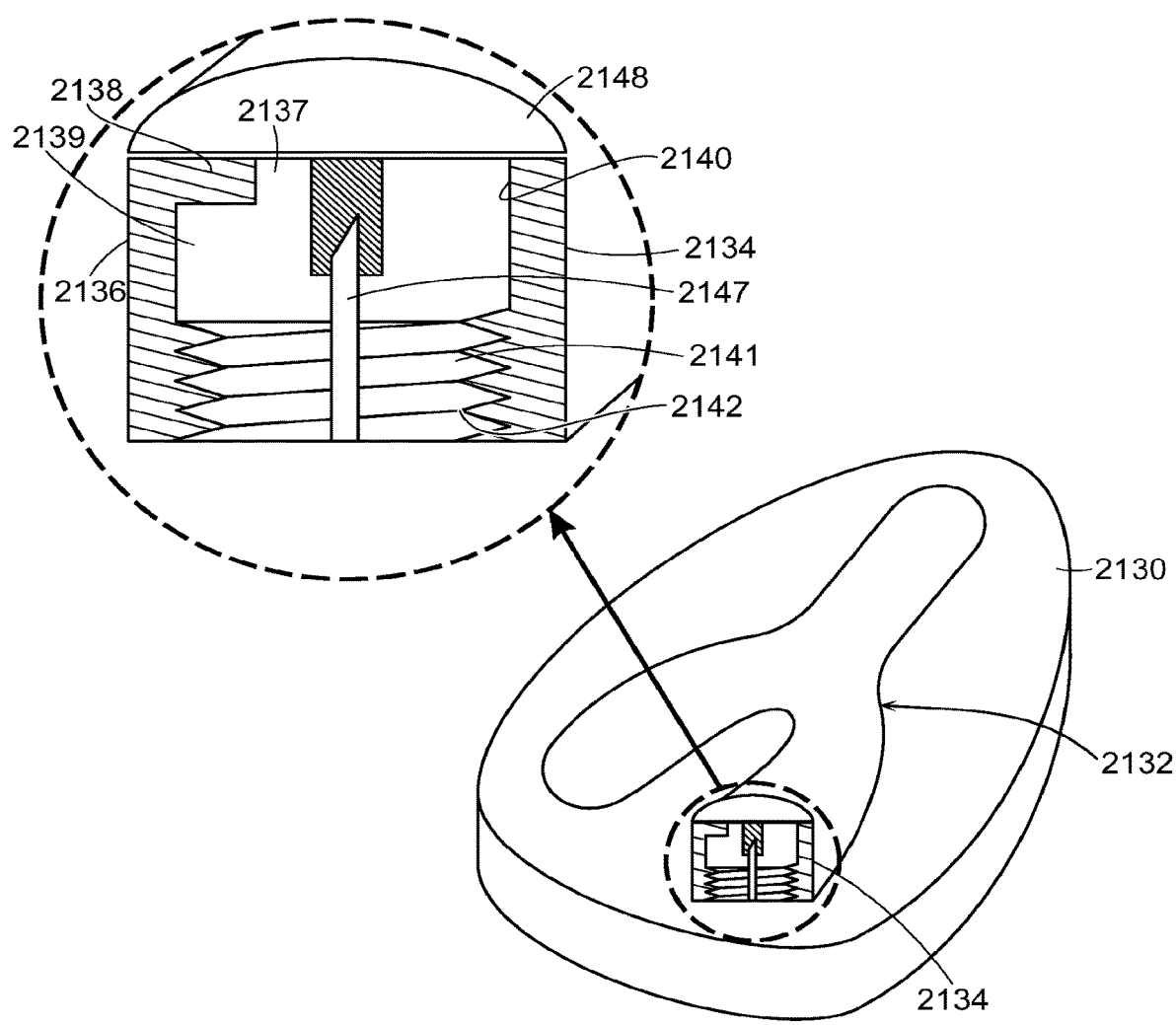

FIG. 21B illustrates an exemplary medical device 2130 in accordance with embodiments disclosed herein. The medical device 2130 may be similar to other medical devices described above. A drug delivery device or medical device cap 2132 may be disposed on a surface of the medical device 2130 and may allow a person to fill (including refill) a medication reservoir housed by the medical device 2130. The medical device cap 2132 has a keyed alignment device 2134. A removable cap 2148 may be used to seal the keyed alignment device 2134 of the medical device cap 2132 when it is not in use. The removable cap 2148 may be removed to reveal a female keyed threaded connection 2136 and a needle 2147, which may extend into a fill port of the medical device 2130. The removable cap 2148 may include septum material 2149 that covers the exposed end of the needle 2147 when the removable cap 2148 is in place, thereby keeping the needle 2147 plugged. The drug delivery device or medical device cap 2132 may be configured to attach to a medical device 2130 already designed and manufactured to use a standard fill port (i.e., the drug delivery device or medical device cap 2132 may be retro-fitted onto existing medical devices 2130); in other embodiments, the cap 2132, needle 2147, and connection 2136 may be integrated into the medical device 2130 (i.e., the functionality of the drug delivery device or medical device cap 2132 may be integrated into the medical device 2130). The embodiment is not limited to any particular configuration for the cap 2132, needle 2147, and connection 2136.

Figure 21C:
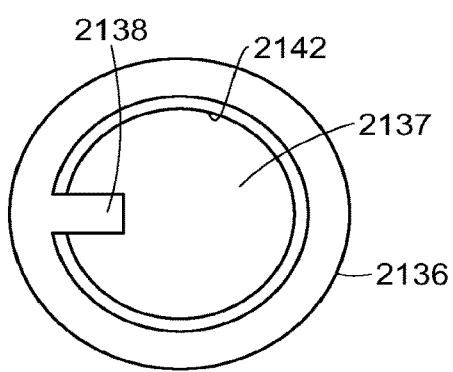

The keyed alignment device 2134 includes the female keyed threaded connection 2136, which has an opening 2137, a keying feature 2138, a first non-threaded section 2139 with a non-threaded wall 2140, and a second threaded section 2141 with an internal thread 2142. FIG. 21C shows a top view of the female keyed threaded connection 2136, showing the opening 2137, the keying feature 2138, and the internal thread 2142.

Figure 21D:
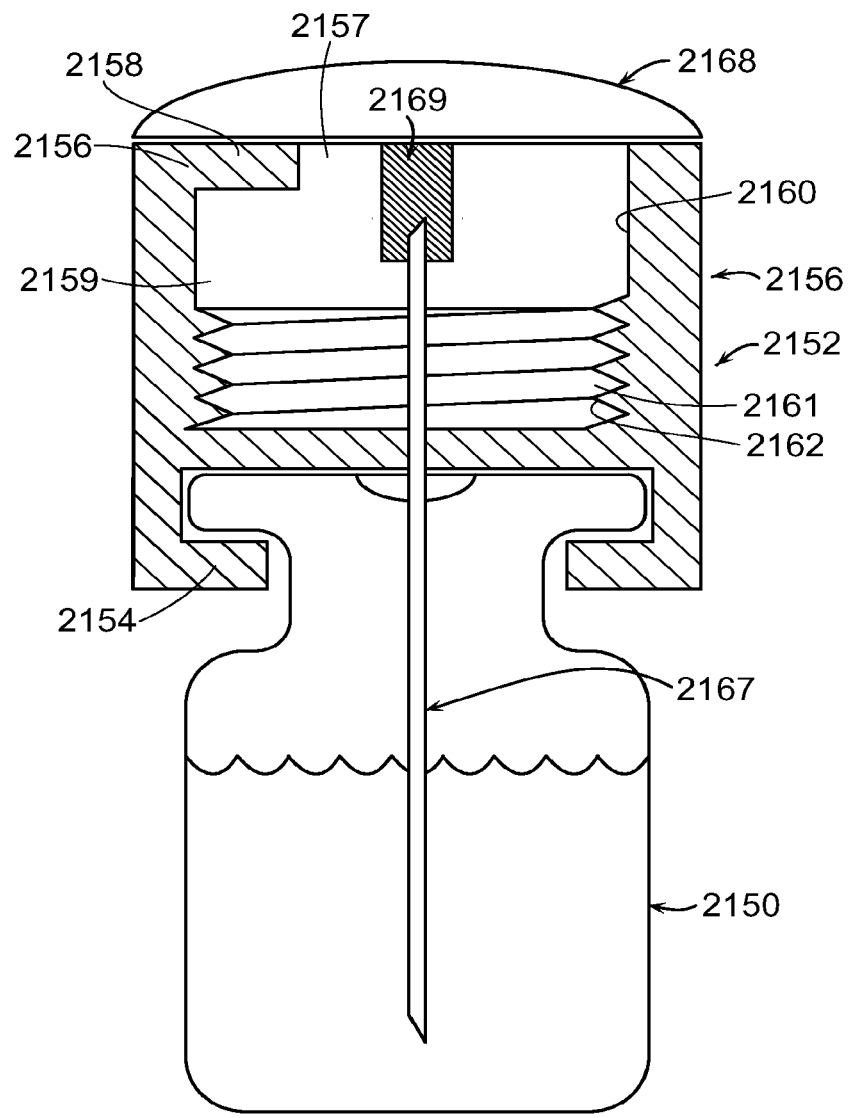

FIG. 21D illustrates a liquid drug container 2150 (here, a vial) in accordance with the embodiment of system 2100. A keyed cap 2152 is attached to the container or vial using any suitable method or system; for example, a flexible latch 2154 may be used to attach the keyed cap 2152 to the container or vial 2150. In other embodiments, the keyed cap 2152 is integrated into the container or vial. The keyed vial cap 2152 further includes a female keyed threaded connection 2156. A needle 2167 extends from the medication in the vial 2150 to an opening inside of the keyed vial cap 2152. When a syringe 2110 is threaded/mated with the female keyed threaded connection 2156, the needle 2167 may pierce a septum on the syringe 2110 and allow the syringe 2110 to transfer the medication from the vial 2150 to the syringe 2110. When the keyed vial cap 2152 is not in use, a removeable cap 2168 may be mated with the female keyed threaded connection 2156 to protect the needle 2167, keyed vial cap 2152, and the rest of the container 2150 from contamination, spillage, etc. The removeable cap 2168 may include septum material 2169 to keep the needle 2167 plugged when not in use.

The keyed cap 2152 includes the female keyed threaded connection 2156, which has an opening 2157, a keying feature 2158, a first non-threaded section 2159 with a non-threaded wall 2160, and a second threaded section 2161 with an internal thread 2162. A top view of the female keyed threaded connection 2156 looks similar to the top view of the female keyed threaded connection 2136 shown in FIG. 21C.

Figure 21E:
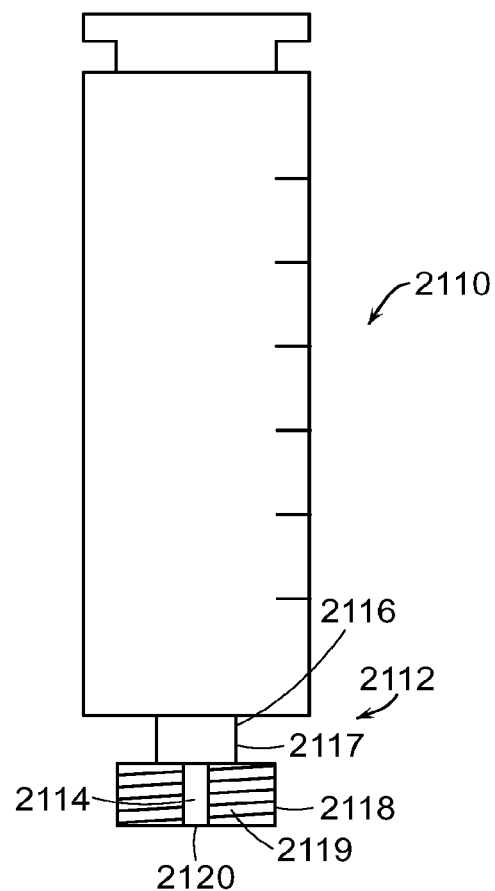

FIG. 21E illustrates a syringe 2110 in accordance with the system 2100. The syringe 2110 includes a male keyed threaded connection 2112 (either integrated therewith or disposed on a hub or an adaptor attached to the syringe 2110) that may mate with the female keyed threaded connections 2136, 2156 described above. The syringe 2110 may be needleless; the needles used to transfer medication with the medical device 2130 and container 2150 may be contained in or attached to those devices instead of the syringe 2110. A septum 2120 may be used to prevent contamination of the syringe 2110 and to prevent any medication therein from leaking out. In an alternative, a needle may be attached to the syringe 2110, and the needles associates with the medical device 2130 and container 2150 may be omitted.

Figure 21F:
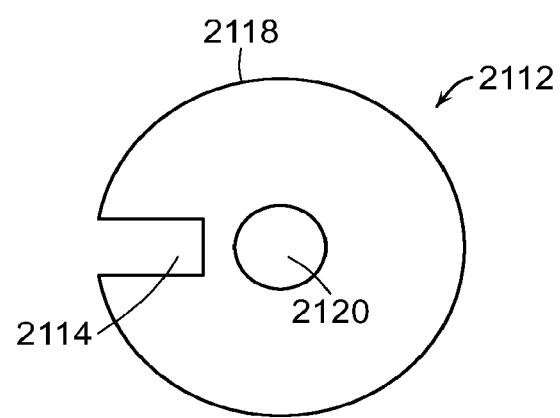

The male keyed threaded connection 2112 has a first non-threaded section 2116 with a non-threaded wall 2117, and a second threaded section 2118 with an external thread 2119. An end view of the male keyed threaded connection 2112 is shown in FIG. 21F. As can be seen, the second section 2118 has a slot forming a keying feature 2114. The keying feature may be any feature, key, notch, cut-away, etc., that mates and matches with a corresponding feature on either or both of the female keyed threaded connections 2136, 2156 mentioned above. As an example, the female keyed threaded connection may include a raised ridge that spirals down through it; a connector that does not include the matching key is not able to be threaded into the female keyed threaded connection.

In the example of system 2100, the keyed threaded connection 2112 mates with the keyed threaded connections 2156, 2136 of the cap and medical device. To withdraw drug from the container 2150 into the syringe 2110, the keyed threaded connection 2112 is inserted into the opening 2157 of the keyed threaded connection 2156, with the keying feature 2114 aligned with the keying feature 2158. The keying feature 2158 fits into the keying feature 2114. Once the second section 2118 is advanced axially without rotation into the first non-threaded section 2159 and past the keying feature 2158, it may then be turned. At this point, the first section 2116 which has a narrower diameter is aligned with the keying feature 2158, so that first section 2116 can be rotated in the cap 2152 without interference from the keying feature 2158. The threaded second section 2118 can be rotated to mate with the thread 2162 of the second threaded section 2161 of the cap 2152. Once the keyed threaded connector 2112 is fully threaded and seated within the keyed threaded connector 2156, the drug may be withdrawn into the syringe 2110. The syringe 2110 may then be removed by rotation in an opposite direction and then axial translation from the cap 2152, with the keying feature 2114 again aligned with the keying feature 2158.

The syringe 2110 may access the medical device 2130 for filling it in a similar manner. The keyed threaded connection 2112 is inserted into the opening 2137 of the keyed threaded connection 2136, with the keying feature 2114 aligned with the keying feature 2138. Once the second section 2118 is advanced axially without rotation into the first non-threaded section 2139 and past the keying feature 2138, it may then be turned. At this point, the first section 2116 which has a narrower diameter is aligned with the keying feature 2138, so that first section 2116 can be rotated without interference from the keying feature 2138. The threaded second section 2118 can be rotated to mate with the thread 2142 of the second threaded section 2141 of the keyed threaded connection 2136. Once the keyed threaded connection 2112 is fully threaded and seated within the keyed threaded connection 2136, the drug may be transferred into the medical device 2130. The syringe 2110 may then be removed by rotation in an opposite direction and then axial translation from the keyed alignment device 2134, with the keying feature 2114 again aligned with the keying feature 2138.

Figure 22A:
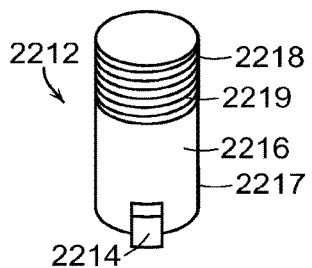
FIGS. 22A through 22J show another embodiment of an engagement mechanism for a needle hub, container or vial adapter or cap, and medical device.
Figure 22B:
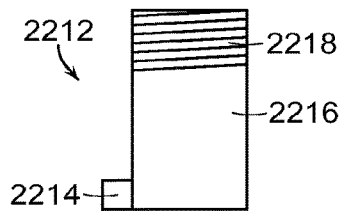
Figure 22C:
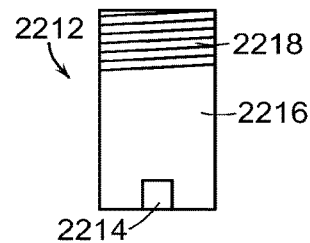

FIGS. 22A through 22J show an alternative embodiment of the keyed threaded connections for the system 2100. FIGS. 22A through 22C show a perspective view and two side views of the male keyed threaded connection 2212 (for the syringe). The male keyed threaded connection 2212 has a first non-threaded section 2216 with a non-threaded wall 2217, and a second threaded section 2218 with an external thread 2219. The distal end of the keyed threaded connection 2212 has a keying feature 2214 in the form of a projection.

Figure 22D:
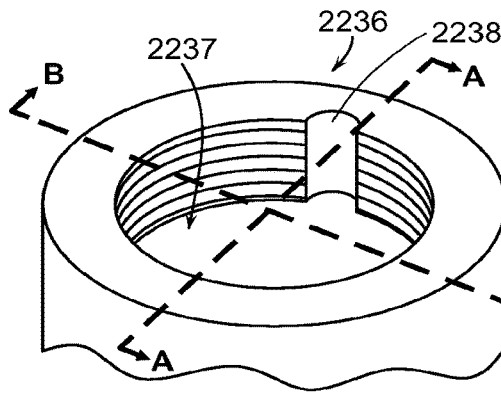
Figure 22E:
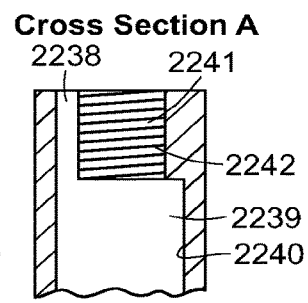
Figure 22F:
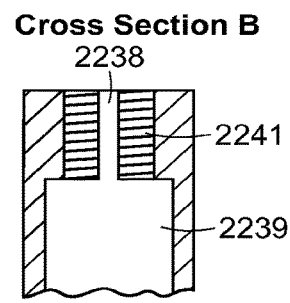

FIG. 22D shows a perspective view of the female keyed threaded connection 2236 (for the medical device and the liquid drug container). FIG. 22E shows a cross-sectional view corresponding to the line A-A in FIG. 22D. FIG. 22F shows a cross-sectional view corresponding to the line B-B in FIG. 22D. The female keyed threaded connection 2236 has an opening 2237, a keying feature 2238 in the form of a slot, a first non-threaded section 2239 with a non-threaded wall 2240, and a second threaded section 2241 with an internal thread 2242.

Figures 22G, 22H, 22I, 22J:
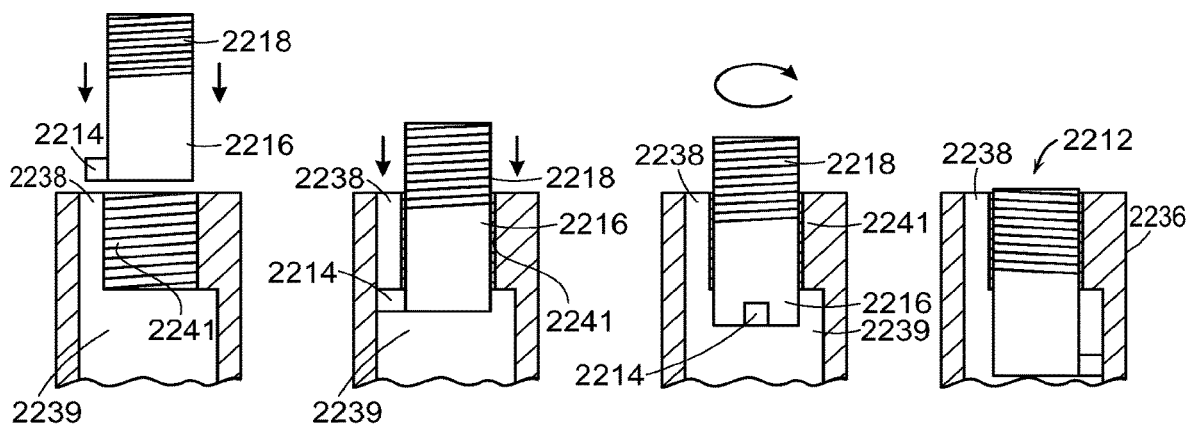

FIGS. 22G through 22J shows steps in connecting the syringe to the medical device or cap for the liquid drug container, with views corresponding to the cross-section of FIG. 22E. As shown in FIG. 22G, the keyed threaded connection 2212 is inserted into the opening 2237 of the keyed threaded connection 2236, with the keying feature 2214 aligned with the keying feature 2238. The keying feature 2214 fits into the keying feature 2238. FIG. 22H shows the keying feature 2214 advanced axially without rotation into the first non-threaded section 2139, which is wider than the threads of the threaded second section 2241. The keyed threaded connection 2212 may then be turned. As shown in FIG. 22I, the keyed threaded connection 2212 can be rotated without interference from the keying feature 2214. The threaded second section 2218 can be rotated to mate with the thread 2242 of the second threaded section 2241 of the keyed threaded connection 2236. Once fully threaded and seated, as shown in FIG. 22J, the drug may be transferred into the syringe from the container or vial or into the medical device from the syringe. The syringe may then be removed by rotation in an opposite direction and then axial translation, withdrawing the keying feature 2214 back through the keying feature 2238.

Figure 23A:
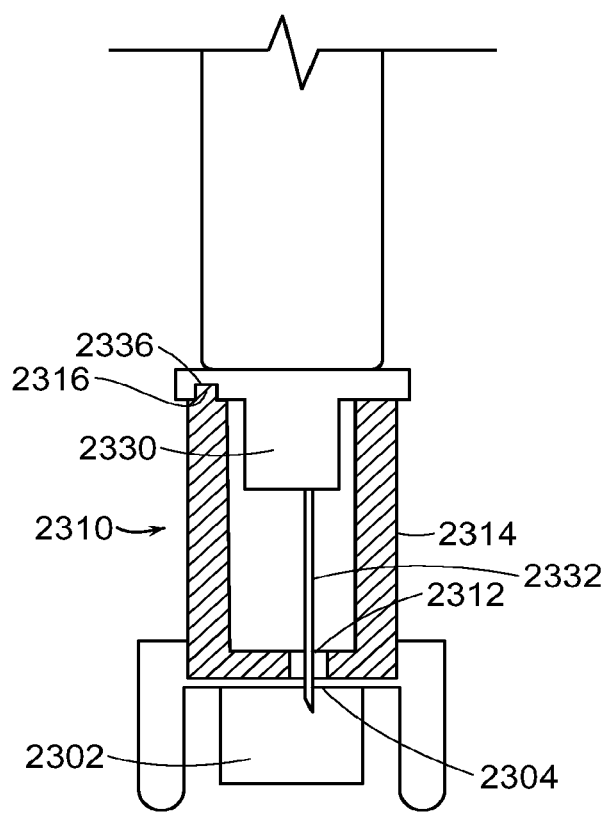
FIGS. 23A and 23B illustrate a system comprising a needle hub and cap in accordance with another embodiment.
Figure 23B:
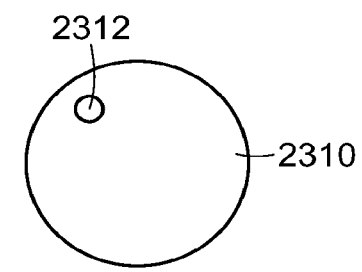

FIGS. 23A and 23B illustrate cross-sectional and top views of an attachment or cap 2310 configured to be fitted onto a medical device or a container 2302 (e.g., a vial) holding a liquid medication in which the cap 2310 covers the vial's septum 2304 or the container or vial or medical device entryway except for a hole 2312 that is off-axis from the center of the container/septum. The cap 2312 includes a side wall 2314 through which a needle hub 2330 must go in order for the needle 2332 to reach the septum. The top of the cap 2310 has a keying projection 2316 that has a geometry (size and shape) that mates with the geometry of a corresponding keying recess 2336 in the needle hub both to align the needle 2332 with the hole 2312 and to prevent a different type of needle from being used. The keying projection 2316, which may be on the cap or on the needle hub, has a height to prevent the needle from accessing the container or vial unless a matching syringe is used with the cap. The hole 2312 in the cap 2310 may also have a cover which is pushed out of the way when the needle hub is inserted. A medical device may be fitted with similar geometry as the vial cap to match with the same needle hub 2330.

Figure 24A:
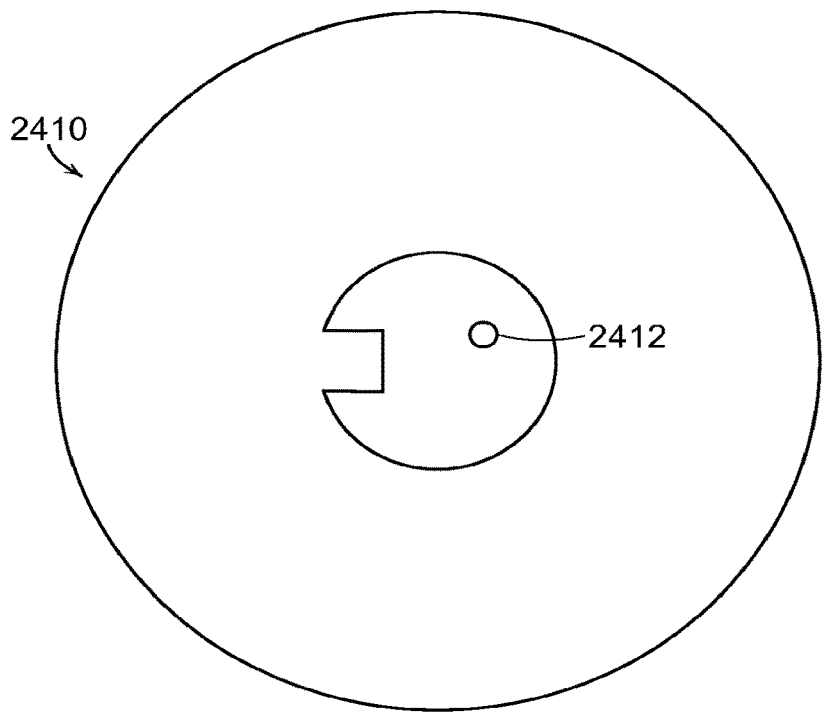
FIGS. 24A through 24D illustrate another system comprising a needle hub and cap in accordance with another embodiment.
Figure 24B:
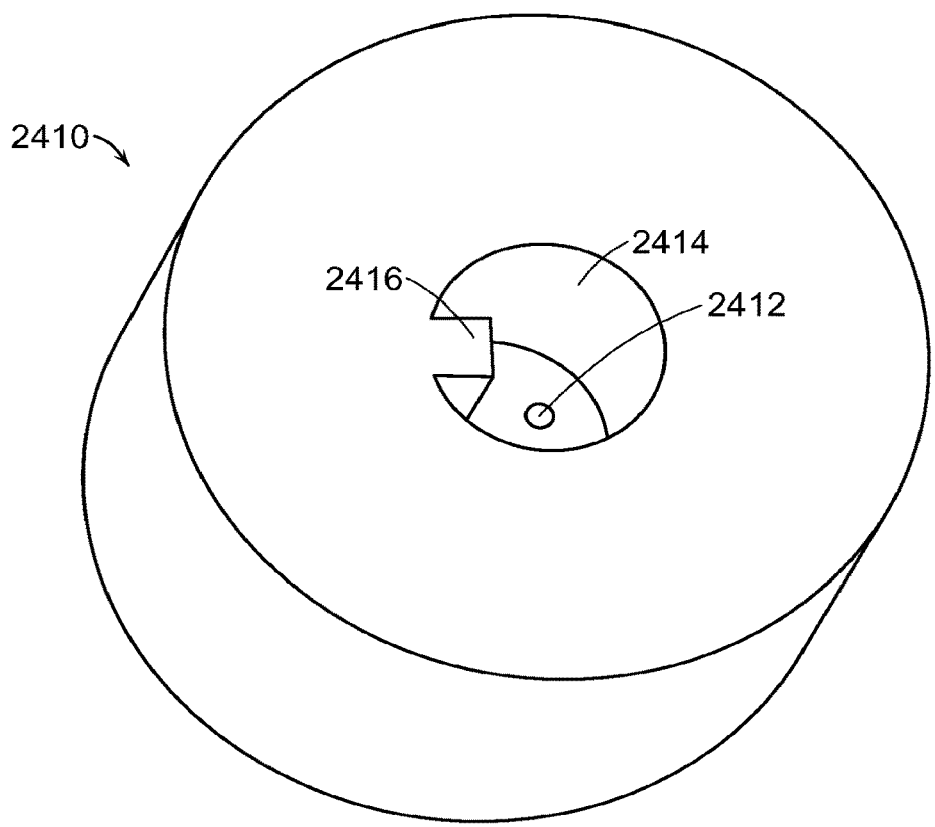
Figure 24C:
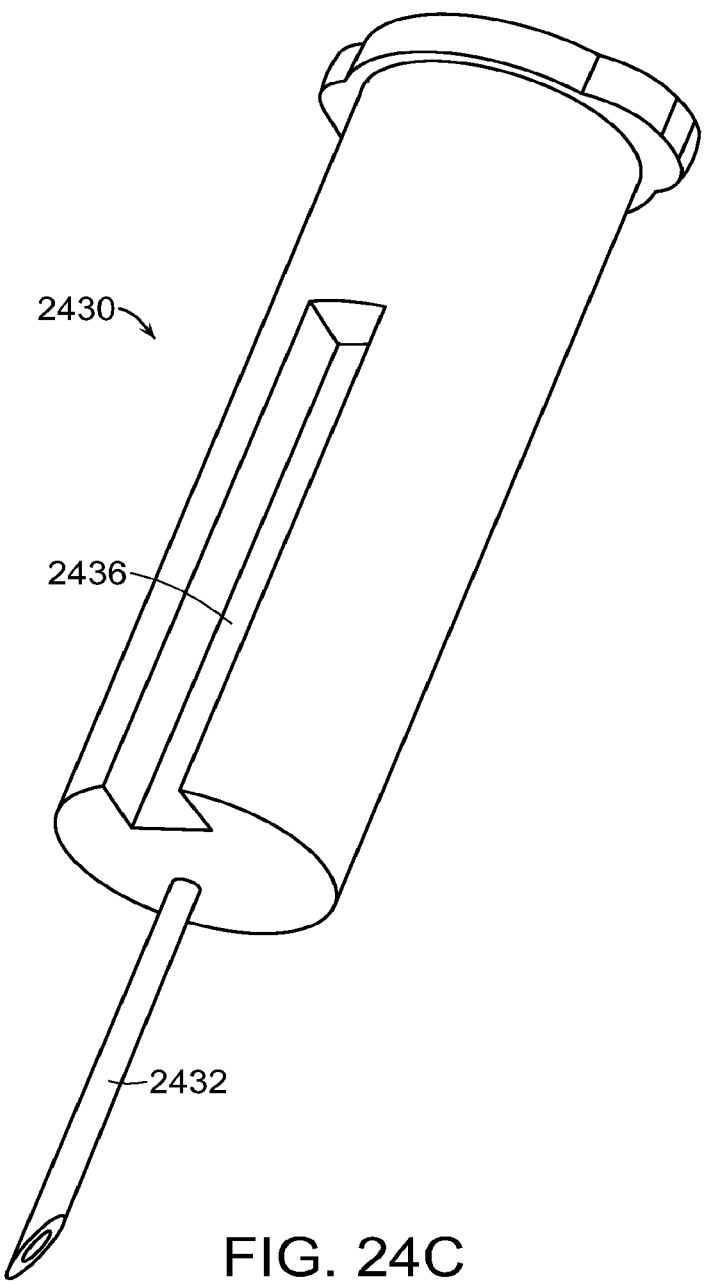
Figure 24D:
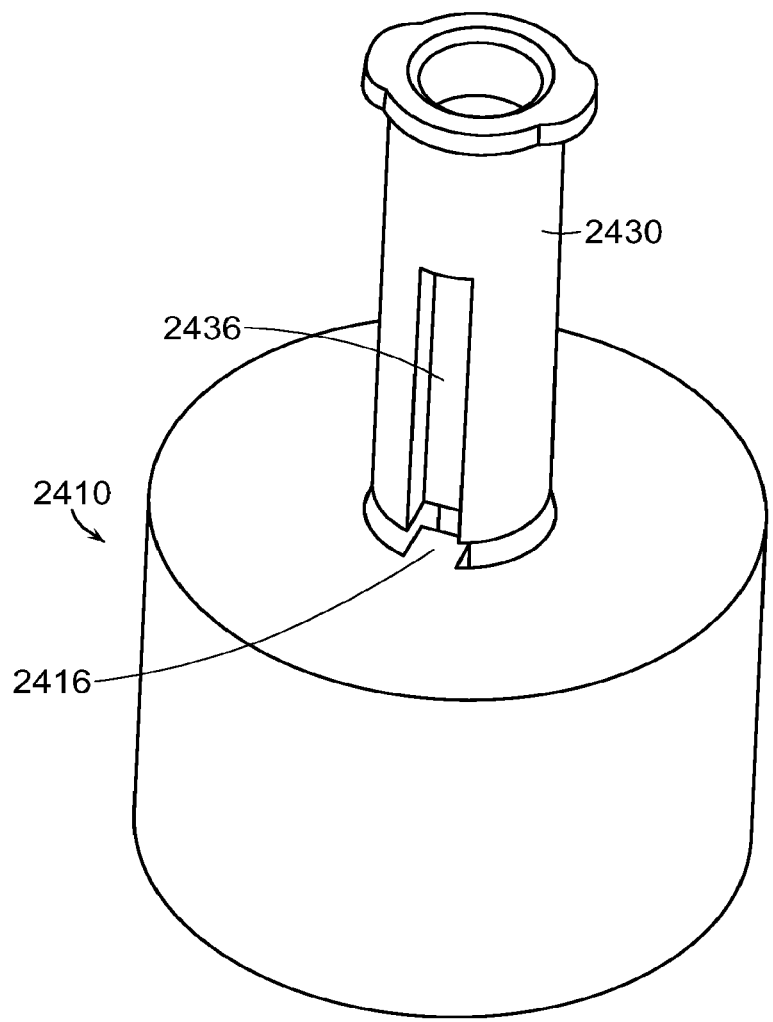

FIGS. 24A through 24D illustrate another embodiment. FIGS. 24A and 24B show top and perspective views of a keying connection 2410 that can be fitted onto or be a part of a container or vial or medical device. The keying connection can be a cap. A needle hole 2412 in the cap or keying connection 2410 is off-axis from the center of the cap or keying connection 2410, and the geometry of the side wall 2414 includes a keying protrusion or projection 2416. FIG. 24C shows a perspective view of a needle hub 2430 to mate with the keying connection or cap 2410. To mate with the keying connection or cap 2410, the needle hub 2430 includes an off-axis needle 2432 to match the off-axis needle hole 2412 and keying notch or recess 2436 to match the keying protrusion or projection 2416. A needle hub lacking either the correct keying geometry or the needle at the correct off-axis position would not be able to extract medication through a septum on the other side of the needle hole or transfer medication to a medical device with the keying connection 2410. FIG. 24D shows the needle hub 2430 aligned with the keying connection or cap 2410.

Figure 25A:
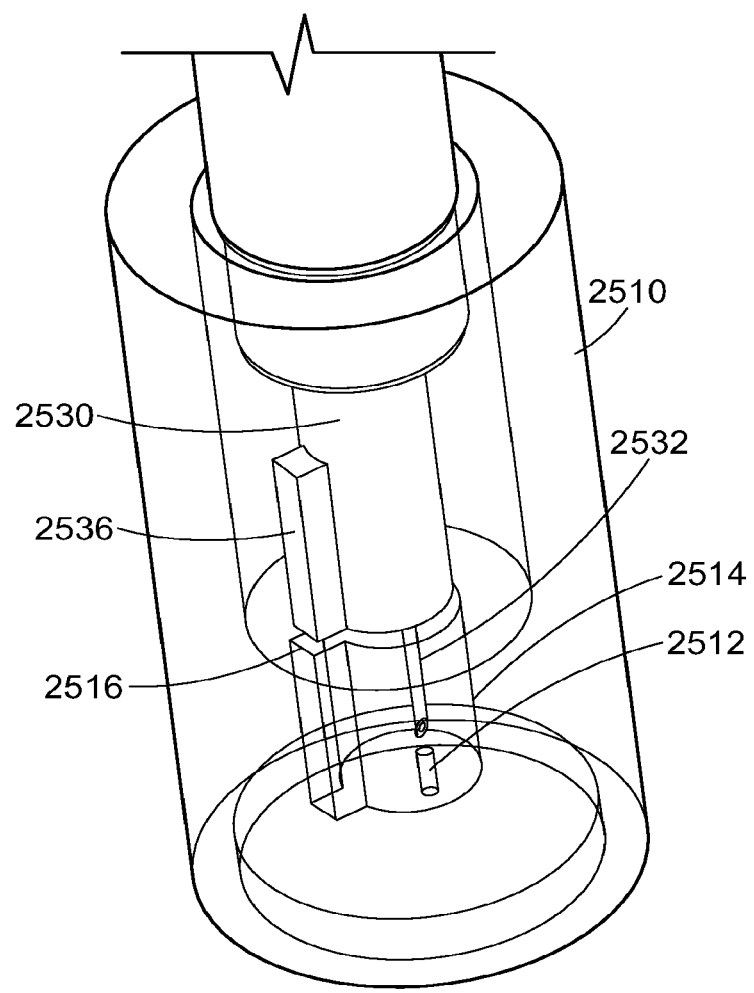
FIGS. 25A and 25B illustrate another system comprising a needle hub and cap in accordance with another embodiment.
Figure 25B:
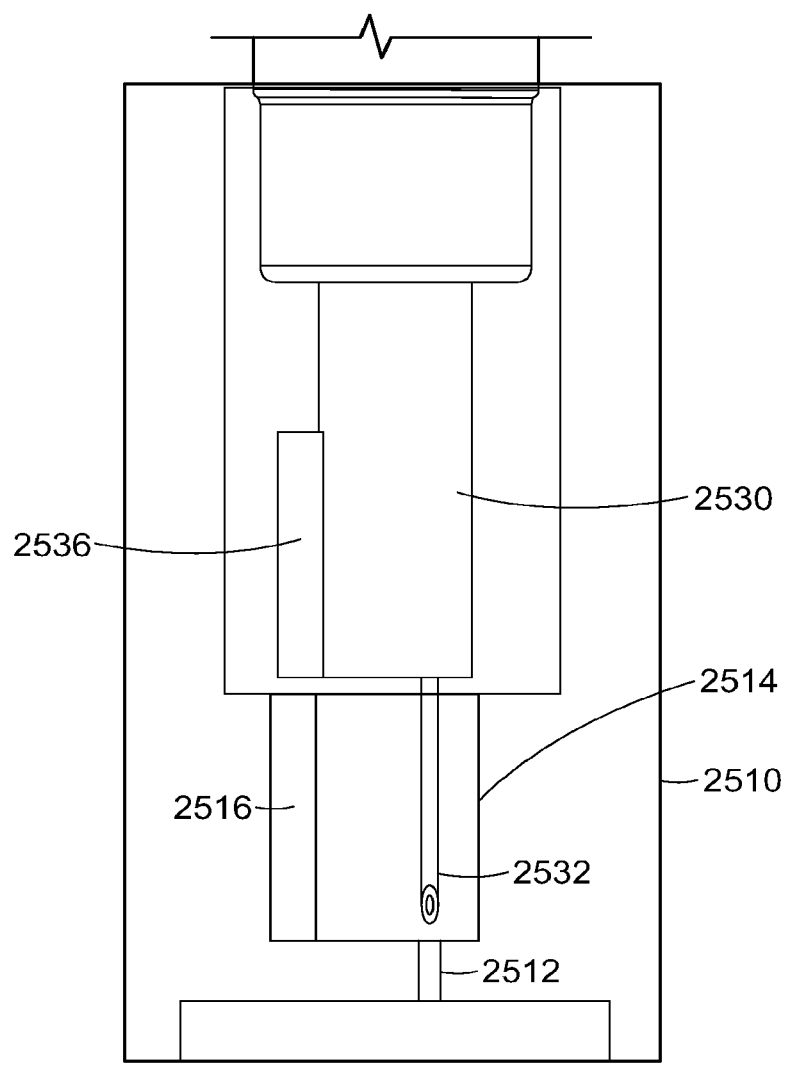

FIGS. 25A and 25B illustrate three-dimensional and side views, respectively, of a needle hub 2530 mated with a keying connection or cap 2510, the cap 2510 being shown semi-transparently to show the needle hub 2530. The keying connection 2510 can be fitted onto or be a part of a container or vial or medical device. A needle hole 2512 in the cap or keying connection 2510 is off-axis from the center of the cap or keying connection 2510, and the geometry of the side wall 2514 includes a keying feature 2516 in the form of a slot or recess. To mate with the keying connection or cap 2510, the needle hub 2530 includes an off-axis needle 2532 to match the off-axis needle hole 2512 and a keying feature 2536 in the form of a projection, protrusion, or ridge to match the keying feature 2516. A needle hub lacking either the correct keying geometry or the needle at the correct off-axis position would not be able to extract medication through a septum on the other side of the needle hole or transfer medication to a medical device with the keying connection 2510.

Figure 26:
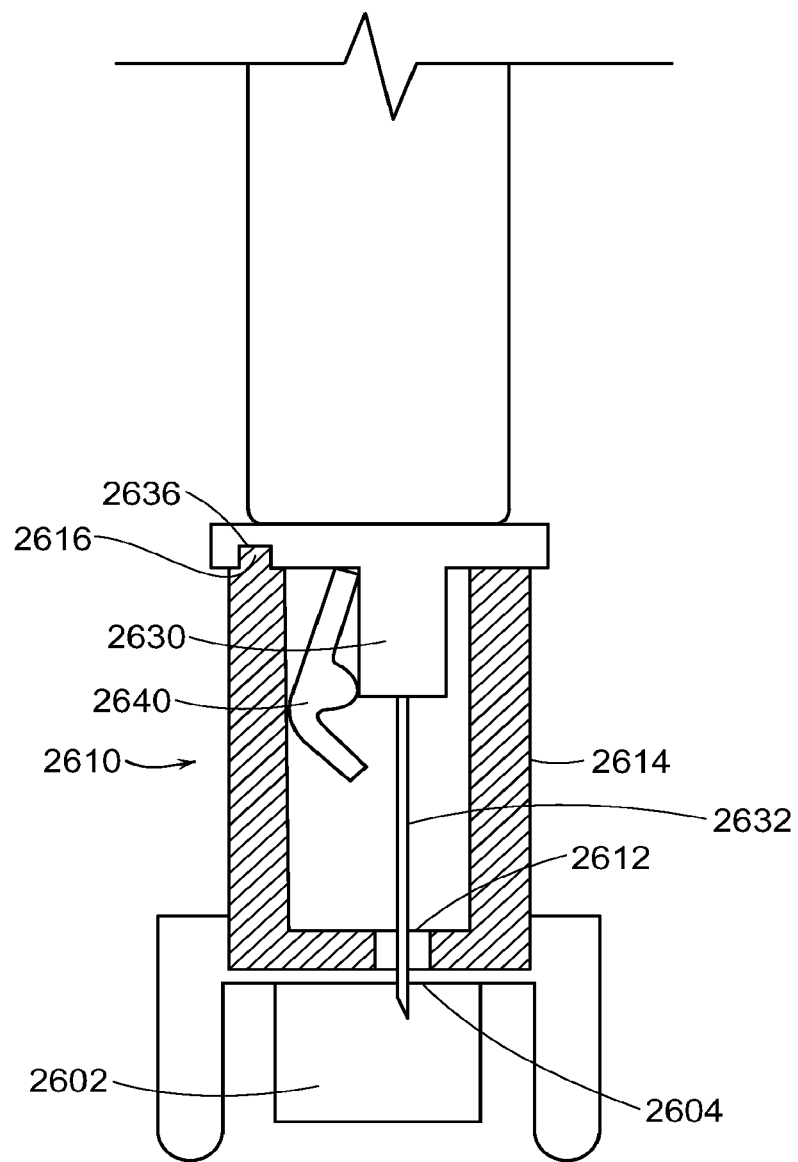
FIG. 26 illustrates another system comprising a needle hub and cap in accordance with another embodiment.

FIG. 26 illustrates a cross-sectional view of an attachment or cap 2610 configured to be fitted onto a medical device or a container 2602 (e.g., a vial) holding a liquid medication in which the cap 2610 covers the vial's septum 2604 or the container or vial or medical device entryway except for a hole 2612 that is off-axis from the center of the container/septum. The cap 2612 includes a side wall 2614 through which a needle hub 2630 must go in order for the needle 2632 to reach the septum. The top of the cap 2610 has a keying projection 2616 that has a geometry (size and shape) that mates with the geometry of a corresponding keying recess 2636 in the needle hub both to align the needle 2632 with the hole 2612 and to prevent a different type of needle from being used. The keying projection 2616, which may be on the cap or on the needle hub, has a height to prevent the needle from accessing the container or vial unless a matching syringe is used with the cap. The cap has a door 2640 that can block access and can be pushed out of the way similar to the doors 1752, 1852, and 1952, only by the corresponding needle hub. The hole 2612 in the cap 2610 may also have a cover which is pushed out of the way when the needle hub is inserted. A medical device may be fitted with similar geometry as the vial cap to match with the same needle hub 2630.

In some embodiments, the cap is attached to some or all containers of a given drug and would not be able to be, or would be very difficult to be, removed. The cap may be made of a molded plastic or of any other material; the cap may attach to the vial or other container by adhesive, welding, with a snap fit, or by any other method.

In other embodiments, a medical device, such as an infusion pump, may have a feature with geometry similar to that of the cap that mates only with the provided needle. The feature may be a standoff above the device septum that has a depression or hole to allow the provided needle hub to lower to the necessary height, but prevents any other needle type from reaching the septum. The needle hub may be molded plastic and may attach to a syringe or similar device.

The geometry of the key protrusion, as well as the relative angle of the needle and/or the offset distance of the needle from the center of the hub, may be changed for different drugs or dosages. If a user attempted to insert a standard needle or a needle with a different geometry into the container, it would hit the bottom of the cap in the center and/or be impeded by the geometry and not enter the cap at all. If the cutout is in the housing, the cap walls may be tall enough so that the syringe body must lower into the cap, which offers protection against a long needle bypassing the cap. Additionally or alternatively, the cap may have a protrusion that mates with a cutout in the needle hub. This would greatly reduce the risk of a standard needle entering the cap because it would interfere with the cap protrusion.

Figure 27:
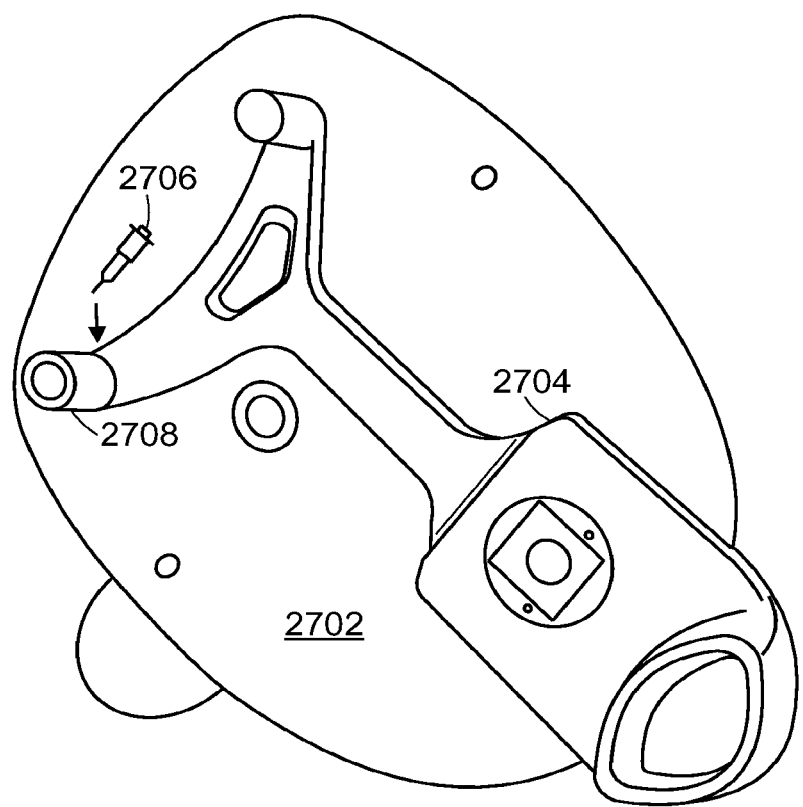
FIG. 27 illustrates a cover or cap for a medical device having a fill port standoff.

FIG. 27 illustrates a drug delivery or medical device 2702 and a drug filling component or cap 2704. The cap 2704 can also be considered to be a drug delivery device offset 2704, a fill port adapter 2704, or drug delivery device cap 2704. The underside or bottom of the drug delivery device 2702 is shown in FIG. 27. The drug delivery device 2702 can be used to provide or administer a drug (e.g., insulin) to a user. The drug delivery device 2702 can be a wearable device. The drug delivery device 2702 can be a single use device (e.g., intended for non-refillable, single dosage use) or a multiple use device (e.g., intended for refillable, multiple dosage use). The drug delivery device 2702 can be used for a short period of time and can be disposable.

In general, the drug delivery device 2702 can be filled with any drug to be provided to a user. The drug delivery device 2702 can be attached or adhered to a user. Once activated, the drug delivery device 2702 can administer a portion of a drug dosage contained within the drug delivery device 2702 over a desired amount of time. The drug delivery device 2702 can be provided with a preloaded dosage of a drug or can be provided without an included drug dosage. The drug delivery device 2702 can be provided with a fill port that provides access to the drug delivery device 2702. A drug dosage can be passed into the drug delivery device 2702 using the fill port. Typically, a syringe with a needle tip can be used to pierce a septum positioned in the fill port to enable access to the drug delivery device 2702. Once the septum of the fill port is pierced, a drug dosage contained in the syringe can be transferred to the drug delivery device 2702 through the fill port. In this way, the drug delivery device 2702 can be filled a single time for single use or can be re-filled for repeated use.

The cap 2704 is shown attached to a bottom portion or underside of the drug delivery device 2702. The cap 2704 can be of any shape or size. The cap 2704 can be shaped to fit or mate with a portion of the drug delivery device 2702 to secure the cap 2704 to the drug delivery device 2702. The cap 2704 can also include a fill port standoff 2708 that can be coupled to and/or aligned with the fill port of the drug delivery device 2702. The fill port standoff 2708 of the cap 2704 can aid or facilitate the transfer of a drug from a syringe to the drug delivery device 2702. The fill port standoff 2708 can also be considered to be a lead-in feature 2708.

In FIG. 27, an indicator 2706 (e.g., a graphic, label, or icon) on the drug delivery device 2702 can specify a location of a fill port on the drug delivery device 2702. FIG. 27 further shows a fill port standoff 2708 of the cap 2704 positioned over top of the fill port of the drug delivery device 2702. The fill port standoff 2708 can be aligned with the fill port of the drug delivery device 2702. A top of the fill port standoff 2708 can provide an opening that can be accessed by a system (e.g., a syringe with a needle tip) for transferring a drug from a container to the drug delivery device 2702. For example, a syringe with a needle tip can be inserted into the fill port standoff 2708 to penetrate a septum of a fill port on the drug delivery device 2702. After penetrating the septum, the drug contained in the syringe can be transferred to the drug delivery device. In general, the fill port standoff 2708 can help a user align the syringe with the fill port of the drug delivery device 2702 to facilitate insertion of a desired drug and dosage into the drug delivery device 2702.

Conventional devices used to provide access to a fill port of a drug delivery device can suffer from one or more drawbacks. One common drawback can involve the misalignment or misplacement of the needle tip of a syringe relative to the fill port of a drug delivery device and relative to any standoff of a cap coupled to the drug delivery device. In general, the needle tip of the syringe should be precisely oriented in the fill port so that the needle tip properly pierces the septum of the drug delivery device. When attempting to access a fill port, the needle tip can frequently get stuck or caught against an interior sidewall of a fill port standoff of the cap. When this occurs, the needle tip may be pressed into the sidewall, preventing a plunger of the syringe from being advanced to deliver a drug from the syringe. Alternatively, when the needle tip is pressed into the interior sidewall rather than the septum, the drug dosage can be transferred incorrectly and not into the fill port of the drug delivery device. This can result in spillage or overflow of the drug. In turn, the intended drug dosage to a user may not be fully provided to the drug delivery device, thereby resulting in waste, increased costs, and potentially even severe medical or health problems.

Accordingly, there is a need for a cap or fill component that includes a fill port standoff that guides the needle tip of a syringe to the septum of a drug delivery device such that a drug dosage from the syringe to the drug delivery device can occur without spillage or waste in a more efficient and easy to use manner.

Figure 28A:
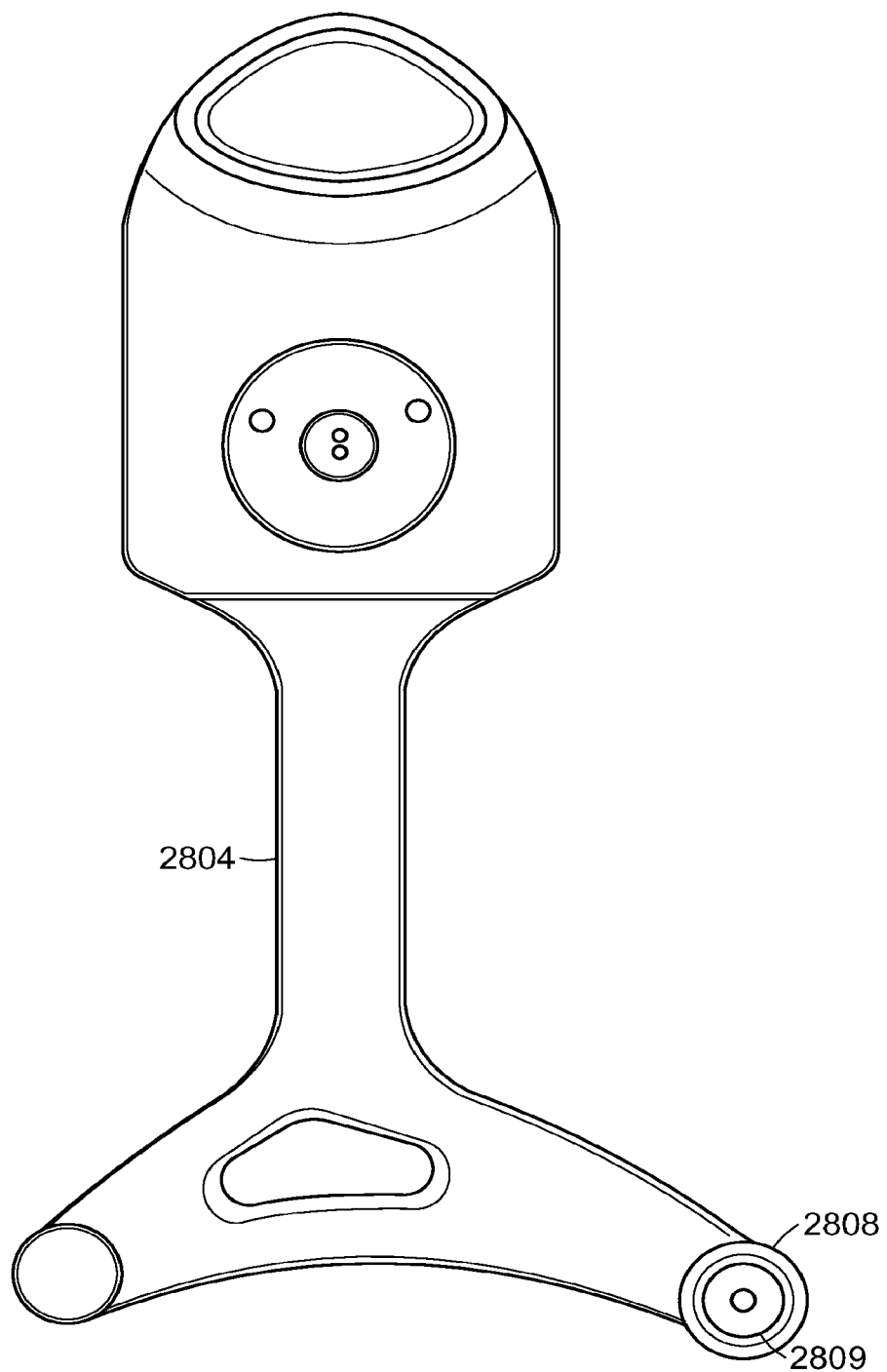
FIGS. 28A through 28E illustrate a cover or cap for a medical device having a fill port standoff with a cone insert.

FIG. 28A illustrates a cap 2804 having an improved fill port standoff 2808. The cap 2804 can be used to facilitate transfer of a drug to a drug delivery device (e.g., the drug delivery device 802). The cap 2804 can be designed to be attached or secured to a portion of the drug delivery device to facilitate filling the drug delivery device with a drug. The cap 2804 can be of any shape or size and can be designed to attach to an underside of a drug delivery device. The cap 2804 can be made of any suitable material including, but not limited to, plastic.

The fill port standoff 2808 of the cap 2804 can be positioned over a fill port of a drug delivery device when the cap 2804 is attached or coupled to the drug delivery device. A needle tip of a syringe can be positioned within the fill port standoff 2808. The fill port standoff 2808 can provide access to a septum of the drug delivery device that is to be pierced to allow a drug to be transferred from a syringe to the drug delivery device.

Figure 28B:
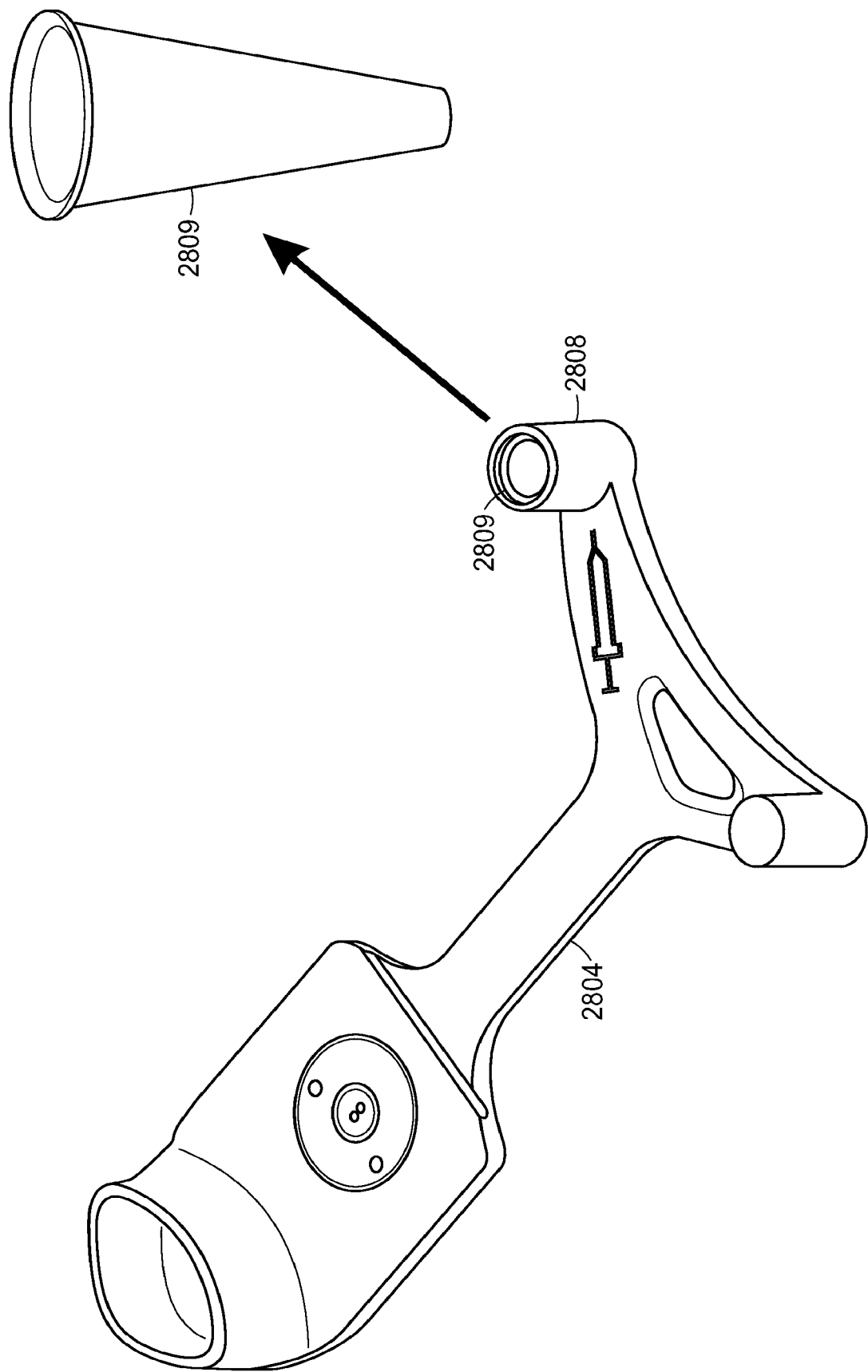

As shown in FIGS. 28A and 28B, a cone insert 2809 can be positioned within the fill port standoff 2808. The cone insert 2809 can be made of any suitable material such as, for example, stainless steel. The cone insert 2809 can fit within the fill port standoff 2808 and can be used to improve the alignment of a needle tip of a syringe with a fill port of a drug delivery device.

FIG. 28B illustrates an isometric view of the cap 2804. As shown in FIG. 28B, the cone insert 2809 can be shaped as an inverted cone with a decreasing or relatively smaller hole diameter in a lower region and an increasing or relatively larger hole diameter in an upper region. The cone insert 2809 can include a lip or edge at or near the top of the cone insert 2809. The lip of the cone insert 2809 can be used to secure the cone insert 2809 to the fill port standoff 2808. The bottom of the cone insert 2809 can be positioned adjacent to or in proximity to a fill port/septum of a drug delivery device. The cone shape and hard material used to form the cone insert 2809 can help guide a needle tip to a bottom of the cone insert 2809 and on to the septum while also preventing a needle tip from getting stuck on a sidewall of the fill port standoff 2808. As such, the cone insert 2809 can improve the reliability of transferring a drug from a syringe to a drug delivery device.

The fill port standoff 2808 can be shaped to accept the cone insert 2809. Once positioned into the fill port standoff 2808, the cone insert 2809 can be secured to the fill port standoff 2808. As an example, for a plastic fill port standoff 2808, the fill port standoff 2808 can be heated through heat staking or heat swaging. In doing so, a plastic portion of the fill port standoff 2808 can fold over and down over the top ridge or lip of the cone insert 2809 to secure the cone insert 2809 into place. When cooled, the top plastic portion of the fill port standoff 2808 can tightly secure the cone insert 2809 into a final desired position.

Figure 28C:
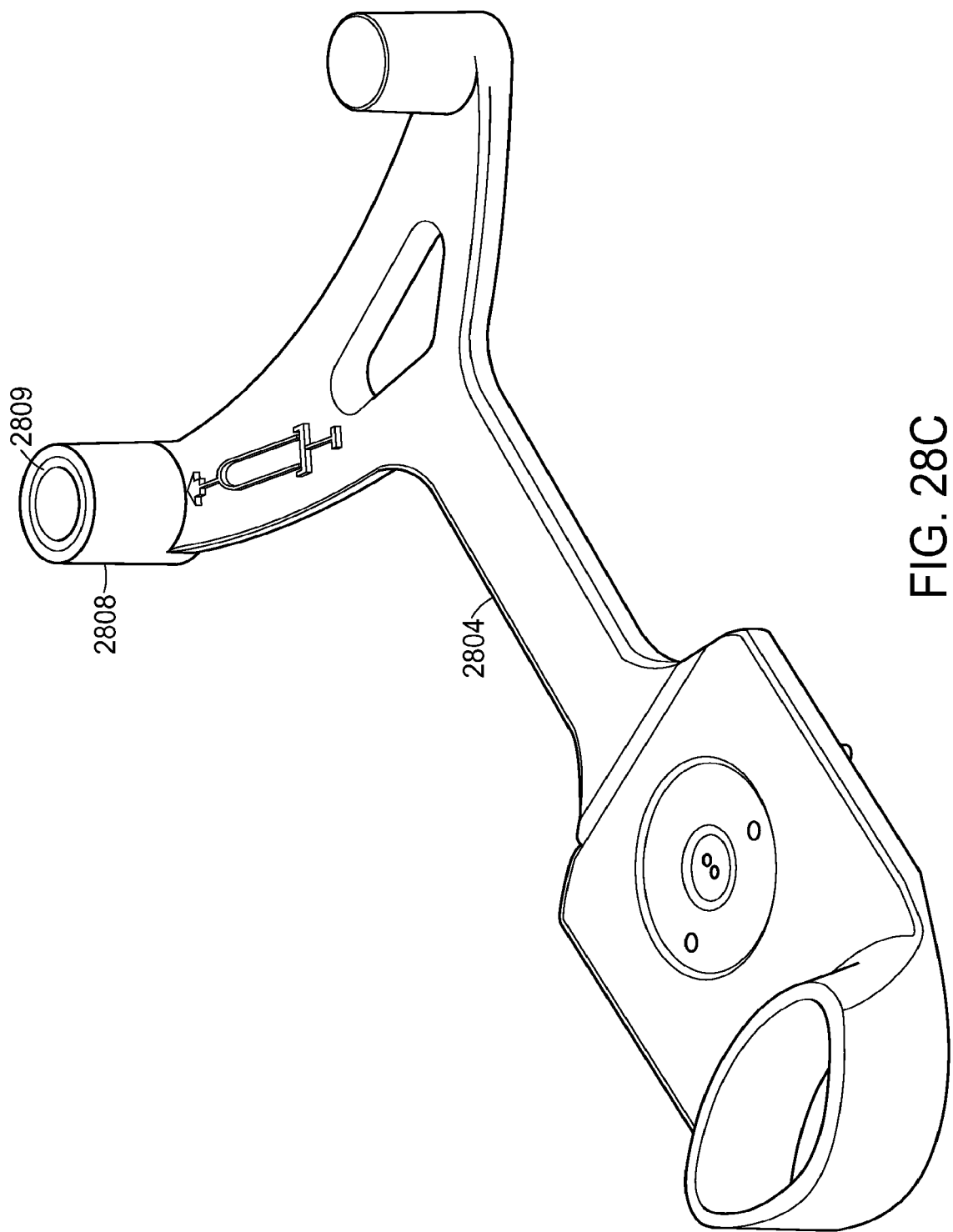

FIG. 28C illustrates a second isometric view of the cap 2804. The arrangement of the fill port standoff 2808 and the cone insert 2809 is shown in FIG. 28C.

Figure 29:
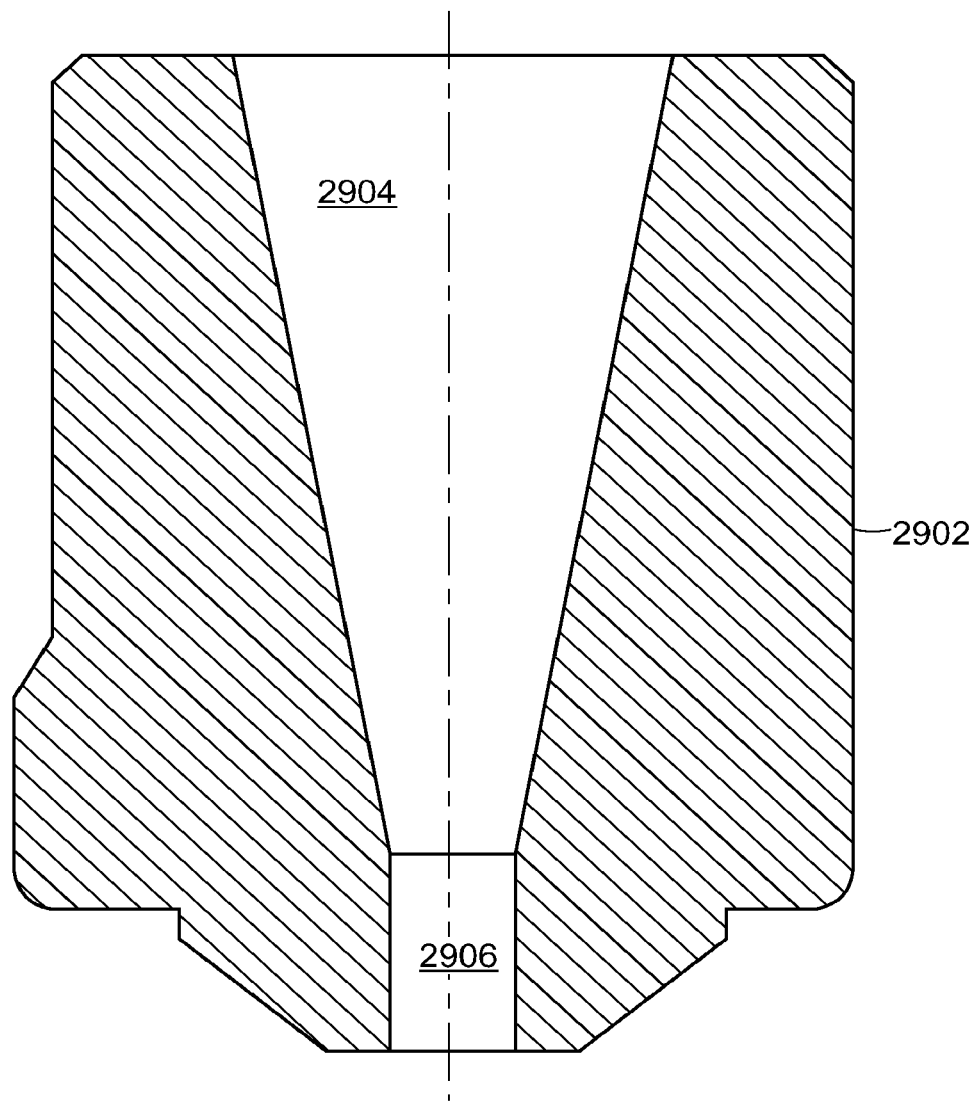
FIG. 29 illustrates a conventional fill port standoff.

FIG. 29 illustrates a cutaway view of a conventional fill port standoff 2902 used on a conventional cap that can suffer from one or more of the drawbacks discussed above. As shown in FIG. 29, the fill port standoff 2902 includes a hole or open area comprising a first open area 2904 and a second open area 2906. A needle can enter the fill port standoff 2902 at the top of the open area 2904. The bottom of the open area 2906 can be positioned over a fill port/septum of a drug delivery device. The open area 2904 can be shaped like an inverted cone with decreasing diameter relative to the top of the open area 2904. The open area 2906 can be of a constant diameter. Generally, the open areas 2904 and 2906 are circular in cross-sectional shape. As discussed above, the fill port standoff 2902 is generally made of plastic and needle tips can often get stuck on the inner sidewalls of the fill port standoff 2902 (e.g., along the inner walls defining the open area 2904). Consequently, the needle tip may not reach the bottom of the open area 2906 in order to pierce the septum of the drug delivery device.

Figure 28D:
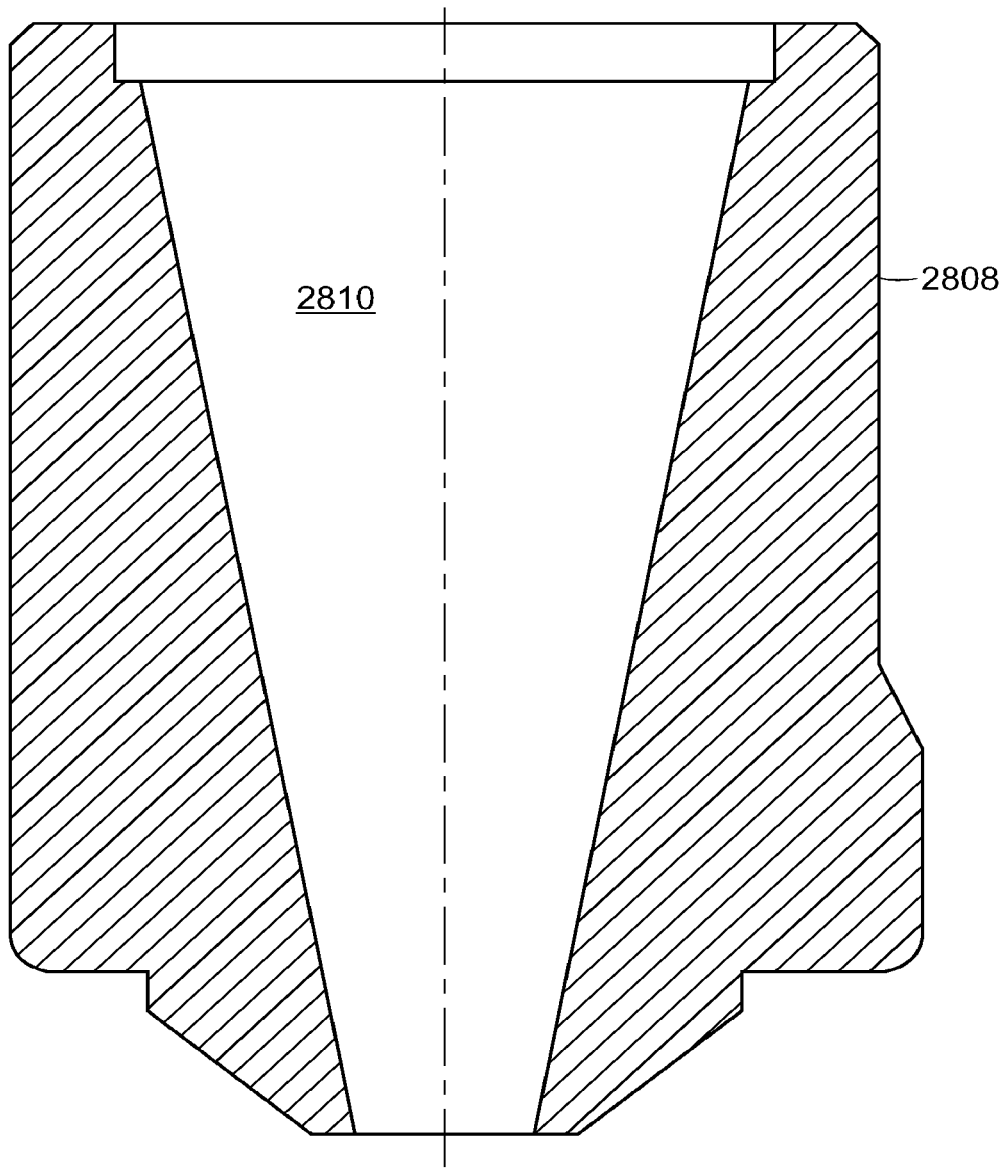

FIG. 28D illustrates an improved fill port standoff—for example, the fill port standoff 2808—prior to placement of a cone insert. The fill port standoff 2808 can include an open area 2810. As shown, the open area 2810 can be shaped as an inverted cone. The open area 2810 can be circular in shape (cross-section) and can have a decreasing diameter relative to a top of the fill port standoff 2808. The bottom of the open area 2810 can be positioned over a fill port and septum of the drug delivery device. Contrary to the fill port standoff 2902, the fill port standoff 2808 may have a single open area 2810 (i.e., it may not include a second constant diameter open area positioned just above a fill port of a drug delivery device).

Figure 28E:
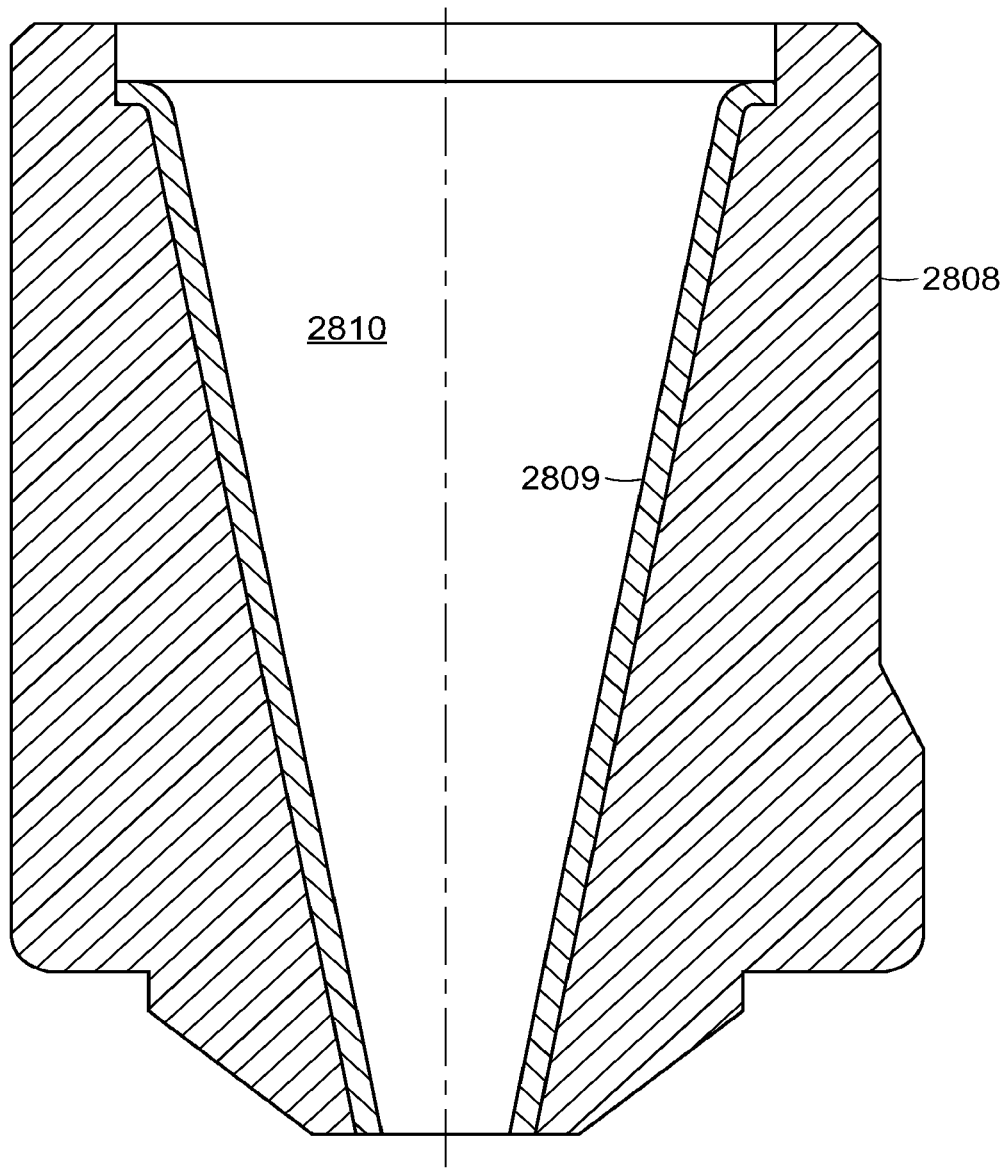

FIG. 28E illustrates the cone insert 2809 positioned within the fill port standoff 2808. As shown in FIG. 28E, the cone insert 2809 can fit within and can substantially occupy the open area 2810. A top portion of the fill port standoff 2808 can include plastic that can be heated to fold down over the top ridge or lip of the cone insert 2809 (alternatively, a plastic portion of the fill port standoff 2808 can at least contact a portion of the cone insert 2809 in order to secure the cone insert 2809 into place). The cone insert 2809 as shown in FIG. 28E provides a guide for aligning a needle tip from the top of the fill port standoff 2808 to the bottom of the fill port standoff 2809, thereby improving the reliability of the needle tip to pierce a septum of a drug delivery device to effectively transfer a drug to the drug delivery device.

Figure 30B:
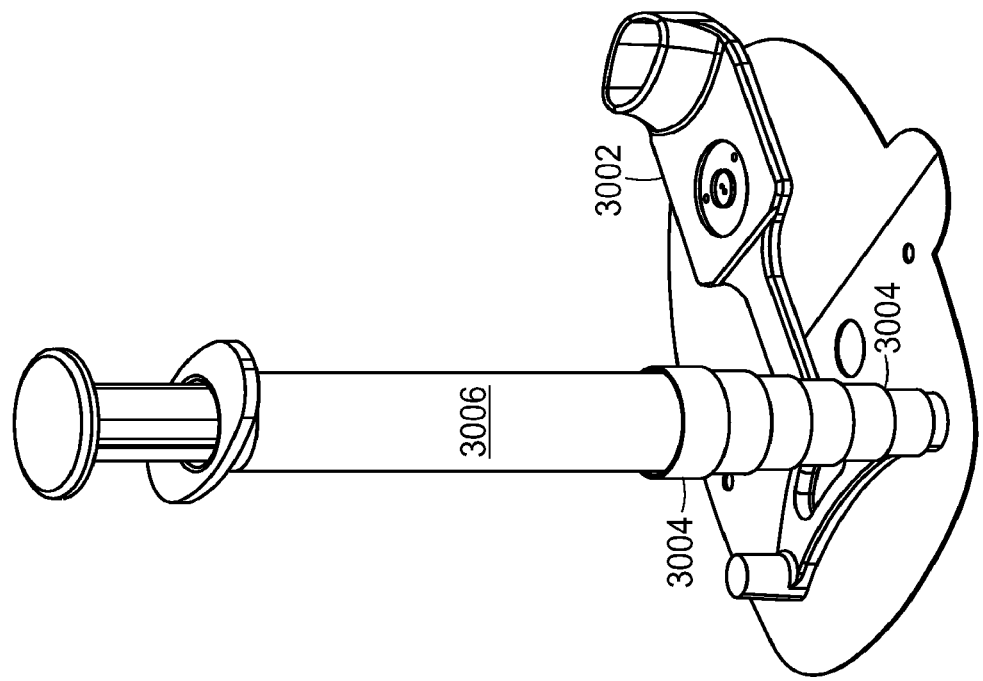
FIGS. 30A through 30C illustrate a cover or cap for a medical device having a fill port standoff incorporating a collapsible funnel.
Figure 30A:
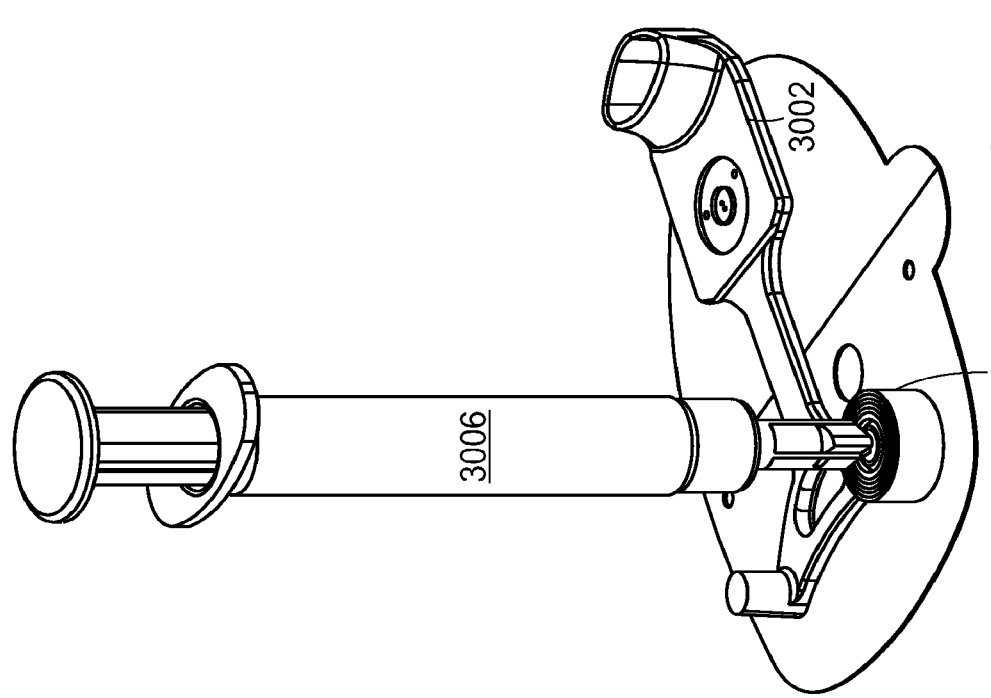
Figure 30C:
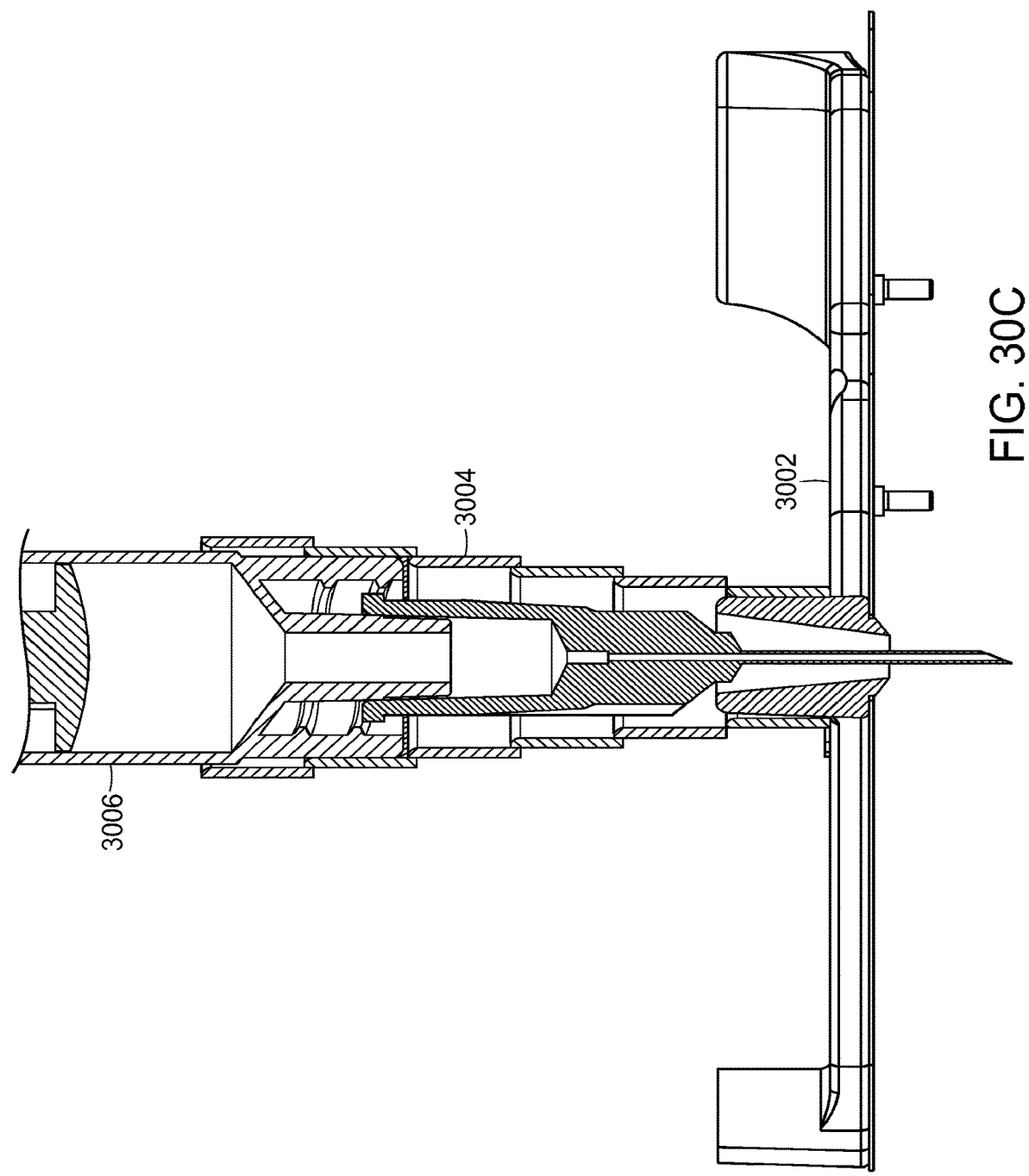

FIGS. 30A through 30C illustrate another improved cap 3002 that can also provide improved delivery of a drug from a syringe to a drug delivery device. Two views of the cap 3002 are shown in FIGS. 30A and 30B to illustrate its operation.

The cap 3002 can be similar in shape, construction, and operation as the fill cap 2804. As shown in FIG. 30A, a fill port standoff 3004 of the cap 3002 can comprise a collapsible funnel. The collapsible funnel fill port standoff 3004 can be made of plastic. The collapsible funnel fill port standoff 3004 can be made at low cost and can be disposable. Further, the collapsible funnel fill port standoff 3004 can have a small footprint to simplify packing, storage, and shipping of the cap 3002. The collapsible funnel fill port standoff 3004 can help align a syringe 3006 with a needle tip with a fill port of a drug delivery device that can be coupled to the cap 3002. FIG. 30A shows the fill port standoff 3004 in a collapsed state, and FIG. 30B shows the fill port standoff 3004 in an extended state. A user can pull up on the outer portion of the fill port standoff 3004 to raise or extend the fill port standoff 3004.

FIG. 30C illustrates a cut away view of the collapsible funnel fill port standoff 3004. As shown in FIG. 30C, a syringe 3006 can be positioned within the collapsible funnel fill port standoff 3004. The collapsible funnel fill port standoff 3004 can provide a guide for aligning the syringe 3006 with a fill port of a drug delivery device. For example, as shown in FIG. 30C, a needle tip of the syringe 3006 is shown below the collapsible funnel fill port standoff 3004 indicating its ability to access a septum region or area of a drug delivery device. The collapsible funnel fill port standoff 3004 can support the syringe 3006 as shown in FIG. 30C to ensure alignment of the syringe 3006 and the fill port of the drug delivery device. As an example, an interior of the fill port standoff 3004 can be shaped to match or mate with a portion of the syringe 3006 to provide a stable fit between the syringe 3006 and fill port standoff 3004 when transferring a drug to the drug delivery device.

FIGS. 31A through 31D illustrate another embodiment with a cap 3102. The cap 3102 can function similarly to the cap 2804 and/or the cap 3002 in that the cap 3102 can provide improved delivery of a drug from a transfer device to a drug delivery device.

The cap 3102 can include a fill port standoff 3104. The fill port standoff 3104 can extend from a base of the cap 3102.

Figure 31A:
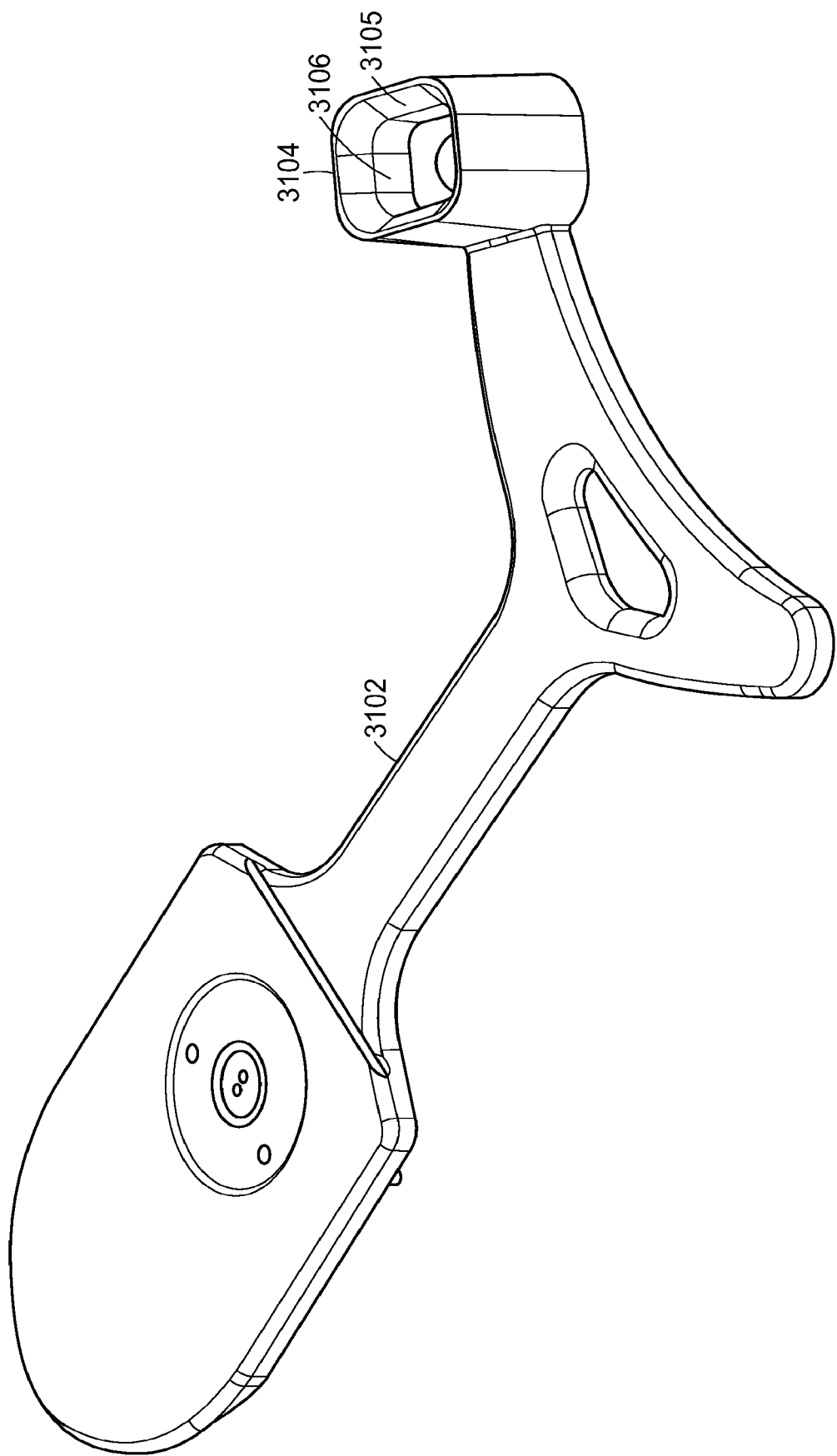
FIGS. 31A through 31D illustrate a cover or cap for a medical device, a needle hub, and a cap for a liquid drug container in accordance with another embodiment.

As shown in FIG. 31A, the interior of the fill port standoff 3104 can comprise an outer raised region 3105. This outer raised region 3105 can be slanted or angled towards the interior of the fill port standoff 3104 and can be shaped to meet a lower inner region 3106 of the fill port standoff 3104. The lower inner region 3106 can have a constant cross-sectional shape in the form of a rectangle having rounded corners, the rectangle having a length L1 and a width W1. The outer raised region 3105 at its lower end has a cross-sectional shape matching the cross-sectional shape of the lower inner region 3106, while the outer raised region 3105 is angled outwardly and upwardly so that the outer raised region 3105 at its upper end has a cross-sectional shape in the form of a larger rectangle with rounded corners, the rectangle having a length L2 and a width W2, where L2 is greater that L1 and W2 is greater than W1.

The height and interior shape of the fill port standoff 3104 can be formed to match or mate with a particular needle hub (e.g., a needle hub of a syringe). That is, the fill port standoff 3104 can be shaped so that a particular shaped needle hub fits properly into the fill port standoff 3104 to enable the needle of the needle hub to properly reach and pierce a septum of a drug delivery device coupled to the cap 3102. In this way, a proper type or dosage of a drug to be provided through a particular type of needle hub can be assured of gaining access to the drug delivery device through the cap 3102, while needle hubs having different shapes (e.g., containing incompatible or incorrect types or dosages of drugs) are unable to access the septum of an attached drug delivery device.

For example, the fill port standoff 3104 can be shaped and arranged to match or mate with a needle hub used for delivering a relatively higher concentration of insulin (e.g., a U200 dosage). As such, a needle hub associated with a relatively lower concentration of insulin (e.g., a U100 dosage) can be shaped so as to not be able to fit into the fill port standoff 3104. In this way, the cap 3102 can ensure that only the higher concentration of insulin is provided to an attached drug delivery device while further ensuring that the lower concentration of insulin is not capable of being delivered to the drug delivery device.

As a further measure of ensuring that the correct type and dosage of drug is delivered, the fill port standoff 3104 can have a height that requires a needle of at least a certain threshold height to reach a septum of a coupled drug delivery device. In this way, a shorter needle (e.g., a needle attached to a needle hub designed for an incompatible type or dosage of drug) is unable to traverse the entire fill port standoff 3104 and cannot reach the septum.

The fill port standoff 3104 can also improve the delivery of a drug to a drug delivery device by ensuring a syringe/needle hub is properly aligned with a fill port of the drug delivery device. As described above, alignment of a needle tip to a fill port can be challenging. By having the shape of the fill port standoff 3104 match or mate with a needle hub associated with a syringe containing a desired drug dosage, the alignment of the needle tip and the fill port of the drug delivery device can be ensured, thereby resulting in more efficient and reliable drug dosage delivery to the drug delivery device. The mechanism for ensuring that only a needle hub of a certain shape can access a fill port septum of a drug delivery device by matching or mating with a corresponding fill port standoff 3104 can be considered to be a keyed interface. That is, access to the septum can be restricted to only properly shaped needle hubs.

Figure 31B:
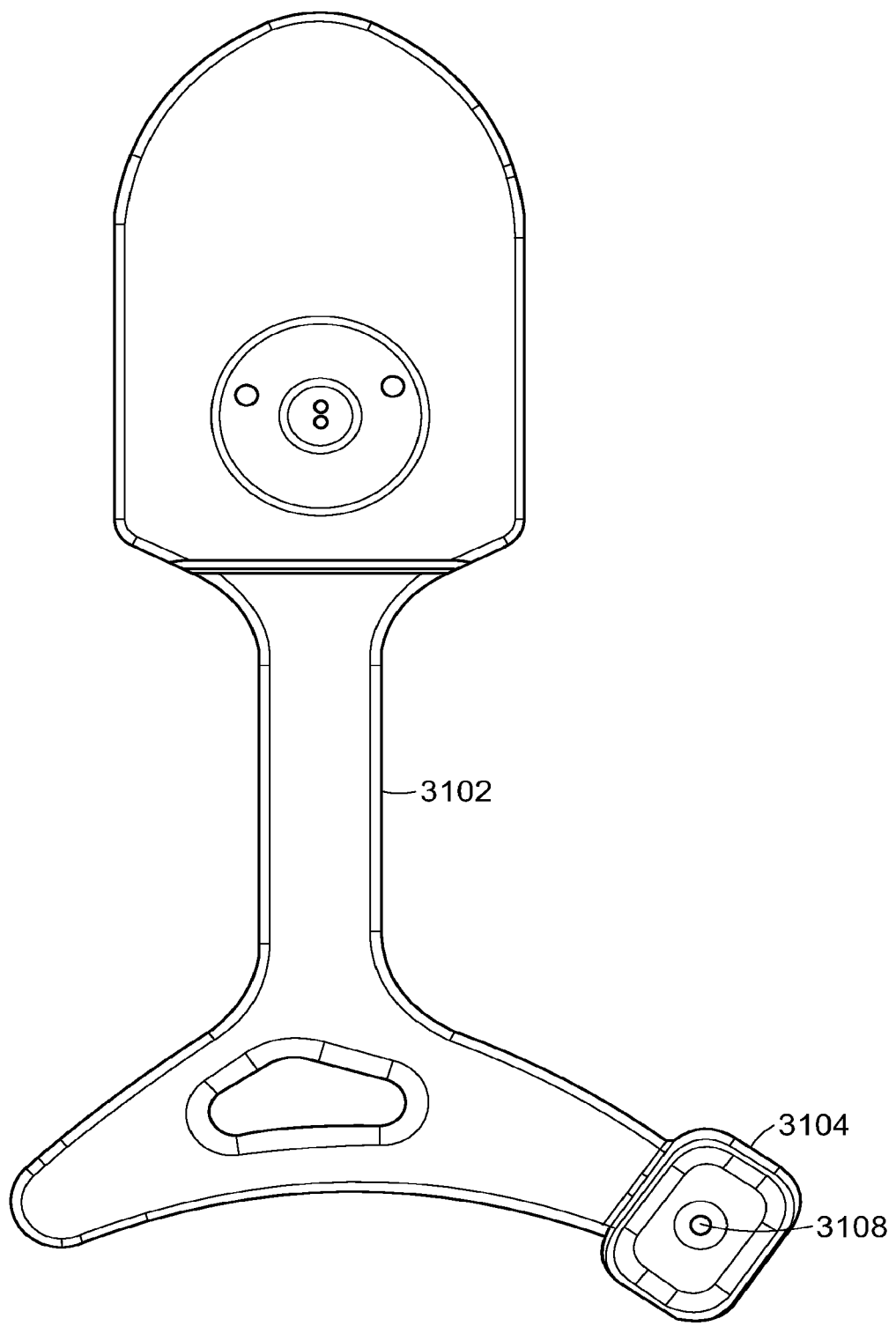

FIG. 31B illustrates a top view of the cap 3102. As shown in FIG. 31B, the fill port standoff 3104 includes a hole 3106 in approximately a center of the fill port standoff 3104. The hole of the fill port standoff 3104 can be aligned with a fill port of a drug delivery device when the cap 3102 is coupled or attached to the drug delivery device. FIG. 31B further shows that a needle hub of only a certain shape can properly fit into the fill port standoff 3104 in order to access a septum of an associated fill port of a drug delivery device (thereby providing a portion of the keyed interface for ensuring proper drug type and dosage delivery).

Figure 31C:
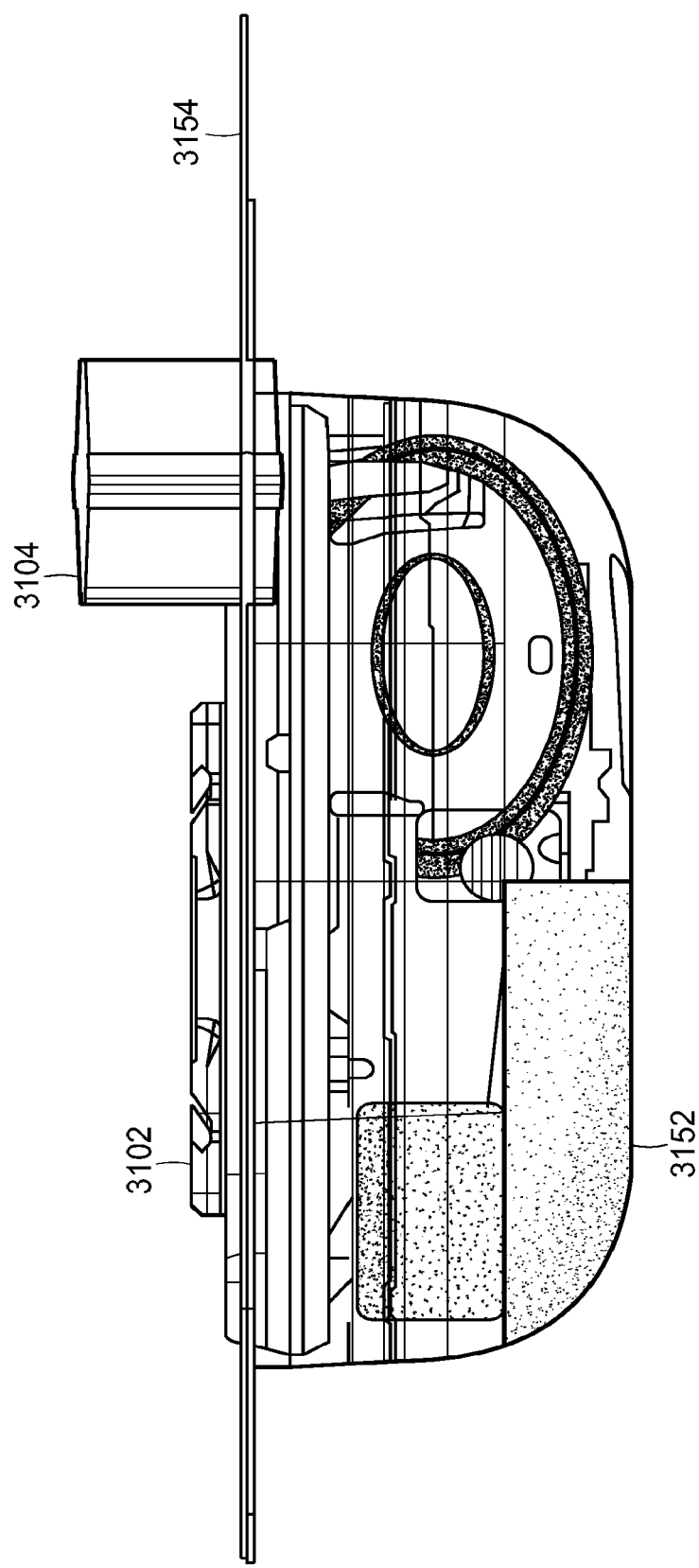

FIG. 31C illustrates the cap 3102 coupled to a drug delivery device 3152. The drug delivery device 3152 can represent the drug delivery device 2702 described in relation to FIG. 27. As shown in FIG. 31C, the cap 3102 can be attached to a bottom side or underside of the drug delivery device 3152. The fill port standoff 3104 can be aligned with a fill port of the drug delivery device 3152. An adhesive portion 3154 of the drug delivery device 3152 is also shown. The adhesive portion 3154 can be used to adhere the drug delivery device 3152 to a user once the drug delivery device 3152 is provided with a drug dosage to be administered to the user.

A further benefit of the fill port standoff 3104 is that its height can be set such that a needle used to access the fill port does not penetrate the fill port too deeply. Specifically, the fill port standoff 3104 can be formed to be at a height such that a needle used to deliver a drug to the drug delivery device 3152 can penetrate the septum but does not penetrate so far as to hit any reservoir or other component of the drug delivery device 3152. This can protect both the syringe needle and the drug delivery device 3152.

Figure 31D:
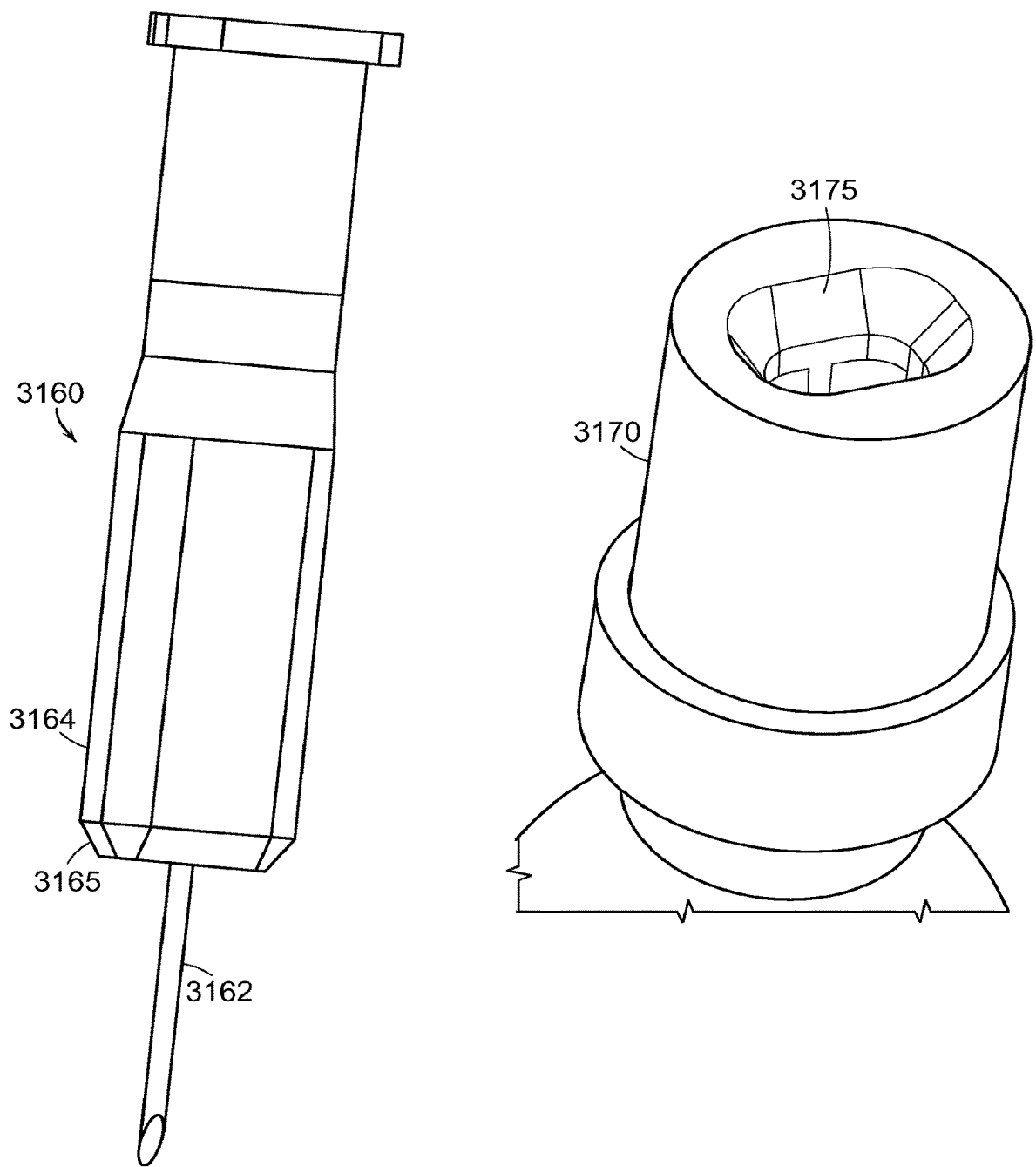

FIG. 31D shows a syringe 3160 that can be used with cap 3102 as well as a vial adapter or cap 3170 that can be on top of a vial containing drug for the medical device associated with cap 3102. The syringe 3160 has a needle hub 3164 and a needle 3162. The needle hub 3164 has a keying feature 3165 having a size and shape to fit with the fill port standoff 3104. The angled outer surface of the keying feature 3165 matches the angled surface of the outer raised region 3105 of the fill port standoff 3104. The cap 3170 can be attached to a liquid drug container or vial as described above. The upper entrance to the cap 3170 has an opening and a keying feature 3175 that matches the keying feature 3165 of the syringe. The keying feature 3175 has a size and shape matching the angled surface of the outer raised region 3105 of the fill port standoff 3104. In this way, the syringe 3160, the vial cap 3170, and the medical device cap 3102 ensure that only the correct drug from the correct vial is used to fill the medical device.

Figure 32A:
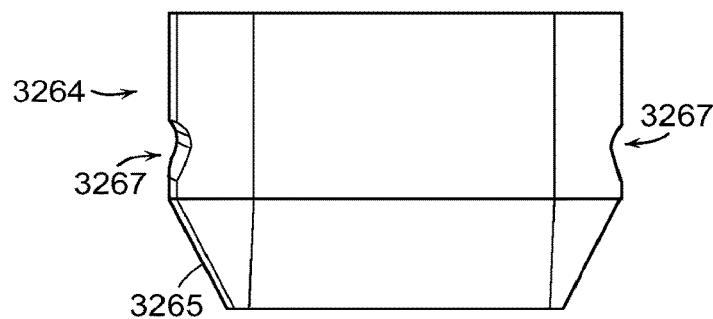
FIGS. 32A through 32C illustrate another embodiment similar to that shown in FIGS. 31A through 31D, with snap features.
Figure 32B:
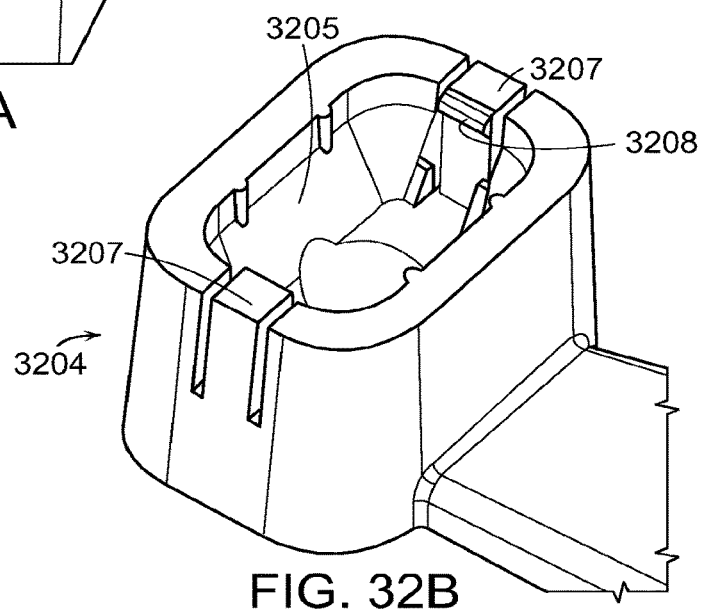
Figure 32C:
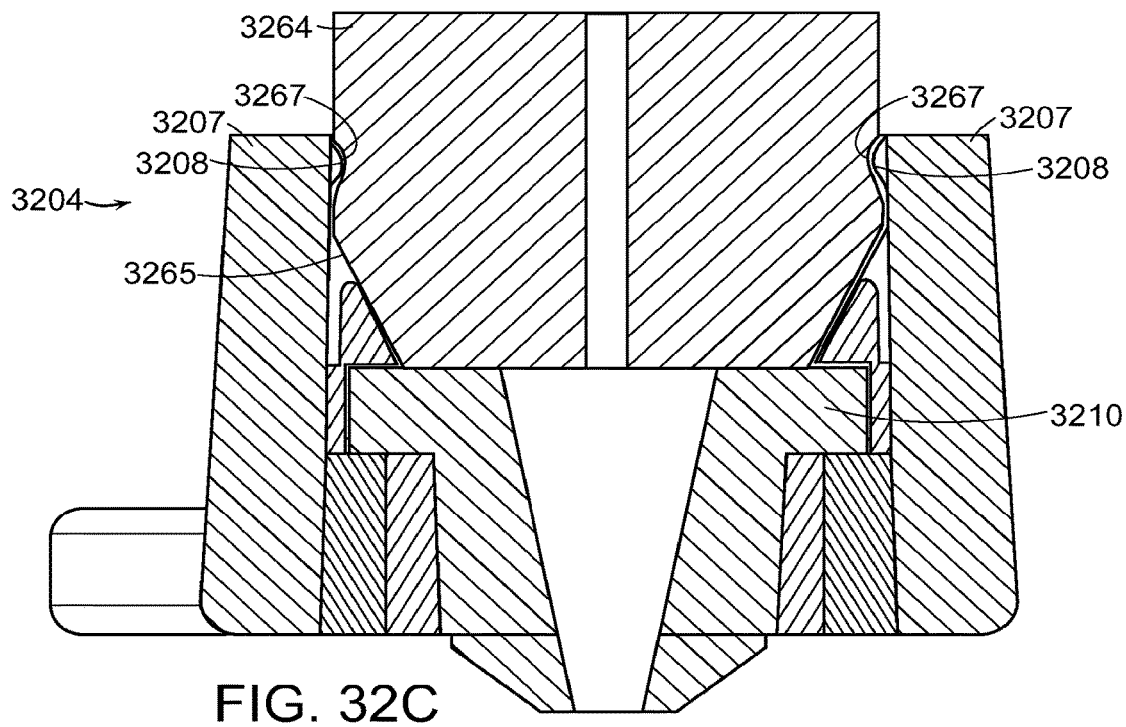

FIGS. 32A through 32C show another embodiment similar to the embodiment of FIGS. 31A through 31D. In this embodiment the needle hub 3264 has a keying feature 3265 similar to the keying feature 3165. The needle hub also has two notches 3267 as shown. The fill port standoff 3204 is similar to the fill port standoff 3104 with a region 3205 shaped like the region 3105. The fill port standoff also has snap features in the form of flexible arms 3207 with projections 3208 on their ends. When the syringe is inserted into the fill port standoff 3204, the flexible arms 3207 flex and then the projections 3208 snap into the notches 3267, as shown in FIG. 32C. This helps fix the position of the syringe, while allowing easy insertion and removal of the syringe. A vial adapter or cap may have a similar construction with snap features in the form of flexible arms and projections for mating in a similar manner with the needle hub 3264.

Figure 33A:
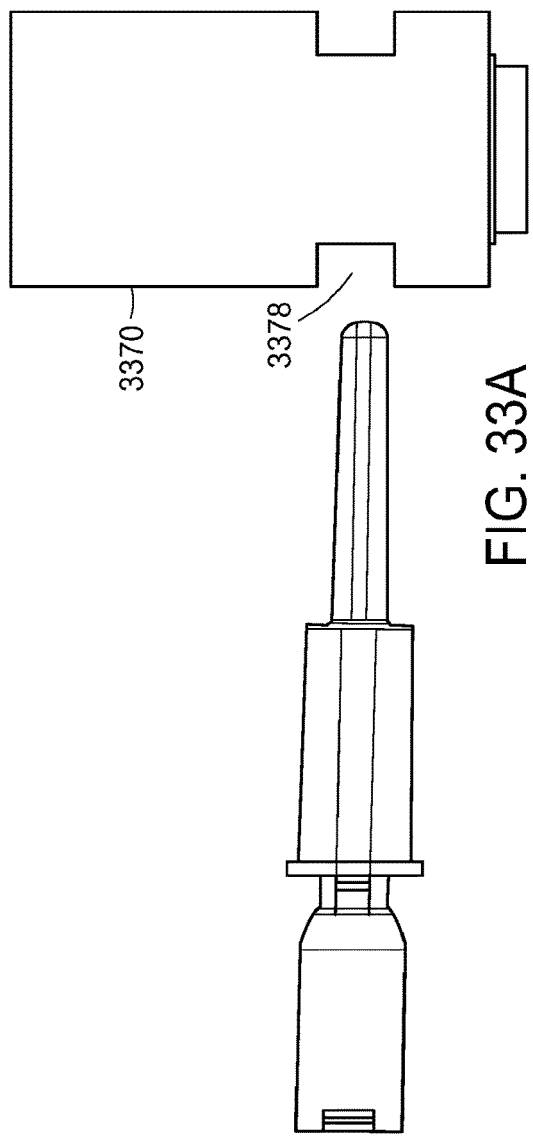
FIGS. 33A and 33B illustrate a cap with a passageway to facilitate access to a septum of a container or vial.
Figure 33B:
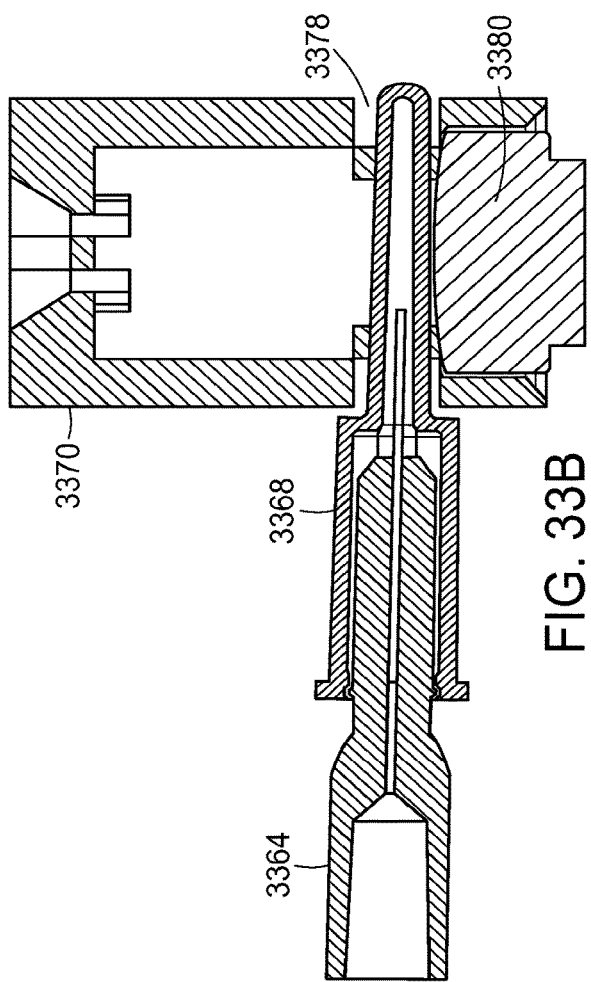

FIGS. 33A and 33B show another embodiment. The vial adapter or cap 3370 is similar to the vial adapter or cap 3170, except that the vial adapter or cap 3370 has a transverse passage 3378 across it. FIG. 33B shows a needle cap 3368 on a needle hub 3364 of a syringe being passed through the passageway 3378. A disinfecting swab may be placed on the needle cap 3368 to swab the septum on top of the vial 3380 to disinfect it before inserting a needle to withdraw drug from the vial.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for filling a medication reservoir of a medical device with a medication, the method comprising:
   mating a medical device nest in a baseplate with the medical device, the medical device nest comprising at least one keying feature that prevents types of medical devices different from a type of the medical device from mating with the medical device nest;
   mating a medication nest in the baseplate with a drug container, the medication nest comprising at least one keying feature that prevents types of containers different from a type of the drug container from mating with the medication nest; and
   pumping medication from a pump mechanism coupled to the baseplate and aligned with the medical device nest and the medication nest from the drug container to the reservoir of the medical device.

2. The method of claim 1, further comprising:
   detecting, via the at least one keying feature, electric characteristics of circuitry for the drug container;
   detecting a match of the electrical characteristics to expected values;
   in response to the detected match, sending a signal to a receiver circuit in the medical device; and
   enabling, upon receipt of the signal, transfer of medication to the medical device.

3. A system for filling a medication reservoir of a medical device with a medication, the system comprising:
   a medical device nest configured for mating with the medical device, the medical device nest comprising at least one keying feature that prevents types of medical devices different from a type of the medical device from mating with the medical device nest;
   a medication nest configured for mating with a drug container, the medication nest comprising at least one keying feature that prevents types of containers different from a type of the drug container from mating with the medication nest;
   means for moving medication from the drug container to the reservoir of the medical device; and
   a baseplate that defines the medical device nest and the medication nest and having a location for coupling the means for moving medication to the baseplate.

4. The system of claim 3, wherein the drug container comprises a vial, a cartridge, an auto injector, a pen, a pre-filled syringe or an empty syringe.

5. The system of claim 3, wherein the means for moving medication comprises a pump.

6. The system of claim 5, wherein the pump comprises an infusion pump.

7. The system of claim 3, wherein the at least one keying feature of the medical device nest comprises a recess or tab.

8. The system of claim 3, wherein the medical device nest comprises a keying feature that is positive or negative and wherein the medication nest comprises a keying feature that is positive or negative.

9. The system of claim 3, further comprising circuitry to detect electrical characteristics of the drug container using electrical contacts on the drug container and to compare the electrical characteristics to expected values.

10. The system of claim 9, further comprising sending a wireless signal to the medical device if the electrical characteristics match the expected values.

11. The system of claim 3, wherein a keying feature is integrated with the drug container or medical device.

12. The system of claim 3, wherein a keying feature is integrated with an attachment attached to the drug container or medical device.

13. The system of claim 3, wherein a keying feature of the drug container resembles a keying feature of the medical device.

* * * * *